US012789003B2

(12) United States Patent
Curtis et al.

(10) Patent No.: US 12,789,003 B2
(45) Date of Patent: Nov. 10, 2026

(54) ORAL CARE DEVICES, KITS, AND METHODS OF USE

(71) Applicant: The Procter & Gamble Company, Cincinnati, OH (US)

(72) Inventors: Michael David Curtis, Mason, OH (US); Paul Albert Sagel, Mason, OH (US); Jayanth Rajaiah, Loveland, OH (US); Matthew Lloyd Newman, Oberursel (DE)

(73) Assignee: The Procter & Gamble Company, Cincinnati, OH (US)

( * ) Notice: Subject to any disclaimer, the term of this patent is extended or adjusted under 35 U.S.C. 154(b) by 28 days.

(21) Appl. No.: 18/675,720

(22) Filed: May 28, 2024

(65) Prior Publication Data

US 2024/0399162 A1 Dec. 5, 2024

Related U.S. Application Data

(60) Provisional application No. 63/505,163, filed on May 31, 2023, provisional application No. 63/505,188,
(Continued)

(51) Int. Cl.
*A61N 5/06* (2006.01)
*A61C 19/06* (2006.01)
(Continued)

(52) U.S. Cl.
CPC .......... *A61N 5/0603* (2013.01); *A61C 19/066* (2013.01); *A61K 8/22* (2013.01);
(Continued)

(58) Field of Classification Search
CPC .................................................... A61C 19/066
See application file for complete search history.

(56) References Cited

U.S. PATENT DOCUMENTS

| | | | |
|---|---|---|---|
| 5,309,277 | A | 5/1994 | Deck |
| 5,879,691 | A | 3/1999 | Sagel |

(Continued)

FOREIGN PATENT DOCUMENTS

| | | | |
|---|---|---|---|
| CN | 201015606 | Y | 2/2008 |
| WO | 2003020160 | A1 | 3/2003 |

(Continued)

OTHER PUBLICATIONS

PCT Search Report and Written Opinion for PCT/US2024/030298 dated Oct. 17, 2024, 23 pages.

(Continued)

*Primary Examiner* — Heidi M Eide
(74) *Attorney, Agent, or Firm* — John G. Powell

(57) ABSTRACT

Oral care light devices, kits, and methods are provided. An oral care light device may include a housing, a light source positioned in the housing, the light source being capable of emitting electromagnetic radiation having an average light intensity of about 150 mW/cm$^2$ or greater. The oral care light device may include a battery and may be portable. A kit may include an oral care light device and a whitening composition. A method of whitening teeth using an oral care light device may include applying a whitening composition including a bleaching agent to a tooth, maintaining the whitening composition on the tooth for a first time period without activating the light source, and, after the first time period, activating the light source to direct the electromagnetic radiation toward the tooth for a second time period.

19 Claims, 13 Drawing Sheets

Related U.S. Application Data filed on May 31, 2023, provisional application No. 63/505,169, filed on May 31, 2023.

(51) Int. Cl.
*A61K 8/22* (2006.01)
*A61Q 11/00* (2006.01)

(52) U.S. Cl.
CPC ............ *A61N 5/0613* (2013.01); *A61Q 11/00* (2013.01); *A61C 2204/002* (2013.01); *A61K 2800/81* (2013.01); *A61N 2005/0606* (2013.01); *A61N 2005/0651* (2013.01); *A61N 2005/0652* (2013.01); *A61N 2005/066* (2013.01); *A61N 2005/0661* (2013.01); *A61N 2005/0663* (2013.01)

(56) References Cited

U.S. PATENT DOCUMENTS

| | | | | |
|---|---|---|---|---|
| 5,891,453 | A | 4/1999 | Sagel | |
| 6,949,240 | B2 | 9/2005 | Sagel | |
| 7,572,124 | B2 | 8/2009 | Cipolla | |
| 8,241,035 | B2 | 8/2012 | Jones | |
| 8,562,955 | B2 | 10/2013 | Montgomery | |
| 9,726,435 | B2 | 8/2017 | Dahm | |
| 9,752,748 | B2 | 9/2017 | Joergensen | |
| 10,046,173 | B2 | 8/2018 | Newman | |
| 10,512,789 | B2 | 12/2019 | Newman | |
| 11,229,508 | B2 | 1/2022 | Whitney et al. | |
| 2003/0152528 | A1 | 8/2003 | Singh | |
| 2005/0026103 | A1 | 2/2005 | Wasylucha | |
| 2005/0158687 | A1 | 7/2005 | Dahm | |
| 2005/0202363 | A1* | 9/2005 | Osterwalder | A61C 19/066 433/29 |
| 2006/0019214 | A1 | 1/2006 | Lawrence | |
| 2006/0134576 | A1 | 6/2006 | West | |
| 2006/0167531 | A1 | 7/2006 | Gertner et al. | |
| 2007/0003905 | A1* | 1/2007 | Nguyen | A61C 19/003 433/29 |
| 2007/0054233 | A1 | 3/2007 | Rizoiu et al. | |
| 2007/0259310 | A1 | 11/2007 | Goodson | |
| 2008/0063999 | A1 | 3/2008 | Osborn | |
| 2008/0094841 | A1 | 4/2008 | Dahm | |
| 2008/0113313 | A1 | 5/2008 | Khouri | |
| 2010/0151407 | A1 | 6/2010 | Rizoiu | |
| 2010/0220472 | A1 | 9/2010 | Dahm | |
| 2011/0076636 | A1* | 3/2011 | Wolff | A61C 19/063 433/29 |
| 2011/0306004 | A1 | 12/2011 | Sagel | |
| 2013/0027442 | A1 | 1/2013 | Joergensen | |
| 2013/0045457 | A1* | 2/2013 | Chetiar | A61C 19/066 433/29 |
| 2013/0295525 | A1 | 11/2013 | Sagel | |
| 2015/0064645 | A1 | 3/2015 | Jablow | |
| 2015/0140502 | A1 | 5/2015 | Brawn | |
| 2016/0295202 | A1 | 10/2016 | Evans | |
| 2016/0381749 | A1 | 12/2016 | Catalano | |
| 2017/0080249 | A1 | 3/2017 | Brawn et al. | |
| 2017/0197090 | A1* | 7/2017 | Newman | A61C 19/066 |
| 2020/0114165 | A1 | 4/2020 | Bloch et al. | |
| 2020/0230432 | A1* | 7/2020 | Jablow | A61C 19/066 |
| 2020/0261197 | A1 | 8/2020 | Young | |
| 2020/0270791 | A1 | 8/2020 | Liao | |
| 2020/0345472 | A1 | 11/2020 | Chapman et al. | |
| 2021/0038357 | A1 | 2/2021 | Wang | |
| 2021/0244965 | A1 | 8/2021 | Nikinmaa | |
| 2022/0040061 | A1 | 2/2022 | Rajaiah et al. | |
| 2022/0117865 | A1 | 4/2022 | Sagel et al. | |
| 2022/0265409 | A1 | 8/2022 | Cohen et al. | |
| 2023/0000604 | A1 | 1/2023 | Wang | |
| 2023/0009906 | A1 | 1/2023 | Davies-smith et al. | |
| 2023/0139440 | A1 | 5/2023 | Nikinmaa et al. | |
| 2023/0149141 | A1* | 5/2023 | Davies-Smith | A61C 19/066 433/29 |
| 2023/0149275 | A1 | 5/2023 | Rajaiah | |
| 2023/0210453 | A1 | 7/2023 | Brawn et al. | |
| 2023/0263597 | A1 | 8/2023 | Johnson et al. | |

FOREIGN PATENT DOCUMENTS

| | | | |
|---|---|---|---|
| WO | 2004011848 | A2 | 2/2004 |
| WO | 2006065803 | A2 | 6/2006 |
| WO | 2014097053 | A1 | 6/2014 |
| WO | 2020023246 | A1 | 1/2020 |

OTHER PUBLICATIONS

All Office Actions; U.S. Appl. No. 18/675,749, filed May 28, 2024.

All Office Actions; U.S. Appl. No. 18/675,778, filed May 28, 2024.

Mena-Serrano et al., "A Single-Blind Randomized Trial About the Effect of Hydrogen Peroxide Concentration on Light-Activated Bleaching", Operative Dentistry, vol. 41, Issue 5, pp. 455-464.

Torres et al., "Influence of Bleaching Gel Peroxide Concentration on Colorand Penetration through the Tooth Structure" , The Journal of Contemporary Dental Practice, vol. 22, Issue 5 , May 2021, 05 Pages.

Unpublished U.S. Appl. No. 18/675,749, filed May 28, 2024, to Michael David Curtis et al.

Unpublished U.S. Appl. No. 18/675,778, filed May 28, 2024, to Michael David Curtis et al.

* cited by examiner

ORAL CARE DEVICES, KITS, AND METHODS OF USE

TECHNICAL FIELD

The present disclosure relates to oral care devices, kits, and methods of use.

BACKGROUND

A number of approaches can be used to whiten teeth. One common approach is to use chemical whitening actives in a composition to intrinsically and extrinsically whiten teeth. A chemical whitening active is applied to the teeth for a period of time to allow the active ingredient to act upon the teeth to provide an improvement in the whiteness of the teeth. Whiteners are commonly applied to the teeth via toothpastes, rinses, gums, floss, tablets, leave on compositions, strips and trays. Concentration of the whitening active, contact time, and number of applications are some of the primary parameters that dictate the rate and amount of whitening achieved with peroxide-based tooth-whitening compositions.

Devices for whitening teeth are highly prevalent throughout professional and retail markets. A variety of light devices exist to deliver some form of light, typically blue light, to anterior surfaces of some teeth while said teeth are in the presence of peroxide chemistries. The devices are paired with oxidative based chemistries that are applied to the teeth, such as using a product applicator or a strip. Light devices are paired with chemistries using different approaches and, in general, the devices technically differ based on light design features, wavelength, number of light sources, and light intensity output. It would be advantageous to provide a device that balances maximizing the whitening benefit of the treatment with the tolerability and ease of the experience.

SUMMARY OF THE DISCLOSURE

Disclosed herein are oral care light devices, kits, and methods. In an embodiment, an oral care light device includes a housing, a light source positioned in the housing, the light source being capable of emitting electromagnetic radiation comprising one or more wavelengths in a range from about 200 nm to about 1700 nm and an average light intensity of about 150 $mW/cm^2$ or greater, and a battery positioned in the housing, the battery being rechargeable or replaceable. The device may be portable.

In another embodiment, an oral care light device includes a housing structured and configured to be held in a fixed position adjacent to a human jaw during use, a lens comprising an outer surface, a light source capable of emitting electromagnetic radiation comprising one or more wavelengths in a range from about 200 nm to about 1700 nm and an average light intensity of about 150 $mW/cm^2$ or greater, and a battery configured to power the light source. The light source may be configured to increase a temperature of the outer surface of the lens by less than 20° C. after 5 minutes of use.

In another embodiment, an oral care light device includes a housing and a first array of light-emitting diodes (LEDs) disposed in a first plane at a front side of the housing, the first array of LEDs configured to emit electromagnetic radiation of one or more wavelengths in the range from about 200 nm to about 1700 nm and an average light intensity of about 150 $mW/cm^2$ or greater. The first array of LEDs may comprise a central LED positioned at a center of the first array of LEDs.

In an embodiment, a kit includes an oral care light device and a whitening composition. The kit may also include an applicator.

In an embodiment, a method of whitening teeth using an oral care light device includes applying a whitening composition including a bleaching agent to the teeth, and, activating the light source to direct the electromagnetic radiation toward the teeth.

In another embodiment, a method of whitening teeth using an oral care light device comprising a light source, the light source comprising a first array of light-emitting diodes (LEDs), includes applying a whitening composition including a peroxide active to a tooth, maintaining the whitening composition on the tooth for a first time period of greater than 0 seconds to about 120 minutes without activating the light source, and, after the first time period, activating the light source to direct an electromagnetic radiation provided at a wavelength between 200 nm to about 1700 nm toward the tooth for a second time period of greater than 0 seconds to 120 minutes. Each LED of the first array of LEDs may be aligned interproximally.

In another embodiment, a method of applying light to teeth includes directing the light to the teeth for a time period of greater than 0 seconds to 120 minutes, where the light is provided at a wavelength between about 200 nm to about 1700 nm and an average light intensity of about 150 $mW/cm^2$ or greater, where the light raises a temperature of a mouth less than 10° C. when measured at a hottest point of the mouth during the time period.

DETAILED DESCRIPTION

Figure 1:
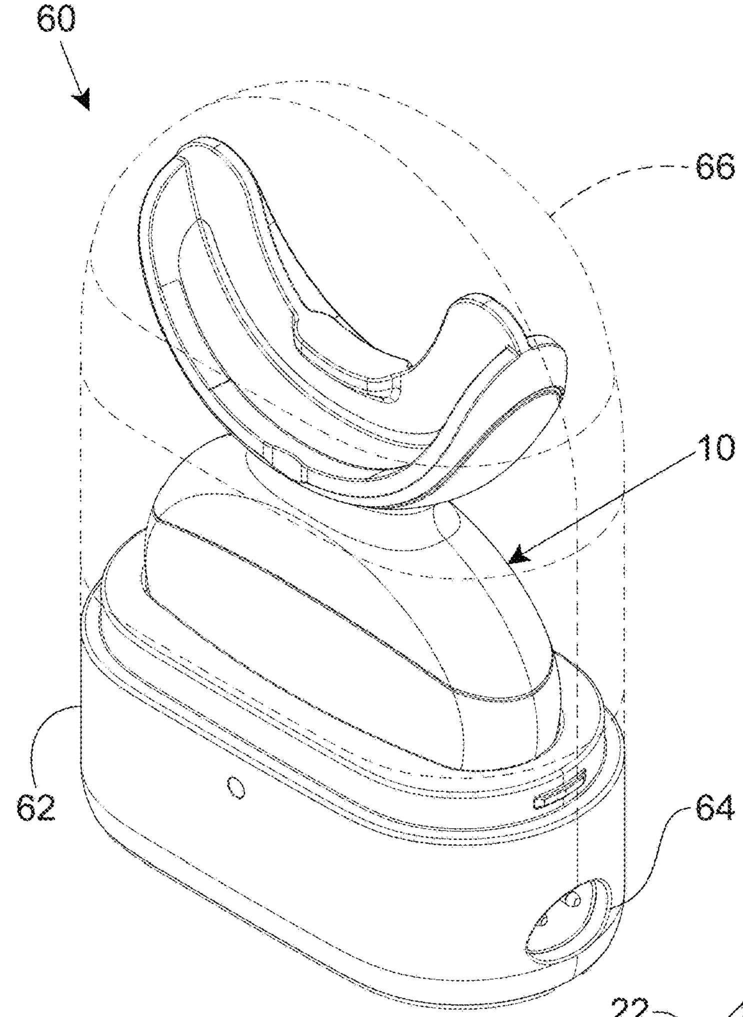
FIG. 1 shows a perspective view of an embodiment of a light system including a light device.
Figure 2:
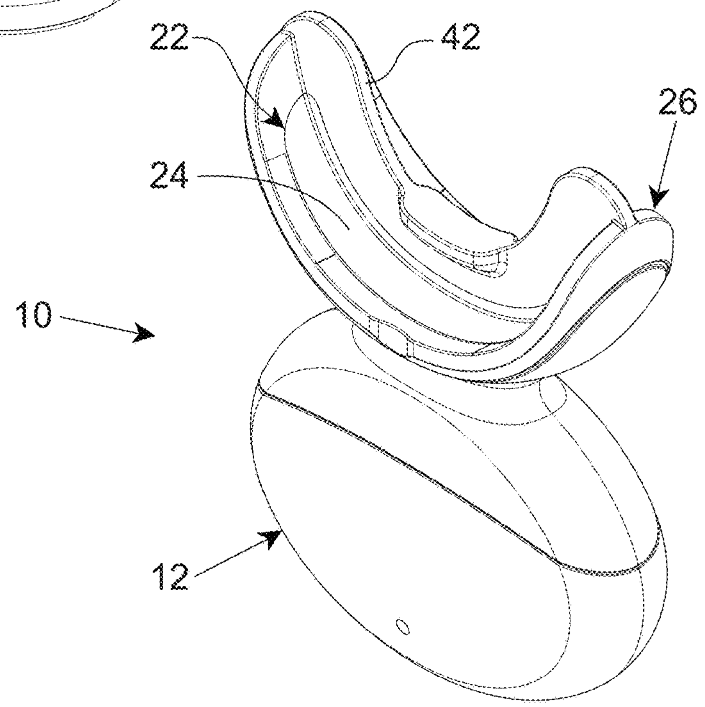
FIG. 2 shows a perspective view of the light device of FIG. 1.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All percentages and ratios used herein after are by weight of total composition (wt %), unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated. All measurements shown in the figures are provided as an example and are not limiting.

As used herein, the term "oral care composition" includes a product that, in the ordinary course of usage, is not intentionally swallowed for purposes of systemic administration of particular therapeutic agents but is rather retained in the oral cavity for a time sufficient to contact dental surfaces or oral tissues. Examples of oral care compositions include dentifrice, toothpaste, tooth gel, subgingival gel, emulsion, mouth rinse, mousse, foam, mouth spray, lozenge, chewable tablet, chewing gum, floss and floss coatings, breath freshening dissolvable strips, denture care or adhesive product, unit-dose composition, and/or fibrous composition. The oral care composition may also be incorporated onto strips or films for direct application or attachment to oral surfaces, such as tooth whitening strips.

As used herein, the term "emulsion" is an example of an oral care composition where: 1) at least one of the phases is discontinuous and 2) at least one of the phases is continuous. Examples of emulsions include droplets of oil dispersed in water. In this example, the water and oil would be mutually immiscible with each other, oil would be the discontinuous phase, and the water would be the continuous phase.

As used herein, the term "bleaching agent" is a component that provides bleaching effects, stain bleaching effects, stain removal effects, stain color change effects, or any other effect, which change or brighten tooth color. Examples include peroxides such as hydrogen peroxide or carbamide peroxide.

As used herein, the term "safe and effective amount" means an amount of a component, high enough to significantly (positively) modify the condition to be treated or to affect the desired whitening result, but low enough to avoid serious side effects (at a reasonable benefit/risk ratio), within the scope of sound medical/dental judgment. The safe and effective amount of a component will vary with the particular condition being treated, the age and physical condition of the patient being treated, the severity of the condition, the duration of treatment, the nature of concurrent therapy, the specific form employed, and the particular vehicle from which the component is applied.

As used herein, the term "a sufficient period of time to achieve whitening" or "a sufficient period of time to achieve the desired effect of the active" means that the composition is used or worn by the participant or the participant is instructed to use or wear the composition from about 1 second to about 24 hours, from about 1 minute to about 12 hours, from about 2 minutes to about 1 hour, or from about 5 minutes to about 30 minutes per application. The treatments may be applied from about 1 to about 7 times a day. The treatments may be applied every day; or daily or weekly for from about 1 day to about 12 months, from about 3 days to about 6 months, from about 7 days to about 3 months, or from about 10 days to about 1 month. The optimal duration and frequency of application may depend on the desired effect, the severity of any condition being treated, the health and age of the user and like considerations.

As used herein, the term "device" means a device that comprises a mouthpiece where, during use, at least a portion of the mouthpiece is a) placed between a lip and a plurality of teeth or b) placed between a buccal surface and a plurality of teeth. Examples of devices include tooth bleaching trays that hold tooth bleaching compositions against teeth and devices that emit light toward a plurality of teeth to enhance tooth bleaching. The mouthpiece or light-emitting portion of the device may be large enough such that during use it can be placed between a lip or buccal surface and a minimum of 4 teeth, preferably between a lip or buccal surface and a minimum of 6 teeth, or most preferably between a lip or buccal surface and a minimum of 8 teeth.

As used herein, the term "light device" means a device comprising a mouthpiece that can emit electromagnetic radiation in at least one wavelength from 200 nm to 1200 nm toward a plurality of teeth. Examples of light devices include devices that emit light toward a plurality of teeth to enhance tooth bleaching.

As used herein, the term "portable device" means a device that a) is no more than 500 grams, b) is not tethered to a power outlet during use, and c) can be freely carried around by the user during use. A portable device can be self-contained or may have a power cord connecting the mouthpiece to an external power supply that is also portable. Examples of portable devices include devices that emit light toward a plurality of teeth to enhance tooth bleaching that have a mouthpiece and a power source built into the same enclosure. Additional examples include devices that emit light toward a plurality of teeth to enhance tooth bleaching that have a mouthpiece connected to an external power source that is also portable.

As used herein, the term "self-contained device" means a device that a) can operate independent of an external power source, power cord, or external hardware equipment, and b) has a longest dimension of less than 15 cm. Examples of self-contained devices include devices that emit light toward a plurality of teeth to enhance tooth bleaching that have a mouthpiece and a power source built into the same enclosure.

TABLE 6 below lists additional examples of portable devices and self-contained devices.

As used herein, the term "whitening boost" means the difference in reduction in yellowness between a composition combined with a light source and the same composition without said light source as measured according to the Clinical Protocol specified herein after the same number of applications and same specified periods of time divided by the reduction in yellowness of the composition without said light source measured according to the Clinical Protocol specified herein after the same number of applications of the same composition for the same periods of time, where the ratio is expressed as a percent. The whitening boost can be represented by the following equation:

$$\text{Whitening Boost (\%)} = \frac{\text{(Reduction in yellowness from Composition + Light} - \text{Reduction in yellowness from Composition without Light)}}{\text{(Reduction in yellowness from Composition without Light)}} \times 100$$

As used herein, the term "device full fit" means that, when worn by a user, the inside surface of the mouthpiece facing the teeth contacts the front incisors or gums that support the incisors.

As used herein, the term "device partial fit" means that, when worn by a user, the inside surface of the mouthpiece facing the teeth does not contact the front incisors or gums that support the incisors but is within 4 mm of the front incisors or gums that support the incisors. As used herein, the term "device arch width" means the width of the arch of the mouthpiece measured between the highest point of inner surface of the outer wall of the first arm and the highest point of the inner surface of the outer wall of the second arm. The first highest point and the second highest point are on a plane, which is orthogonal to the central axis of the mouthpiece, that is spaced a predetermined depth from the outer surface of the lens (see FIG. 20).

Section headings are for convenience of reading and not intended to be limiting.

Acceleration of Whitening with Light

The present disclosure is directed to devices and methods for delivering light having an intensity sufficient to improve whitening of at least one tooth or an array of a human subject's teeth substantially visible during an open-mouthed smile in a form that can be easily self-administered by an individual user.

Blue light with a peak intensity of 450-470 nm has been demonstrated to accelerate tooth whitening when delivered at intensities exceeding 41.5 mW/cm$^2$, 108 mW/cm$^2$, or 134.7 mW/cm$^2$, see commonly assigned U.S. Pat. No. 9,622,840, the entire disclosure of which is incorporated herein by reference.

Light-emitting diodes (LEDs) are familiar to those in the art as exemplary forms of delivery of light such as that used to demonstrate tooth whitening acceleration. It is known to those familiar with the art that the intensity of light delivered by LEDs decreases with the distance from the LED, including such LEDs that are encased in optical plastic to form focusing bulbs or lenses.

Whitening Light Device

It is common for devices designed to provide light incident to anterior teeth surfaces to include features, such as buttresses or trays, which may fit between gums and lips, or between the mandibular and maxillary arches of teeth, to allow said device to be held in constant position without the use of hands. A hand, of course, may be used to install or remove the device, but the intent is for the device to be effectively hands-free in use. For a device to be hands-free and stay in position with minimal discomfort, it preferably must not cause an excessive bending moment to a user's load-bearing oral surfaces where the device is mounted. This bending moment can be minimized by minimizing both a weight and a physical size of the device-especially a distance between the device's center of mass and the user's mouth. To maximize comfort to the user, the weight of the portable device may be, for example, less than about 100 g. A reduction in the device's weight, however, may be in direct contradiction to the device's ability to provide sufficient electrical power, which may be especially true for devices that are portable and self-contained.

Embodiments of the present disclosure may be directed to a portable device. The device may include a rechargeable and/or replaceable power source (e.g., battery). The device may be self-contained or not self-contained. Portable self-contained and portable non-self-contained devices are commercially available. For example, the GLO Brilliant® Advanced White Smile device from GLO Science®, while portable, is not self-contained since it contains a mouthpiece that is tethered via a power cord to a battery pack. This contrasts with the Wireless Whitening Light sold in the Pro Whitening System Plus from Smile Direct Club® that is both portable and self-contained being fully supported by only the mouth during use. The longest dimension of the GLO Brilliant® Advanced White Smile device is over 60 cm, and the longest dimension of the Wireless Whitening Light from Smile Direct Club® is less than 10 cm. In various embodiments, the longest dimension of a self-contained device may be from about 5 cm to about 20 cm, about 6 cm to about 15 cm, about 5 cm to about 10 cm, or about 8 cm to about 10 cm.

The total weight of the device may vary. For example, a portable device may have a total weight from about 5 g to about 500 g, from about 10 g to about 250 g, or from about 20 g to about 100 g. A portable device may have a total weight of no more than about 500 g, no more than about 250 g, or no more than about 100 g. As another example, a self-contained device may have a total weight from about 5 g to about 200 g, from about 10 g to about 100 g, or from about 10 g to about 50 g. A self-contained device may have a total weight of no more than about 200 g, no more than about 100 g, or no more than about 50 g. Portable light devices that are not self-contained generally weigh more than self-contained examples due to the increased weight of the tethered battery pack.

The device may be water-resistant. For example, the device may be rated under the International Electrotechnical Commission (IEC) international standard IEC 60529. The device may have a rating of IPX3, IPX4, IPX5, IPX6, IPX7, IPX8, IPX9, or a combination thereof.

Referring to FIGS. 1-5, in an embodiment, a portable, self-contained light device 10 includes a compact housing 12 and a light source comprising LEDs 14 disposed therein. The light source is configured to direct light to teeth during use. The device 10 may include optional lights that are not directed at teeth during use (e.g., display lights or indicator lights) that are not considered a part of the "light source." The compact housing 12 may be unitary or may include a first housing 16 and a second housing 18 that are separably coupled. A sealing ring 20, such as an O-ring, may be positioned to provide a water-resistant seal between components of the housing 12. The light device 10 can include a lens 22 through which light from the light source passes. The lens 22 has an outer surface 24. In use, the user's teeth may be in contact with or near the outer surface 24 of the lens 22. The LEDs 14 can be adjacent the inner surface of the lens 22, disposed at a suitable distance such as, e.g., from greater than 0 mm to about 5 mm, from greater than 0 to about 3 mm, from greater than 0 to about 1 mm. In the illustrated embodiment, the light device 10 does not include an optic cable or a remote light source. In another embodiment, a light device may include an optic cable or have the light source remote from the mouthpiece.

The light device 10 may include a rim or mouthpiece 26 that can be structured and configured to assist a user in proper positioning of the light device 10 relative to the user's teeth for a desired effect. The mouthpiece 26 may be inserted into a user's mouth in use. The mouthpiece may be flexible or rigid. The mouthpiece 26 defines a central axis 28 extending from a proximal end of the light device 10 to a distal end of the light device 10. The central axis 28 of the mouthpiece 26 may coincide with a central axis of the light device 10. The mouthpiece 26 may include a first arm 30 and a second arm 32 extending on opposite sides of the central axis 28 of the mouthpiece 26. The first and second arms 30, 32 may be symmetrical or may be non-symmetrical. The first and second arms 30, 32 may have an outer wall 34, 36 having an inner surface 38, 40. In use, the user's teeth or gums may be in contact with or near the inner surfaces 38, 40 and the lens 22. The mouthpiece 26 may include a bite bar or bite shelf 42. In an embodiment where the light device 10 is configured to apply light to the upper and lower jaws, the outer walls 34, 36 may extend above and below the bite shelf 42. The bite shelf 42 may extend along the inner surface 38, 40 of the first and second arms 30, 32. In use in such an embodiment, the user's teeth may be in contact with or near the upper and lower surfaces of the bite shelf 42. The user may bite the bite shelf 42 to help keep the device 10 in position during a light treatment. The bite shelf 42 may extend past the outer walls 34, 36 of the first and second arms 30, 32. The bite shelf 42 may include a protrusion that is positioned to fit behind a user's teeth when in use and that may act as a slip guard. Although not shown, the first and second arms 30, 32 may each include an inner wall and a bottom portion extending between the outer walls 34, 36 and inner wall.

The light device 10 can have an electronic unit 44 and a power source, which may include at least one battery 46. The light device 10 can include an electrical circuit 48, supplying power from the power source to the light source. The light device 10 can include one or more manual switches, such as power button 50, that allow a user to activate or deactivate the light source. Any suitable design of the manual switch(es) may be used in the light device 10, such as those disclosed in U.S. Patent Application Pub. No. 2016/0331487, the entire disclosure of which is incorporated herein by reference.

Figure 6:
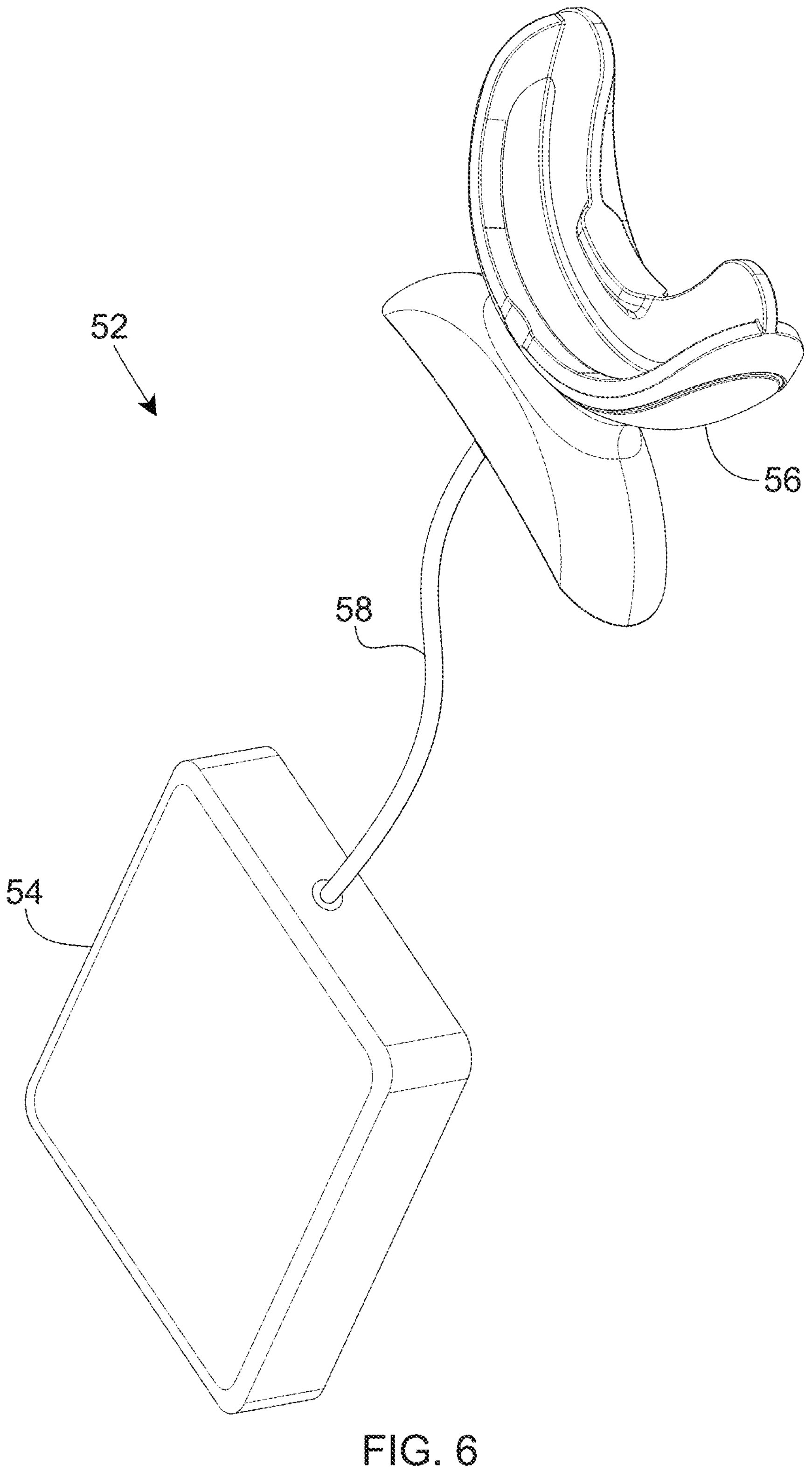
FIG. 6 shows a perspective view of an embodiment of a light device.

The light device 10 is portable and self-contained. Referring to FIG. 6, in an embodiment, a portable but not self-contained light device 52 includes a housing 54 connected to a mouthpiece 56 by a power cord 58. The housing 54 may include an electronic unit and a power source as described herein.

The light device may be part of a light system. For example, as shown in FIG. 1, a light system 60 may include the light device 10 and a stand 62. If the power source is rechargeable, the stand 62 may be configured to charge the power source. The stand may include a port 64 for a power cord (not shown). The light system 100 may also include a cover 66.

In various embodiments, the light device may be configured to be in wireless communication with another device, such as a personal care device or a computer device (e.g., a smart phone). The wireless communication may be based upon a suitable short range radio frequency communication technology, such as Bluetooth, WiFi, or another type of radio frequency link, such as wireless USB at 2.4 GHz. Other wireless data communication technologies may be used such as, for example, radio frequency transmission, infrared (IR) transmissions, Li-Fi, or cellular transmission. Data transfer can be one-way and/or two-way, continuous and/or intermittent, modulated, or any combination of the foregoing.

Power Source

The choice of power source can have implications on device size, shape, weight, number of uses, total device lifetime, and device safety. The power source may include one or more battery cells (such as battery 46), which may be a primary cell or a rechargeable secondary cell. Suitable batteries for rechargeable devices include lithium ion, lithium polymer, and nickel metal hydride among others. One battery or more than one battery could be used to meet the power supply requirements of a device with an average light intensity output of about 150 $mW/cm^2$ or greater as measured based on the Procedure to Measure Intensity of Electromagnetic Radiation. Using more than one battery may increase the device size and weight.

Where the device is portable and rechargeable, the battery may be a rechargeable single battery, relatively small, and capable of meeting the light intensity output over a minimum number of uses before recharging with a minimum shelf life. A rechargeable battery may be configured to supply more than one use, such as three, four, five, six, seven, or more than seven uses, based on a single full charge (e.g., prior to being recharged) independent of battery age. For example, the rechargeable battery may be configured to supply more than seven 5-minute uses based on a single full charge independent of battery age.

Figure 3:
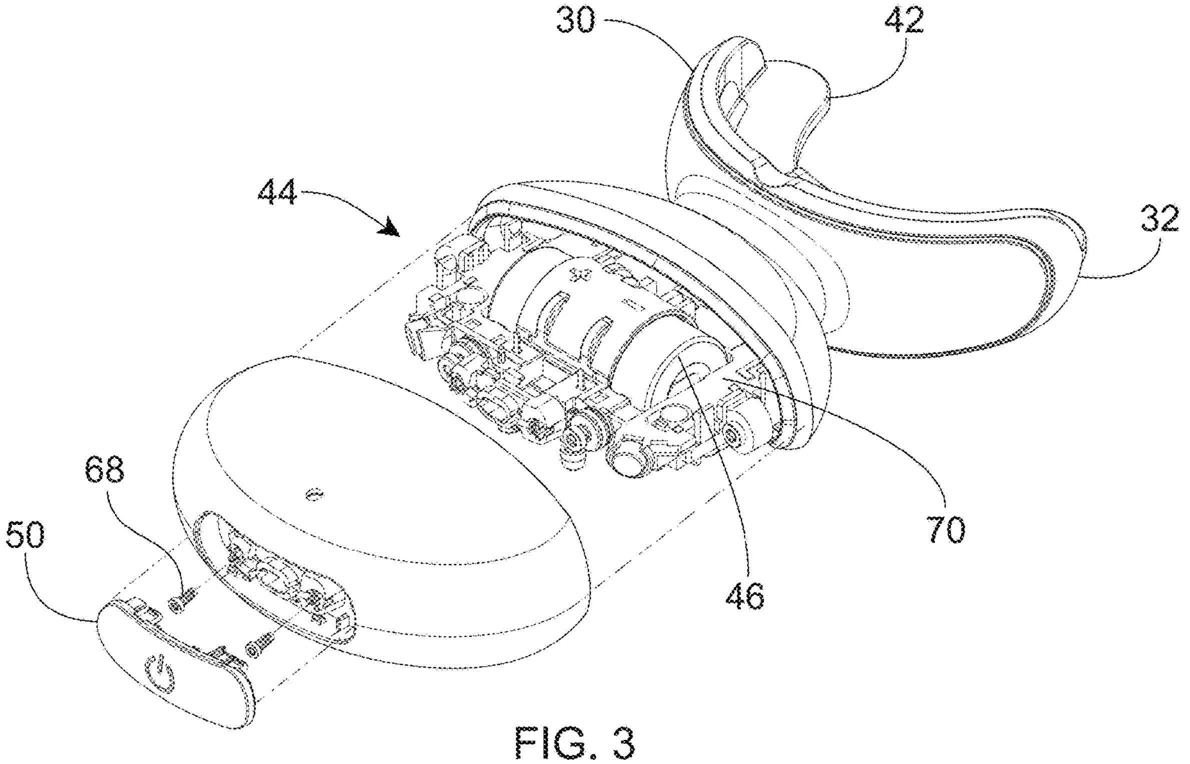
FIG. 3 shows a partially exploded perspective view of the light device of FIG. 1.
Figure 4:
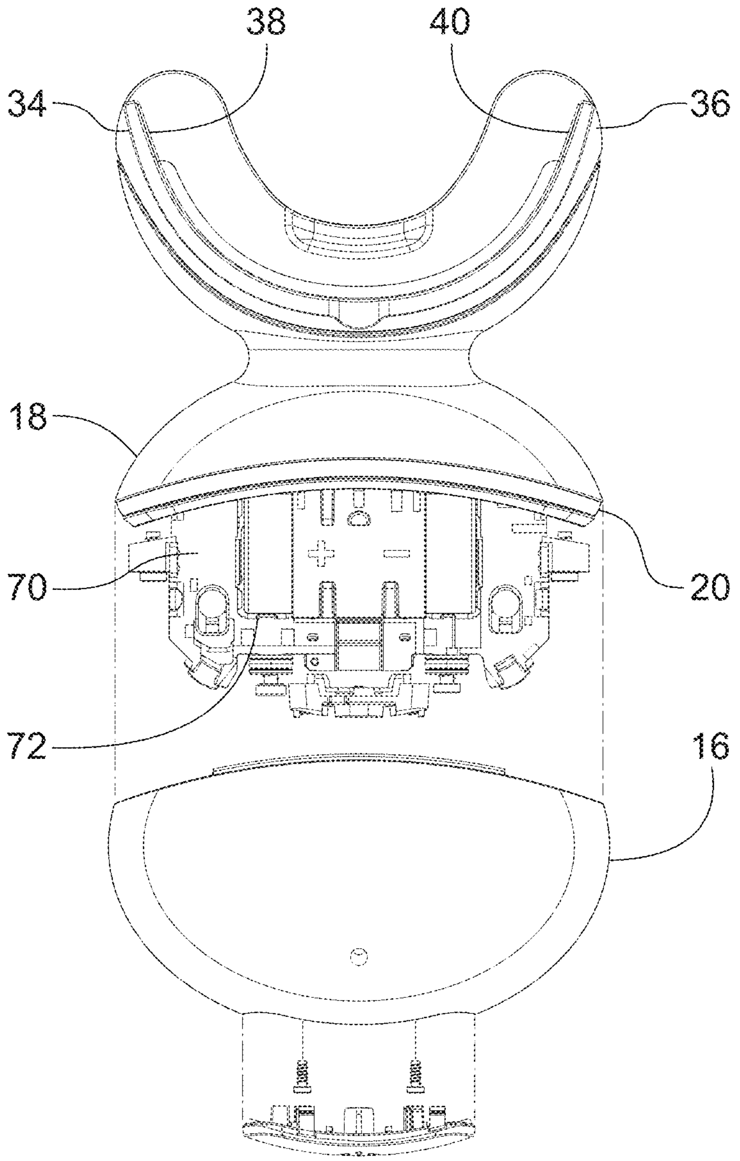
FIG. 4 shows a partially exploded top view of the light device of FIG. 1.
Figure 5:
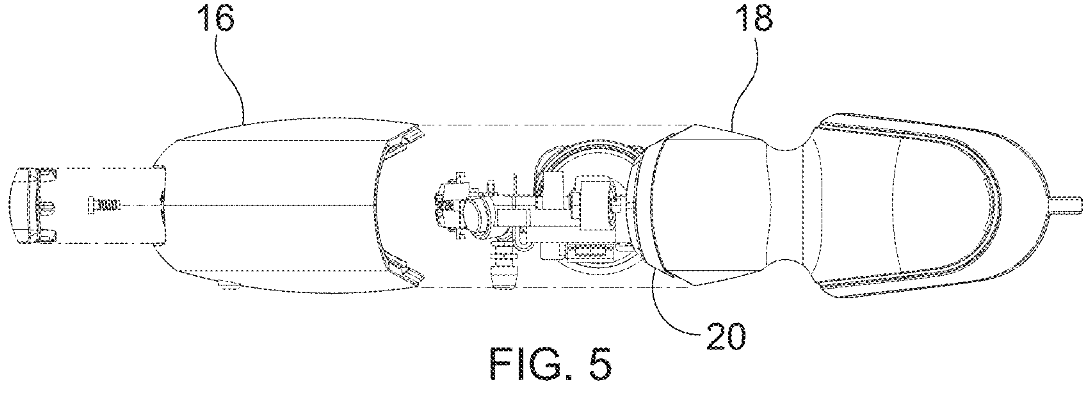
FIG. 5 shows a partially exploded side view of the light device of FIG. 1.

The battery can be permanently positioned in the device (e.g., a user would have to break the housing to access the battery). Alternatively, the battery can be replaceable, which may extend the device lifetime. The battery may be replaceable by a trained technician or, more preferably, the battery can be replaced by a user. For example, the battery may be removable and replaceable by the end-user or by an independent operator during the lifetime of the device, if the battery has a shorter lifetime than the device, or at the latest at the end of the lifetime of the device. The battery can be readily replaceable where, after its removal from the device, it can be substituted by a similar battery without affecting the functioning or the performance of the device. Where the battery is replaceable, the device may be configured to maintain water resistant certification after battery replacement. For example, as shown in FIGS. 3-5, the first housing 16 and the second housing 18 may be separated to allow access to the battery 46. In an example embodiment, the cover of the power button 50 may be removed to expose one or more fasteners, such as screws 68, that separably couple the first and second housings 16, 18. Removing the screws 68 allows for the user to separate the first and second housings 16, 18 and access the battery 46. In such an embodiment, the portable rechargeable device with an intensity of about 150 mW/cm$^2$ or greater is water resistant with a replaceable battery.

Printed Circuit Board

Referring to FIGS. 3-5, the device 10 may include a printed circuit board (PCB) such as the PCB 70. The electrical design, size, and shape of the device may depend in part on the PCB. The complexity of the PCB can lead to a larger PCB size and a larger device size. The PCB 70 may be multi-layered and include a cutout 72, which may be in an interior of the PCB 70. In an embodiment, the battery 46 may be positioned in the cutout 72 of the PCB 70. The PCB may include, for example, one layer, more than one layer, two layers, three layers, four layers, five layers, six layers, or more than six layers. Surprisingly, using a multi-layer PCB design with a cutout to house a battery allows for a reduced PCB size without compromising functionality. The PCB may have a maximum width, for example, in a range of about 35 mm to about 55 mm, or about 40 mm to about 50 mm, or may be about 45 mm. The PCB may have a maximum depth, for example, in a range of about 20 mm to about 50 mm, or about 30 mm to about 40 mm, or may be about 40 mm. The cutout may have a maximum width, for example, in a range of about 20 mm to about 40 mm, or about 25 mm to about 35 mm, or may be about 30 mm. The cutout may have a maximum depth, for example, in a range of about 5 mm to about 25 mm, or about 10 mm to about 20 mm, or may be about 16 mm.

Light Intensity and Wavelength

In a device where the light source is adjacent the teeth (e.g., not using a fiber optic cable), the resulting light intensity to which the teeth are exposed, i.e., the light intensity at the surface of the teeth, will depend primarily on the distance of the light source from the teeth and the energy output of the light source. The LEDs 14 can be disposed at a suitable distance from the teeth during use, e.g., from about 0.5 mm and about 10 mm or from about 0.5 mm to about 4 mm. In various embodiments, the average light intensity measured according to the procedure specified herein can be from about 10 mW/cm$^2$ to about 1,000 mW/cm$^2$, from about 50 mW/cm$^2$ to about 500 mW/cm$^2$, from about 150 mW/cm$^2$ to about 500 mW/cm$^2$, or from about 150 mW/cm$^2$ to about 300 mW/cm$^2$. The average light intensity can be about 150 mW/cm$^2$ or greater or at least 200 mW/cm$^2$.

The light emitted by the LEDs 14 may be selected to provide electromagnetic radiation at a wavelength that is most absorbed by the tooth stains. The electromagnetic radiation may be selected to be at a wavelength corresponding to a light color diametrically opposite the stain color, as identified for example on the 1976 CIE LAB color scale. Utilization of a diametrically opposite light color increases absorption of the light by the stain. Yellow stains, as commonly present on teeth to be whitened, may better absorb blue light (about 380 nm to about 520 nm). Thus, the light source may be selected to provide electromagnetic radiation at a wavelength of about 200 nm to about 1700 nm, about 400 nm to about 520 nm, or about 440 nm to about 490 nm, or an average wavelength of about 440 nm, or about 450 nm, or about 460 nm, or about 470 nm, or about 480 nm, or about 490 nm. Green stains, on the other hand, may better absorb red light, such as light having a wavelength of about 600 nm to about 780 nm. A light source for use in whitening green stains may be selected to provide electromagnetic radiation at a wavelength of about 600 nm to about 780 nm, or about 680 nm to about 720 nm, or an average wavelength of about 680 nm, or about 690 nm, or about 700 nm, or about 710 nm, or about 720 nm. In one embodiment, the light emitted by the LEDs during the process can have a frequency of from about 350 nm to about 470 nm. The light may be emitted at more than one wavelength. The wavelength of the emitted light may vary during use.

Heat Output

Heat is often a byproduct of light especially high intensity light output. Heat can be seen as either advantageous or deleterious to the whitening process. Heat can increase the tooth bleaching rate, while too much heat could pose hazardous to either hard or soft tissues in the mouth. The few commercially available whitening lights with average light intensities of about 150 mW/cm$^2$ or greater may generate significant associated heat as a byproduct of the high light intensities. For example, many of these lights place the light source remote from the teeth and use a fiber optic cable or light guides to transmit the light to manage tooth heat exposure. Heat may accelerate the whitening chemical reaction and is a desired aspect of some conventional lights (e.g., GLO Brilliant® Advanced White Smile device).

Further, whitening lights with light intensities of about 150 mW/cm$^2$ or greater have high power supply and battery requirements to emit the high intensity light to a minimum number of teeth over a minimum wear time. Philips Zoom! and Britesmile®, for example, provide high power, high intensity (e.g., about 150 mW/cm$^2$ or greater) light delivery systems to dental professionals for use with expert applied, high concentration peroxide (i.e., about 15% or greater) chemistries, such as carbamide peroxide and hydrogen peroxide. These lights have limitations including lack of portability and comfort, requisite operator's skill, and inflexible power requirements with a time-consuming process. More specifically, such systems are typically large, floor-standing or floor-mounted appliances, that are designed to be operated exclusively by trained dental professionals. These systems are inherently larger as the light source(s) is remote from the teeth and mouthpiece, for example, using an optic cable, or is recessed into an external lamp. Finally, these systems need to be powered directly from a wall outlet, such as a 110 VAC outlet (which essentially tethers them to the wall), as opposed to batteries based on the power required to generate high light intensity over the defined whitening usage periods.

The closer a light source is to the teeth, the higher the light intensity the tooth will realize. However, placing a light source close to the teeth presents the risk of also exposing the teeth and soft tissue to excessive heat. One known way to overcome light intensity loss as a light source is moved away from the target tooth surface is to transmit the light source through a fiber optic cable to the tooth. While this approach is efficient at transmitting light without appreciable intensity loss and reducing heat, it requires a larger light device with a cable tethered to a remote light source, which can be cumbersome for a user to manage. In addition, light arrays or guides are commonly required in the light mouthpiece to broadcast the light from the fiber optic cable onto the intended teeth (e.g., the "smile teeth"). These light devices are often powered from a 110 VAC power source, which limits their portability.

Surprisingly, light devices with high intensity output according to embodiments of the present disclosure can effectively manage the generated heat to support the safe use of the light under instructed and possible misuse conditions. For example, a light device may include a minimum number of LEDs arranged to provide maximum tooth coverage at a minimum average light intensity. As another example, a light device may include a sleep timer after a period of use. Surprisingly, these heat management techniques can allow for a portable, self-contained, rechargeable light device that provides light with an average light intensity output of about 150 mW/cm$^2$ or greater. The heat management techniques may be used alone or in combination and are discussed further below.

Light Source Configurations

Figure 10:
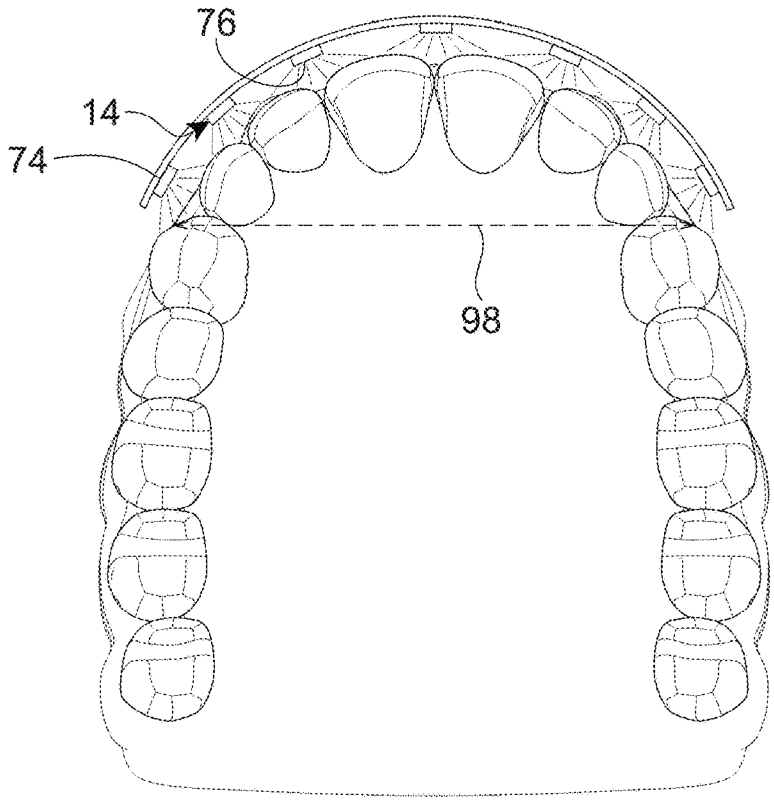
FIG. 10 is a schematic showing an array of light-emitting diodes ("LEDs") interproximally positioned adjacent maxillary teeth of a human jaw.
Figure 11:
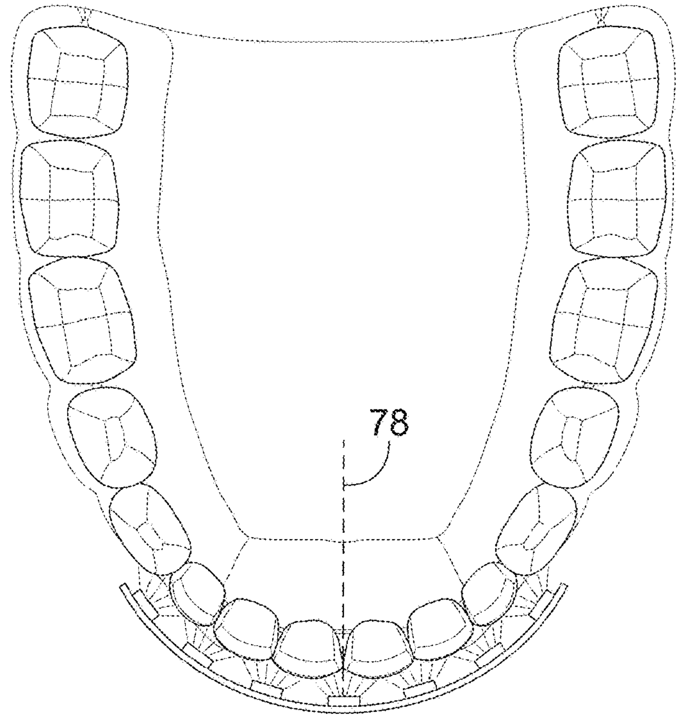
FIG. 11 is a schematic showing an array of LEDs interproximally positioned adjacent mandibular teeth of a human jaw.

Individual LEDs 14 include a power-connection end 74 and a light-emitting end 76 (see FIGS. 10 and 11). The power-connection end 76 may comprise power-connection leads (not shown) through which an electrical current can be driven. The LEDs 14 may be surface-mounted diodes (e.g., "flat" LEDs) or bulb LEDs. The light-emitting end 76 may be, for example, flat (FIG. 10), spherical, or ellipsoidal. The luminous intensity of light-emitting diodes is typically measured in Luminous Flux (Im) and Luminous Intensity (cd). The light-emitting end 76 of each LED 14 can emit at least about 8.0 Im of light when at least about 150 mA of electrical current is applied through the power-connection leads at the power-connection end 74. Example LEDs include, without limitation, Broadcom® ASMW-LG00 & Broadcom® ASMW-LM00. The LEDs 14 can be driven at high current and may be able to dissipate the heat efficiently resulting in better performance with higher reliability. The size of the LEDs 14 may vary. For example, the LED 14 may have a length of about 3 mm and a height of about 1.5 mm.

Figure 15:
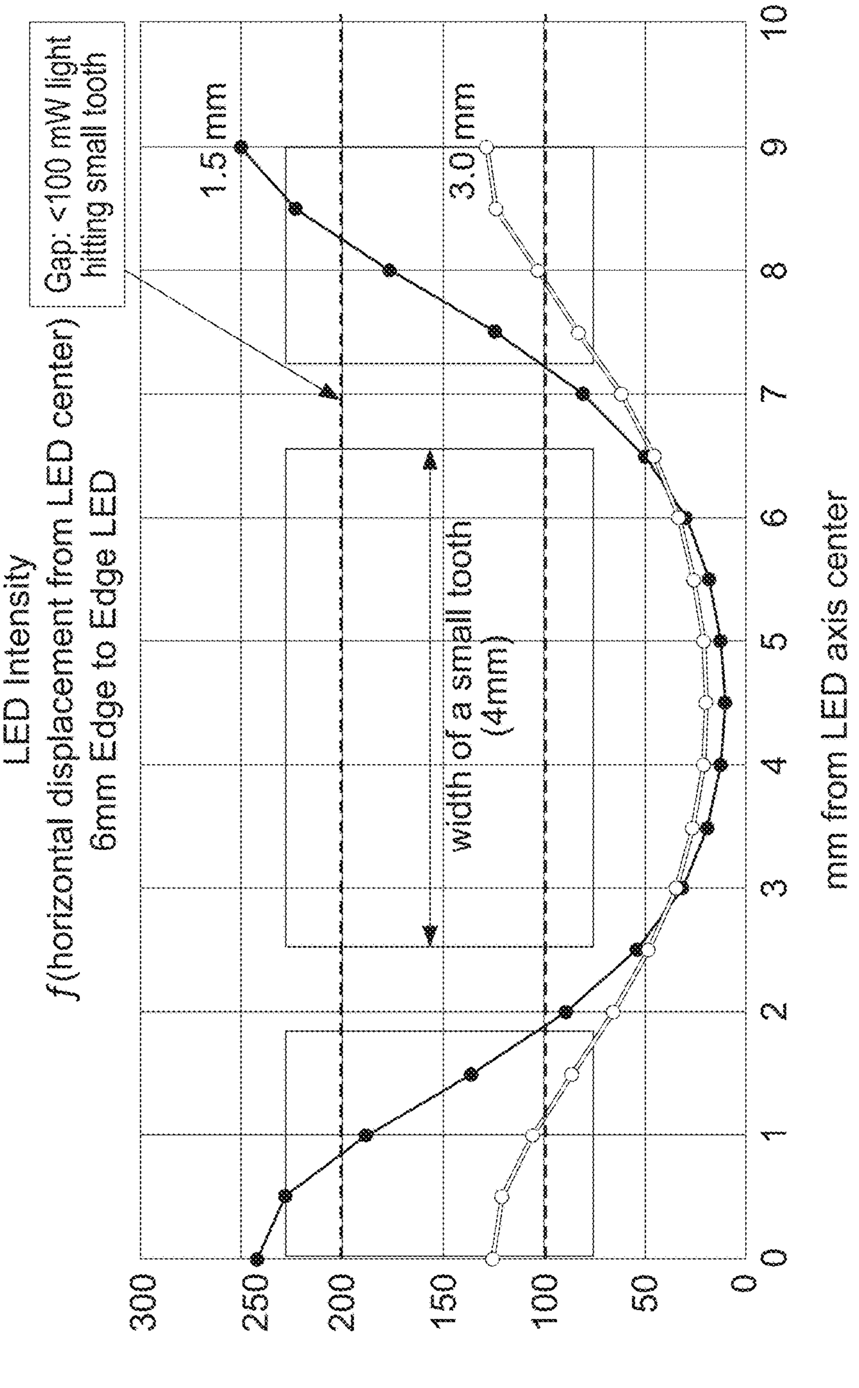
FIG. 15 is a graph representing the LED Intensity along a distance from the LED axis center at two distances from the light-emitting end of the LED.
Figure 16:
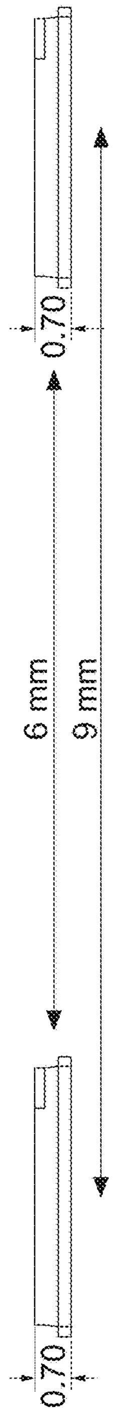
FIG. 16 is a schematic showing LEDs having a spacing that may produce the LED Intensity shown in FIG. 15.

Each LED 14 has an axis of primary focus 78, defined herein as an axis along which the LED-emitted light has the highest intensity. The light intensity gradually decreases radially away from the axis of primary focus 78 (see FIG. 15). The axis along which the LED-emitted light has the highest intensity may correspond to a maximum amount of heat generation. The heat generation may also gradually decrease radially away from the axis of primary focus 78. In an embodiment of the LED 14 shown in FIG. 11, the axis of primary focus 78 of the LED 14 coincides substantially with a center of the front surface of the LED 14.

An array of LEDs 14 can be arranged such that all LED axes of primary focus 78 lie substantially in a single plane. Naturally, the focal point or points of the axes of primary focus 78 of the array of LEDs will also lie in the same plane. Alternatively, the LEDs 14 may lie in different planes, in which instance the axes of primary focus 78 of the LEDs may form an included angle there between. An array may include two outer LEDs 14*a* and a plurality of inner LEDs 14*b*, which may include a central LED. An array of LEDs may be configured to create a light plane that emits a minimum average light intensity of about 150 mW/cm$^2$ or greater.

The LED 14 may be configured to provide a maximum temperature increase as measured at the center of the LED 14 during a defined period of use. The temperature of the outer surface of the lens may be measured. For example, the LED may be configured to provide a maximum temperature increase from about 1° C. to about 20° C., from about 1° C. to about 10° C.; or no more than about 20° C., no more than about 10° C. as measured according to the procedure specified herein at 0 mm from the outer surface (i.e., on the outer surface) of the lens at the center of the LED during a defined time period of about 5 minutes. For another example, the light source may be configured to provide a maximum temperature increase of the outer surface of the lens in a range of from about 1° C. to about 20° C., in a range of from about 1° C. to about 10° C., of no more than about 10° C., of no more than about 8° C., or of no more than about 5° C. as measured according to the procedure specified herein at 0 mm from the outer surface (i.e., on the outer surface) of the lens at the center of the LED during a defined time period of about 2 minutes. For another example, the light source may be configured to provide a maximum temperature increase of the outer surface of the lens in a range of from about 1° C. to about 20° C., in a range of from about 1° C. to about 10° C., of less than about 10° C., of less than about 6° C., or of less than about 5° C. as measured according to the procedure specified herein at 0 mm from the outer surface (i.e., on the outer surface) of the lens at the center of the LED during a defined time period of about 1 minute.

Additionally or alternatively, the temperature of the air may be measured at a distance from the outer surface of the lens. For example, the LED may be configured to provide a maximum temperature increase from about 1° C. to about 20° C., from about 1° C. to about 10° C.; or no more than about 20° C., no more than about 10° C. as measured according to the procedure specified herein at 1 mm from the outer surface of the lens at the center of the LED during a defined time period of about 5 minutes.

An LED 14 may have a ratio of an average light intensity output to a temperature increase of the outer surface of the lens as measured on its surface at the center of the LED in a range of about 15 mW/cm$^2$/° C. to about 100 mW/cm$^2$/° C., about 25 mW/cm$^2$/° C. to about 100 mW/cm$^2$/° C. The ratio may be greater than about 15 mW/cm$^2$/° C., greater than about 20 mW/cm$^2$/° C., or greater than about 25 mW/cm$^2$/° C. An LED 14 may have a ratio of an average light intensity output to a temperature increase of air as measured 1.0 mm from the outer surface of the lens at the center of the LED in a range of about 15 mW/cm$^2$/° C. to about 100 mW/cm$^2$/° C., about 25 mW/cm$^2$/° C. to about 100 mW/cm$^2$/° C. The ratio may be greater than about 12 mW/cm$^2$/° C., greater than about 15 mW/cm$^2$/° C., or greater than about 18 mW/cm$^2$/° C.

The light device may impart some heat to the teeth and/or mouth during use. The light source may be configured to provide minimal to low heat transfer both the teeth and the mouth during a defined period of use. For example, for a wear time of 10 minutes, the light source may be configured to provide a temperature increase to the teeth or mouth of no more than about 10° C., no more than about 6° C., or no more than about 3° C. For a wear time of 5 minutes, in some embodiments, the light source may be configured to provide a temperature increase to the teeth or mouth of no more than about 10° C., no more than about 5° C., or no more than about 2° C.

The transparency or translucency of the lens may affect the temperature increase of the lens surface due to adsorption of light emitted from the LED. The lens may be transparent or translucent to electromagnetic radiation with wavelengths from about 200 nm to about 1700 nm. In certain embodiments, the lens allows from about 10% to about 100%, about 20% to about 100%, about 40% to about 100%, or about 50% to about 90% of electromagnetic radiation from about 400 nm to about 500 nm to pass through.

The LEDs 14 may be positioned to be aligned between two adjacent teeth (i.e., interproximally) when the light device 10 is used. Interproximal spaces in between teeth often collect and exhibit the highest stain level since they are hardest to reach during brushing or even some tooth whitening processes. Surprisingly, we have found both staining on facial tooth surfaces and interproximal spaces are the primary tooth areas that define the perception of attractive smiles. By positioning the LEDs between teeth, the hardest-to-remove interproximal stains are targeted with higher intensity light as compared to conventional approaches where the LED is centered on the tooth. In other words, the light source may be configured to emit a higher light intensity to the interproximal area between two teeth rather than a facial surface of the tooth. This may provide a more even and more attractive whitening appearance of the teeth as the hardest area to whiten is targeted while the flat area receives comparable benefit from the LED broadcast intensity.

When an LED 14 is aligned interproximally, it will emit light towards the air gap between the two adjacent teeth. The air gap will receive the maximum amount of heat from the LED 14 (i.e., the heat generation may be strongest at a center of the LED 14). The air gap dissipates some of the heat that would otherwise be directed at the tooth. The light emitted from the LED 14 will be received by each of the adjacent teeth. In such a configuration, an array may include a central LED. The central LED may be positioned substantially at the center of the array. The central LED may be aligned interproximally of a subject's two front teeth when in use. The light device 10 may have an equal number of LEDs 14 on opposing sides of the central LED 14. Where "n" number of teeth are intended to receive light, an array having LEDs aligned interproximally may have "n−1" number of LEDs 14. The example embodiment shown in FIGS. 7-9 includes two outer LEDs 14*a* and five inner LEDs 14*b*. In such a configuration, eight teeth will receive light from the seven LEDs 14. The outermost teeth will receive light from one of the outer LEDs 14*a*, while the inner teeth will receive light from two LEDs 14.

As long as light illuminates some part of a tooth, the light may refract through the tooth. In other words, light may not need to directly illuminate an area of the tooth for that area to receive a whitening benefit. However, the light may not transfer to a neighboring tooth that is not illuminated. Conventional whitening lights contain dedicated light sources centered on each intended tooth to be whitened. While effective at lower light intensities, this approach increases the heat generation per tooth and/or power requirements of a light device with intensities of about 150 mW/cm$^2$ or greater over a minimum wear time and number of uses between recharging. Interproximal spacing of the LEDs 14 surprisingly reduces overall heat generation, heat exposure of each targeted tooth due at least in part to the heat dissipation provided by the air gap, and/or power supply requirements.

Surprisingly, an additional heat dissipating advantage of placing light sources so that they are positioned between teeth rather than centered directly on the teeth during use relates to heat transfer propensity to the tooth. More facile direct heat transfer can occur to the tooth when the light source is centered on the flat surface of the tooth as compared to the heat dissipating air space that exists between teeth. As illustrated in FIGS. 10 and 11, the center of the LED 14, which may correspond to the highest intensity and heat generation, can be positioned in front of an air space instead of being positioned directly in front of or on the flat tooth surface where heat transfer occurs more readily.

The spacing between LEDs 14 (or other discrete light sources) may vary to account for anatomical geometrical variability of teeth and mouth sizes. The spacing between LEDs 14 may be defined by an edge-to-edge distance based on a broadcast angle defined at a light source distance to the tooth surface. In use, the distance of the light source to the tooth surface may be in a range of from about 0.5 mm to about 5 mm, about 1 mm to about 3 mm, or about 1 mm to about 2 mm, or may be about 1.5 mm or about 3 mm. The edge-to-edge spacing may vary based on the flat printed circuit board LED arrangement (see FIG. 14), the average width of the smallest target tooth (e.g., upper or lower tooth), and the light source broadcast angle. The edge-to-edge spacing may be in a range of about 1 mm to about 7 mm, about 1 mm to about 3 mm, or about 4 mm to about 7 mm, or may be about 2, 3, 4, 5, or 6.5 mm.

If the light source includes more than one array of LEDs 14, the spacing between LEDs 14 in each array may be the same or may vary. An upper array may have an edge-to-edge spacing in a range of about 3 mm to about 7 mm, about 4 mm to about 7 mm, about 5 mm to about 7 mm, or about 5.5 to about 6.5 mm, or may be about 4, 5, or 6.5 mm. An lower array may have an edge-to-edge spacing in a range of from about 1 mm to about 5 mm, about 1 mm to about 4 mm, about 1 mm to about 3 mm, or about 1 mm to about 2 mm, or can be about 2, 3, or 4 mm. In this arrangement under the defined conditions, the outermost upper and lower targeted teeth will experience light from a single light source (i.e., the outermost LED) and all inner targeted upper and lower teeth will experience a minimum light intensity from two LEDs 14 per tooth. Additionally, a targeted tooth will be not missed all together, which is possible in light source arrangements when lights sources are separated by about 5 mm or greater on the lower teeth (e.g., in light devices where the spacing is the same for upper and lower teeth).

Figure 7:
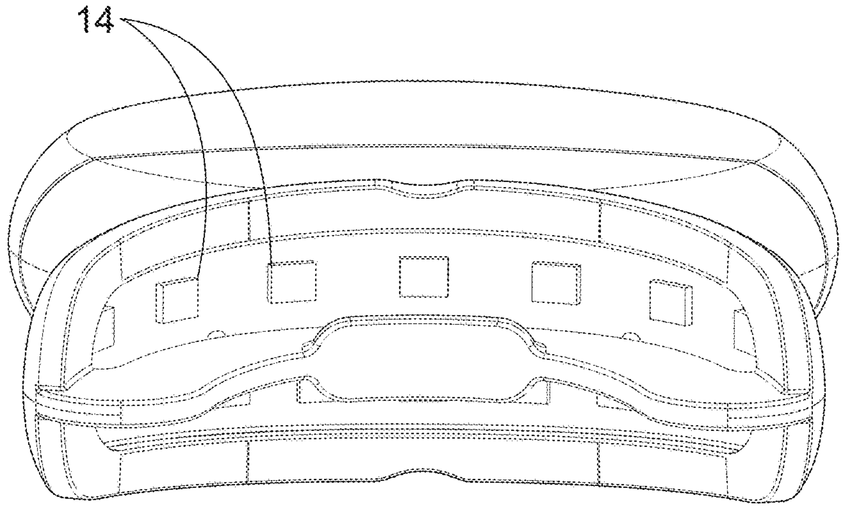
FIG. 7 shows a perspective view from above of the front of the light device of FIG. 1 with the lens removed.
Figure 8:
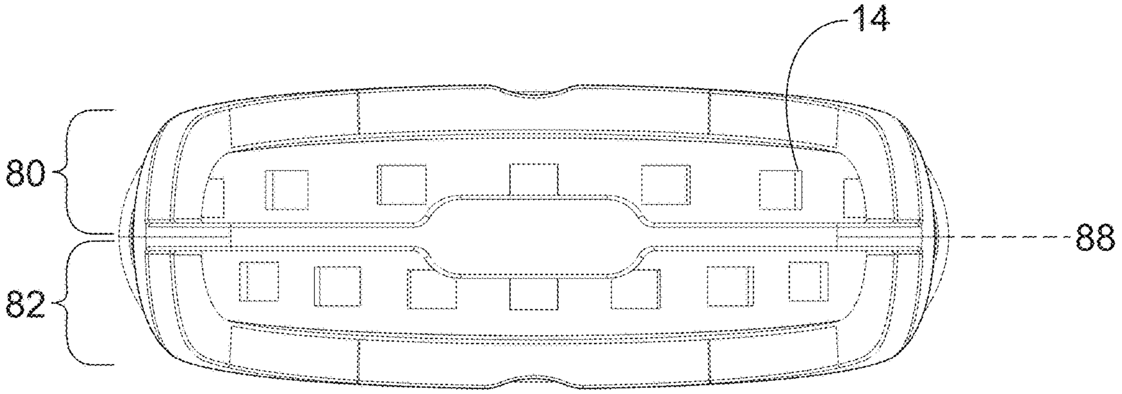
FIG. 8 shows a front view of the light device of FIG. 1 with the lens removed.
Figure 9:
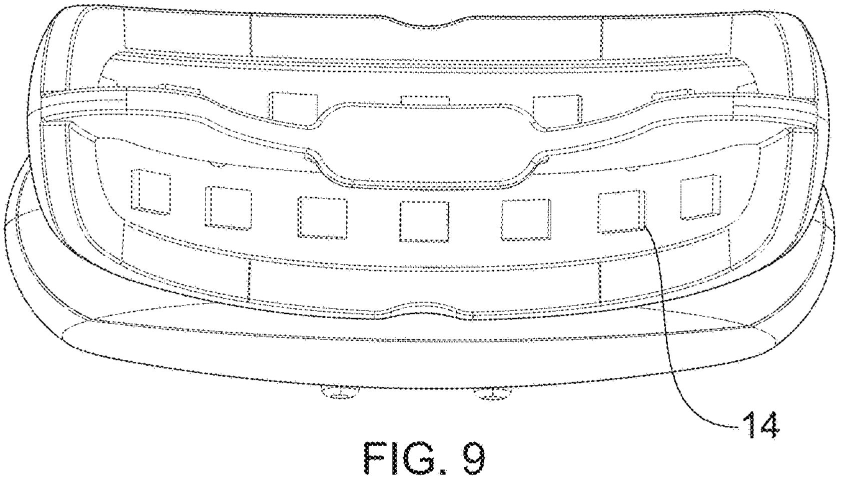
FIG. 9 shows a perspective view from below of the front of the light device of FIG. 1 with the lens removed.

If the light source includes more than one array of LEDs 14, the arrays may be arranged either in parallel to one another or otherwise, as is explained herein below. With reference to FIGS. 7-9, the light device 10 may include a first array 80 of LEDs 14 and a second array 82 of LEDs 14 adjacent to the first array 80. The first and second arrays 80, 82 can be upper and lower arrays, respectively. The first and second arrays 80, 82 may each be disposed at a front side of the housing 12 and may be arranged to deliver blue visible light or near-visible UV light to substantially all anterior surfaces of anterior maxillary teeth or anterior mandibular teeth of the human jaw.

Figure 12:
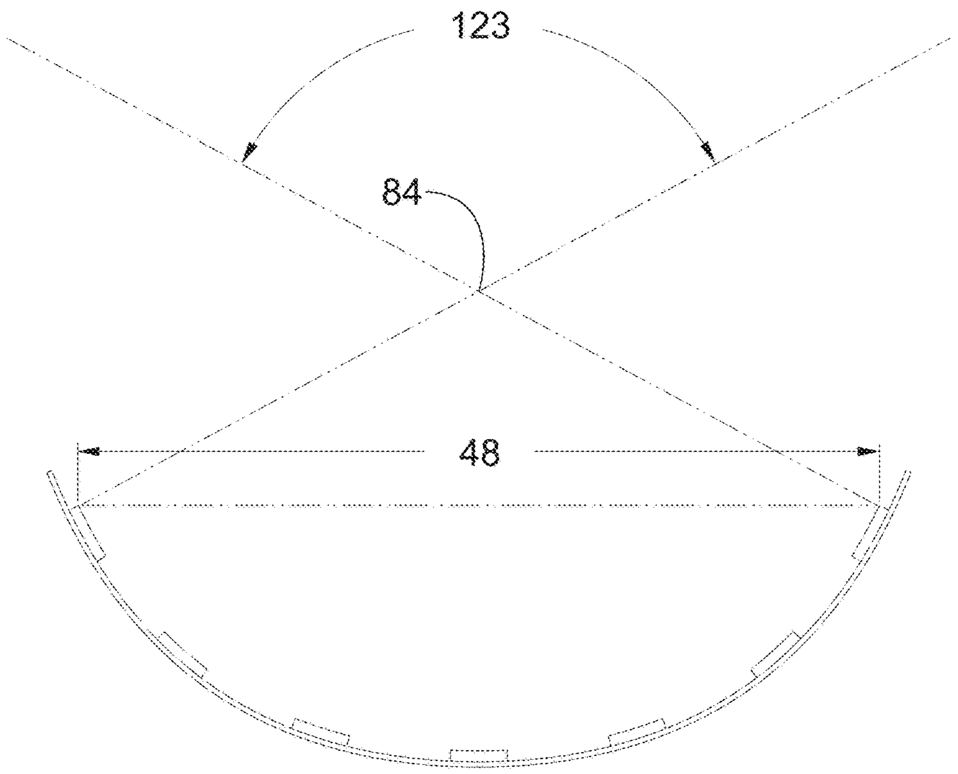
FIG. 12 is a schematic showing of a focal point of an upper array of LEDs according to an embodiment.
Figure 13:
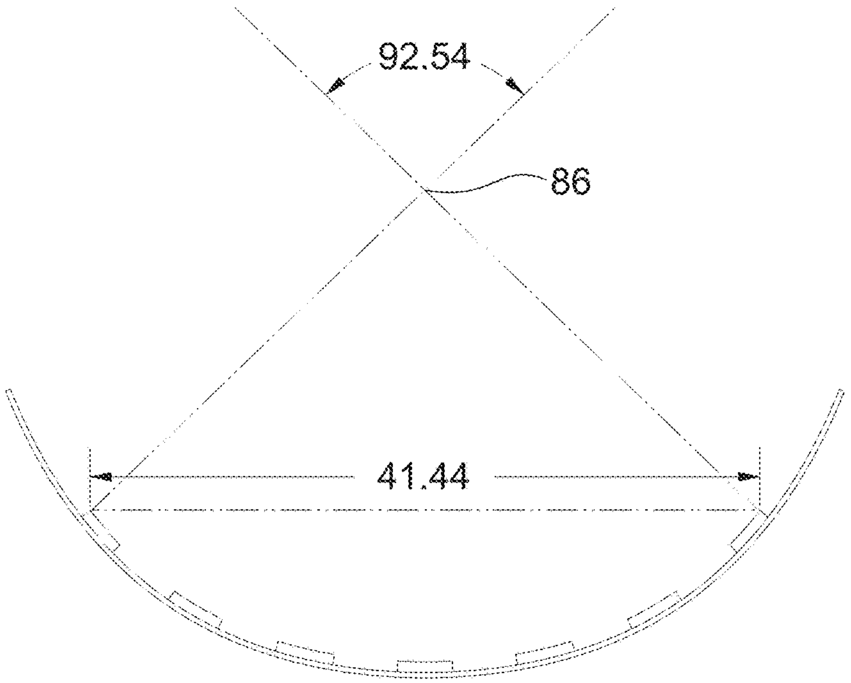
FIG. 13 is a schematic showing of a focal point of a lower array of LEDs according to an embodiment.

The horizontal axis of the LEDs may be parallel (see FIG. 8) or non-parallel to the central horizontal axis 88 of the mouthpiece 56 (e.g., which may be parallel with the bite shelf 42). Further, the vertical axis of the LEDs may be perpendicular (see FIG. 8) or not perpendicular with a central horizontal plane of the front of the mouthpiece 56 (e.g., in which the bite shelf 42 may be located). The axes of primary focus 78 of the upper and lower LEDs 14 form two distinct focal points: an upper-arc focal point 84, formed by the axes of primary focus 78 of the LEDs 14 in the upper array, and a lower-arc focal point 86, formed by the axes of primary focus 78 of the LEDs 14 in the lower array. As shown in FIGS. 12 and 13, both focal points 84, 86 exist externally relative to the light device 10. A distance from the upper array focal point 86 and any LED's light-emitting tip 22 may be different from the distance from the lower array focal point 84 and any LED's light-emitting tip 22. For example, the lower array focal point 84 (shown in FIG. 13) may be further away from the light device 10 than the upper array focal point 86 (shown in FIG. 12).

Each array of LEDs may include any suitable, either even or odd, number of LEDs 14, e.g., three, four, five, six, seven, eight, nine, ten, eleven or more LEDs altogether. For example, from one to nine LEDs may comprise the inner LEDs 14*b*, and two LEDs may comprise the outer LEDs 14*a*. The example light device 10 illustrated herein includes two outer LEDs 14*a* and five inner LEDs 14*b* in each array 80, 82. One skilled in the art will appreciate that other suitable configurations of the light device 10, comprising different numbers of inner LEDs 14*b* in each array can be had and are fully contemplated.

Figure 14:
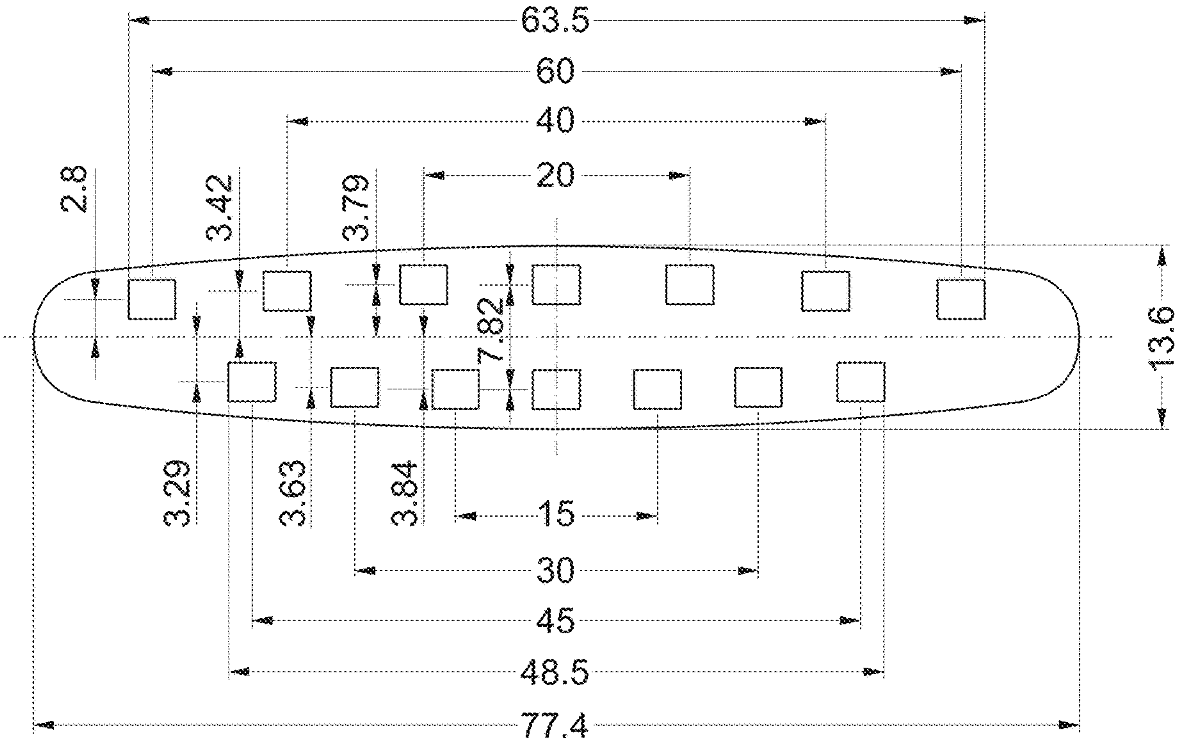
FIG. 14 is a schematic showing an upper array of LEDs and a lower array of LEDs on a flat printed circuit board according to an embodiment.

As shown in FIG. 8, one or more of the LEDs 14 within an array may be spaced at different distances from the central horizontal plane of the mouthpiece 56. FIG. 14 also shows an example of this arrangement. Alternatively, the LEDs 14 within an array may each be spaced at the same distance from the central horizontal plane of the mouthpiece 56. For example, the LEDs 14 of the first array 80 may be arranged in a first plane, and the LEDs 14 of the second array 82 may be arranged in a second plane. A distance between the first array 80 and the second array 82 can be from about 0.5 cm to about 2.0 cm. The first and second planes may be substantially parallel to each other, may converge, or may diverge. Similarly, the horizontal plane of one or more of the LEDs 14 in the first array 80 and the horizontal plane of one or more of the LEDs 14 in the second array 82 may be substantially parallel to each other, may converge, or may diverge. In an embodiment, the angle of convergence or divergence may be from about 0.5° to about 5°. The angled (non-parallel) arrangements can be beneficial to direct light to those surfaces of the teeth being treated that are variably angled and or have atypically inclined surfaces.

In embodiments comprising two or more arrays of LEDs, the arrays can be structured to be powered either simultaneously or sequentially, depending on the process. For example, a first circuit and a second circuit may be connected in parallel, the first circuit driving the first array 80 and the second circuit driving the second array 82. Electric current, supplied by the battery 46 and limited by a resistor, travels through the circuits. A switch may open and close both circuits simultaneously.

Figure 17:
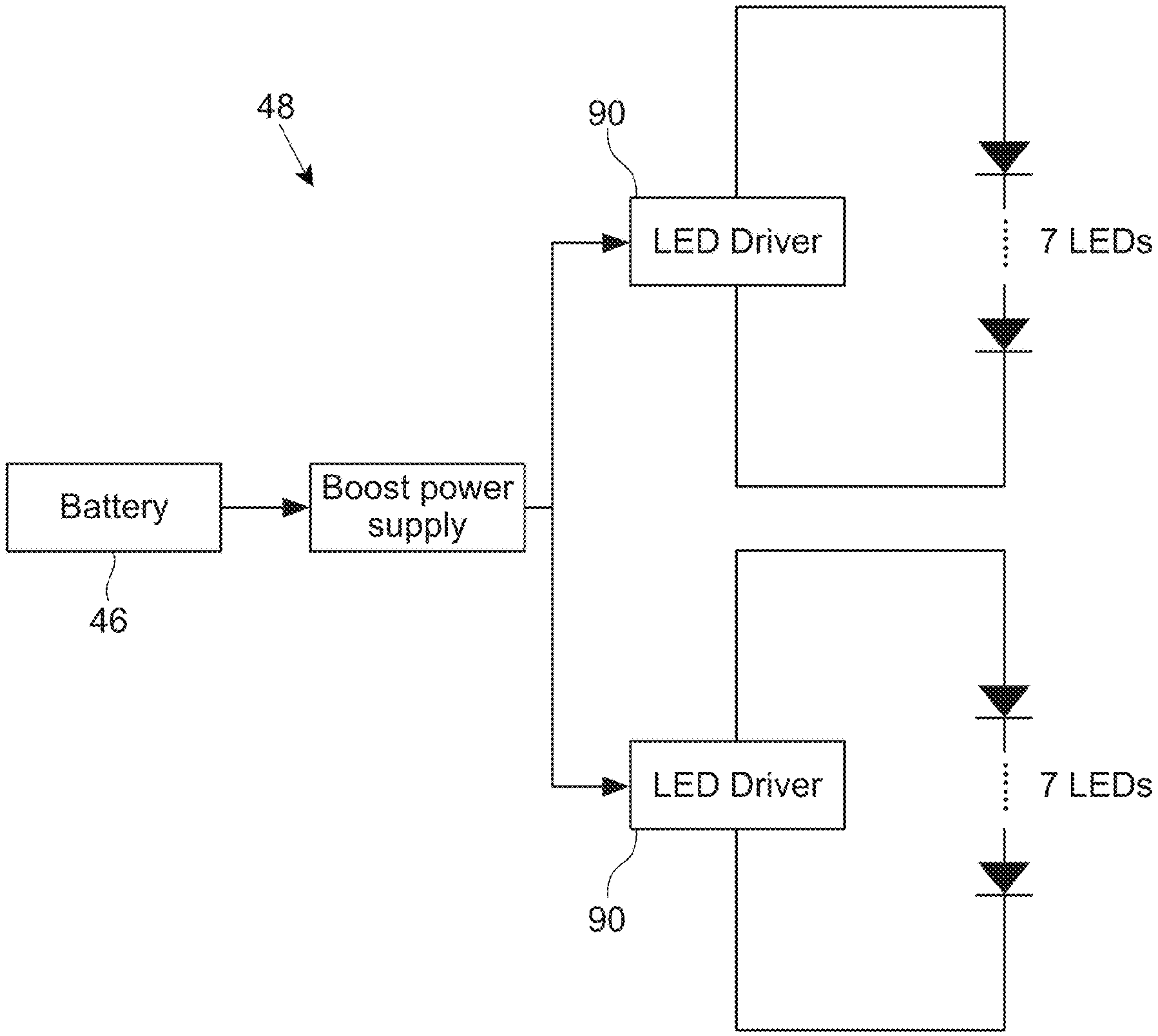
FIG. 17 is a schematic of an electrical diagram according to an embodiment.

An example electrical diagram of the sequentially powered first and second arrays 80, 82 is schematically shown in FIG. 17, where the voltage from the battery 46 is increased in two stages. The power supply is first boosted to increase the voltage from the battery 46 and then additionally increased by an LED driver 90 for both the first array 80 and the second array 82. The amount of power boost may vary. In an example, the initial power supply may be boosted from a voltage of about 1.2V to about 3.3V. The LED drivers 90 may then boost the voltage from about 3.3V to about 21V for two arrays that each include seven LEDs. The boosted voltage may depend on the forward voltage of LEDs. The LED driver 90 may control the output current to drive the LEDs. While the number of LED drivers may vary, FIG. 17 illustrates two LED drivers that are in parallel and used simultaneously providing constant current to a series of LEDs to ensure the light intensity across the LED array is consistent.

In a further example embodiment, the first and second arrays 80, 82 can be powered in repetition at an established alternating frequency. Pulsing LEDs is an effective way to manage both power requirements and heat generation of a given LED and device. A microcontroller or any other suitable mechanism can be structured and configured to automatically and at a prescribed frequency direct electric current from a battery (upon closing of a switch) alternately through first and second circuits, to drive the first and second arrays 80, 82, respectively. In this example embodiment, each of the circuits may include a current-limiting resistor.

LEDs can be vertically aligned or staggered. An example embodiment of the light device 10 shown in FIGS. 7-9 comprises two parallel arrays of LEDs, in which some of the LEDs 14 of the first and second arrays 80, 82 are vertically aligned and some are staggered. For example, the central LEDs 14 of each of the first and second arrays 80, 82 may be vertically aligned. An embodiment (not shown) is contemplated in which the LEDs 14 of the second array 82 are unilaterally stacked relative to the LEDs 14 of the first array 80. In such an embodiment, the individual LEDs 14 of the first array 80 are aligned vertically with corresponding individual LEDs 14 of the second array 82.

The LEDs in the array may be oriented with the light-emitting ends 22 substantially arranged in a single arc or more than one arc. In an embodiment of the LED array, the LEDs 14 in the array may be oriented with the light-emitting ends 22 substantially arranged in two arcs: an inner arc and an outer arc. Such an arrangement is disclosed in commonly assigned U.S. Pat. No. 10,046,173, the entire disclosure of which is incorporated herein by reference. The inner arc may be formed by the inner LEDs 14*b*, and the outer arc may be formed by the outer LEDs 14*a*. The inner arc and the outer arc may lie substantially in a single plane, in which instance the axes of primary focus 78 of the upper LEDs and the lower LEDs will each lie in a single plane, or in different planes.

The light device may be configured to be used in one orientation where the light is simultaneously directed to the maxillary teeth and the mandibular teeth. In another example, the light device may be configured to be used in two orientations, with a first orientation where the light is primarily directed to the maxillary teeth, while in the second orientation, the light is primarily directed to the mandibular teeth. Such a configuration is described in U.S. Pat. No. 10,046,173. To facilitate positioning of the light device to deliver the optimal light intensity, one may wish to provide a locating or positioning feature, such as, e.g., a protrusion, a boss or a ledge, which can be used as a geometrical point of reference and against which a user can locate the maxillary and/or mandibular anterior teeth.

In various embodiments, a light device may include one or more additional heat management techniques. The light device may include one or more feedback sensors that detect heat against a specified limit. The light device may include one or more materials to absorb heat that is generated from the light source and draw it away from the intended illumination surface (e.g., a heat sink). The light device may include active and/or passive ventilation (e.g., vent holes). The light source can be pulsed at a frequency to limit the heat output while delivering meaningful light intensity. The light source can be pulsed at high frequency that isn't observable to the consumer if desired. These additional heat management techniques may be used alone or in combination.

Whitening Process

A process for whitening may include several steps, including applying an oral care composition, such as a whitening composition including a bleaching agent, to the teeth and providing a light source arranged in a certain configuration and powered to direct light to the teeth in a certain predetermined pattern.

Suitable bleaching agents may comprise a source of peroxide radicals. Bleaching agents may include peroxides, metal chlorites, perborates, percarbonates, peroxyacids, persulfates, compounds that form the preceding compounds in situ, and combinations thereof. Examples of peroxide compounds include hydrogen peroxide, urea peroxide, calcium peroxide, carbamide peroxide, and mixtures thereof. Suitable metal chlorites include, without limitation, calcium chlorite, barium chlorite, magnesium chlorite, lithium chlorite, sodium chlorite, potassium chlorite, and mixtures thereof. Additional bleaching agents may also include hypochlorite (such as metal hypochlorite) and chlorine dioxide. Persulfates include salts of peroxymonosulfate, peroxydisulfate, and combinations thereof. The bleaching agent material can be an aqueous or solid material.

The concentration of bleaching agent in the whitening composition may vary. For example, the whitening composition may have a bleaching agent concentration in a range of from about 0.002% to about 50%, from about 0.01% to about 40%, from about 0.05% to about 20%, from about 0.1% to about 10%, from about 1% to about 5%, from about 0.05% to about 10%, from about 0.05% to less than about 7.5%, from about 0.1% to about 7%, from about 0.1% to about 5%, from about 0.05% to about 3%, from about 0.05% to about 1%, from about 1% to less than 7.5%, or from about 3% to less than about 7.5%, by weight, of the whitening composition. The whitening composition may have a bleaching agent concentration of about 0.1%, about 1%, about 3%, about 5%, about 7%, less than about 7%, less than about 7.5%, about 10%, about 15%, about 20%, about 30%, or about 35%, by weight, of the whitening composition.

A whitening composition can be applied to the anterior surfaces of at least six mandibular or maxillary anterior teeth. A number of tooth-whitening compositions may be utilized in the process of the disclosure described herein, such as, e.g., many peroxide-based tooth-whitening compositions with varying concentrations of peroxide may be provided. Other additives may also be provided in the composition, including, e.g., photosensitizing agents, gelling agents, humectants, pH-adjusting agents, stabilizing agents, desensitizing agents, accelerating agents, bleach activators, or combinations thereof. The whitening composition may be free of a photosensitizing agent. The process may include not applying photosensitizing agents to the teeth. The composition may be provided in the form of a viscous liquid, paste, emulsion, gel, solution, or any other state or phase that may be applied to the teeth. Further, the whitening composition may be applied directly to the teeth, may be contained by a tray placed over the teeth, or may be provided on a carrier such as a strip of flexible material configured to be applied to the tooth surfaces to be whitened. Non-limiting examples of suitable tooth-whitening products include the strip-based tooth-whitening products described in U.S. Pat. Nos. 6,949,240 and 8,840,918, and other whitening compositions (e.g., emulsions) disclosed in U.S. Pat. Nos. 11,096,874, 11,147,753, and 11,224,760, the entire disclosures of which are incorporated herein by reference. The whitening composition can be maintained on the at least six teeth for a first (or delay) time period. During the first (or delay) period, a chemical whitening composition may be maintained on the user's teeth without the application of electromagnetic radiation from the light source.

After the first time period, electromagnetic radiation may be applied to the teeth in a subsequent second time period (or the light-radiation period). An electromagnetic radiation comprising blue visible light or near-visible UV light of at least a threshold intensity from the least a first array of LEDs may be directed to the anterior surfaces of the at least six teeth for a second time period. The first time period can beneficially have a duration that is at least greater than 50% a total duration of the first time period and the second time period combined. The electromagnetic radiation may be applied through a translucent chemical whitening composition (and any corresponding translucent carrier for the composition, such as a tray or adhesive strip) when present. The first time period can be from about 20 minutes to about 120 minutes. The second time period can be from about 2 minutes to about 10 minutes.

The delay period can be greater than the light-radiation period, or greater than 50% of a total duration of the delay and light-radiation periods, such that the teeth are exposed to electromagnetic radiation for less than half of the entire duration of the tooth-whitening treatment. The delay period may also be greater than about 60%, greater than about 70%, greater than about 80%, greater than about 90%, greater than about 95%, or greater than about 96%, or greater than about 97%, or greater than about 98%, or greater than about 99%, or greater than about 99.5%, or greater than about 99.9%, or between about 80% and about 90% of the total duration of the delay and light-radiation periods.

Depending on the process, condition of the teeth, and other relevant factors, the first time period (or delay of the electromagnetic radiation) and the second time period (or the period of electromagnetic radiation) can be selected from a number of suitable ranges, as e.g., those disclosed in commonly assigned U.S. Pat. No. 9,622,840. The durations of the delay and light-radiation periods of the tooth whitening-treatment may be selected based on several factors. For example, the delay period duration may be selected to allow the oxidizing or bleaching agent sufficient time to reach the tooth stains below the outer surfaces of the teeth before light activation of the stains.

In some embodiments of the process, the tooth-whitening process may include an additional third time period, or second delay period, performed after the light-radiation period. The whitening composition may be reapplied to the teeth after the light-radiation period and/or the whitening composition from the initial application may continue to be maintained on the teeth. During the third period, the whitening composition remains on the teeth without a light treatment, prior to removal. The tooth-whitening process may also include a fourth time period, or second light-radiation period performed after the second delay period.

For example, the delay period may range from greater than 0 seconds to about 480 minutes, from greater than 0 seconds to about 120 minutes, from about 2 minutes to about 480 minutes, or from about 5 minutes to about 55 minutes, or from about 15 minutes to about 25 minutes.

For example, the light-radiation period may range from greater than 0 seconds to about 120 minutes, from greater than 0 seconds to about 60 minutes, from about 1 second to about 90 minutes, from about 3 seconds to about 30 minutes, from about 30 seconds to about 10 minutes, from about 30 seconds to about 7 minutes, from about 30 seconds to about 5 minutes, from about 2 minutes to about 120 minutes, from about 2 minutes to about 5 minutes, or from about 3 minutes to about 7 minutes.

The total duration of the delay and light-radiation periods may range, e.g., from about 4 minutes to about 500 minutes, or from about 10 minutes to about 60 minutes, or from about 15 minutes to about 30 minutes.

Before the beginning of a light-radiation time period, the whitening composition can be removed from the teeth. Alternatively, the whitening composition can be removed from the teeth after the completion of a light-radiation time period.

In one embodiment of the process utilizing two arrays (e.g., first and second arrays 80, 82), the process may comprise directing, after the first time period, an electromagnetic radiation comprising blue visible light or near-visible UV light of at least a threshold intensity from the first and second arrays 80, 82 for the second time period to the anterior surfaces of the at least six teeth, the first time period having a duration greater than 50% of a total duration of the first time period and the second time period. In such an embodiment, the first array 80 of LEDs 14 delivers the light primarily to the maxillary teeth and the second array 82 of LEDs 14 delivers the light primarily to the mandibular teeth. The LEDs 14 may be aligned interproximally when the light device 10 is positioned adjacent the teeth (e.g., as shown in FIGS. 10 and 11).

The light from the first array 80 and the second array 82 can be delivered in various patterns and sequences. In an embodiment, the first array 80 and the second array 82 illuminate the teeth simultaneously. In another example embodiment, the first array 80 and the second array 82 illuminate the teeth sequentially. In still another example embodiment of the process, the first array 80 and the second array 82 illuminate the teeth in repetition at an established alternating frequency.

Timer

The light device may optionally include a timer for indicating starting or stopping points for the delay period and/or the electromagnetic radiation period. The timer may be configured to activate or deactivate the light source (e.g., via a circuit or controller). For example, the timer may be configured to delay illumination of the light source for a predetermined delay period whereby no irradiation from the light source is applied to the teeth during the delay period. The timer may be configured to deactivate the light source automatically after a predetermined period of time (e.g., the light-radiation period described herein) from the activation of the light source. Limiting the electromagnetic radiation period without compromising the whitening benefit can help control light intensity and heat exposure from the light source.

While a timer for deactivating the light after a predetermined period of time ("on timer") provides a defined period of heat exposure, a user may choose to reactivate the light before the teeth have had time to return to a physiological temperature. The light device may optionally include a timer for preventing the light source to be reactivated after a predetermined period of activation. The period of time before the light source may be reactivated ("device sleep period") may be based on, for example, the period of time it takes for the tooth to return to physiological temperature. The off period may be, for example, in a range of from about 15 seconds to about 90 minutes, from about 15 seconds to about 10 minutes, from about 15 seconds to about 5 minutes, from about 15 seconds to about 1 minute, from about 30 seconds minute to about 15 minutes, from about 5 minutes to about 10 minutes, from about 5 minutes to about 20 minutes, from about 3 minutes to about 7 minutes, or may be about 30 seconds, or about 1, 5, 10, 15, 20, 25, or 30 minutes. The predetermined period of activation (e.g., the light-radiation period described herein) may be based on a safe maximum exposure time period for a light source of a defined light intensity and associated temperature in conjunction with treatment peroxide concentration.

If the light is manually turned off before the end of the predetermined period of activation, the timer may pause. The timer may be paused until the end of the predetermined period of time. For example, if the predetermined period of time is 5 minutes and the user turns off the light, the timer may remain paused for 4 minutes. If the light source is manually reactivated while the timer is paused, the light device 10 may be configured to restart the timer at the time of the pause and proceed to the end of the predetermined period of activation (excluding the time of the pause). Using the prior example, if the user manually reactivates the light source after 2 minutes after pausing, the timer will deactivate the light after 4 more minutes (i.e., 7 total minutes including activation, pause, and reactivation). The timer may alternatively be paused for a predetermined pause period (e.g., about 1, 2, 3, 4, 5, 10, or 15 minutes). At the end of the pause, the timer may prevent reactivation of the light source for the duration of an off period.

The timer may optionally indicate a period of disuse. For example, the light device may measure the time since the most recent use of the light device. The light device may be configured to notify the user that a certain amount of time has passed since the prior use. The disuse period may be, without limitation, about 1, 2, 3, 4, 5, 6, or 7 days or about 1, 2, 3, or 4 weeks.

The light device may be configured to notify the user that a timer is complete. The light device may provide a visual indication, audible indication, or a combination thereof that a predetermined period is over. For example, a user may press a button to begin the predetermined delay period after applying the whitening composition to their teeth; after the predetermined delay period ends, the light device may beep or cause the light source to flash or turn on indicating that the user can begin applying light to their teeth. As another example, the light device may beep or cause the light source to flash after a predetermined period of disuse has passed since the prior use of the light device.

Kit

The light devices and whitening compositions described herein may be combined in a kit. A kit may also include an applicator. The applicator may include, without limitation, a paint-on device, a syringe, a squeezable tube, a brush, a pen or brush tip applicator, a doe's foot applicator, a swab, a lip gloss applicator, or a combination thereof. The applicator may include a delivery carrier such as a strip, a dental tray, a sponge material, or a combination thereof. The kit may include instructions for use, so that the kit can be used by consumers in a convenient manner.

Delivery System

Figure 18:
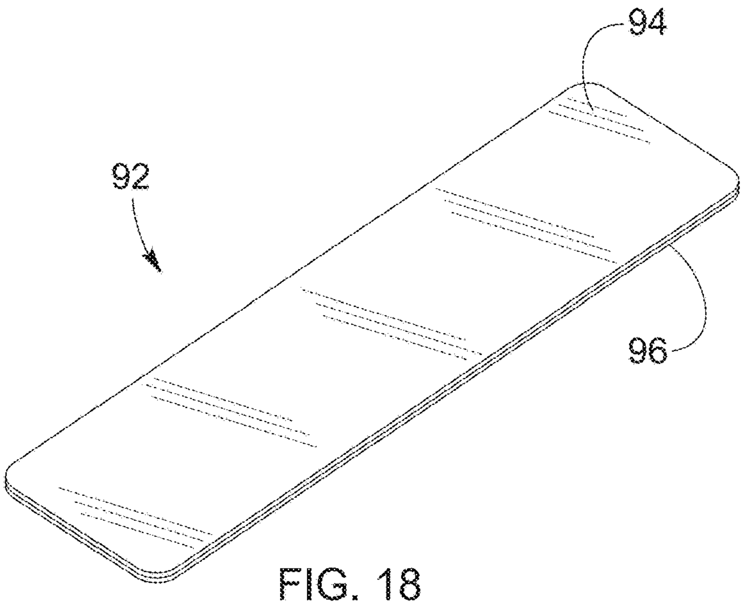
FIG. 18 shows a perspective view of a delivery carrier and whitening composition.

The whitening compositions may provide whitening benefits to the oral cavity by being directly applied to the teeth without using a delivery carrier system. In other embodiments, a delivery system may be used that includes the whitening composition in combination with a delivery carrier. For example, as shown in FIG. 18, a delivery system 92 may comprise a first layer 94 of a carrier material and a second layer of a whitening composition 96 comprising a bleaching agent releasably located within the whitening composition. A suitable first layer may comprise a delivery carrier including a strip of material, a dental tray, a sponge material, and mixtures thereof. In certain embodiments, the delivery carrier may be a strip of material, such as a permanently deformable strip. Suitable strips of material or permanently deformable strips are for example disclosed in U.S. Pat. Nos. 10,285,915; 6,136,297; 6,096,328; 6,045,811; 5,989,569; 5,894,017; 5,891,453; and 5,879,691.

The delivery carrier may be attached to the teeth via an attachment means that is part of the delivery carrier, for example the delivery carrier may be of sufficient size that, once applied the delivery carrier overlaps with the oral soft tissues rendering more of the teeth surface available for bleaching. The delivery carrier may also be attached to the oral cavity by physical interference or mechanical interlocking between the delivery carrier and the oral surfaces including the teeth.

The delivery carrier may be transparent or translucent to electromagnetic radiation with wavelengths from about 200 nm to about 1700 nm. In certain embodiments, the delivery carrier allows from about 10% to 100%, 10% to 40%, 20% to 100%, 40% to 100%, or 40% to 90% of electromagnetic radiation from about 400 nm to about 500 nm to pass through.

Where the delivery carrier is a strip of material, the second layer composition may be coated on the strip, or be applied by the user to the strip, or be applied by the user to the teeth and then the strip may be placed over the coated teeth. The amount of composition applied to the strip or teeth may depend upon the size and capacity of the strip, concentration of the active and the desired benefit; for example from about 0.0001, 0.001 or 0.01 g to about 0.01, 0.1, 1, or 5 g may be used or any other numerical range, which is narrower and which falls within such broader numerical range, as if such narrower numerical ranges were all expressly written herein, of composition, in particular from about 0.001 g g to about 0.5 g g or from about 0.1 g to about 0.4 g of oral composition may be used. In addition, from about 0.0001, 0.001 or 0.01 g to about 0.01, 0.1, 0.5, or 1 g composition per square centimeter of material (g/cm$^2$) may be used or any other numerical range, which is narrower and which falls within such broader numerical range, as if such narrower numerical ranges were all expressly written herein; in certain embodiments less than about 0.2 g/cm$^2$, from about 0.0001 g/cm$^2$ to about 0.1 g/cm$^2$, or from about 0.01 g/cm$^2$ to about 0.04 g/cm$^2$. In addition, or alternatively, from about 1 microgram to about 5000 micrograms active or bleaching agent per square centimeter of material (microgram/cm$^2$), preferably from about 10 micrograms/cm$^2$ to about 500 micrograms/cm$^2$, and more preferably from about 50 micrograms/cm$^2$ to about 100 micrograms/cm$^2$ active or bleaching agent per square centimeter of material may be used.

A suitable delivery system may deliver bleaching agents provided by a whitening composition to the teeth and the oral cavity. Delivery system comprises a material in the form of a strip of material which is substantially flat and may have rounded corners. Onto said strip a second layer comprising the whitening composition is releasably applied. The second layer may be homogenous and may be uniformly and evenly coated onto strip. In addition, the second layer comprising the whitening compositions may be a coating only along a longitudinal axis of a portion of strip of material or may be applied as stripes, spots, and/or other patterns. However, the second layer may be a laminate or separated layers of components, an amorphous mixture of components, separate stripes or spots or other patterns of different components, or a combination of these structures, including a coating of the second layer along a longitudinal axis of a portion of the strip of material.

The second layer may contain or is itself an active, such as a composition, compound, or mixture capable of influencing or effecting a desired change in appearance or structure of the surface it contacts. Example actives include, without limitation, hydrogen peroxide, carbamide peroxide, sodium fluoride, sodium monofluorophosphate, pyrophosphate, chlorhexidine, polyphosphate, triclosan, and enzymes. Examples of appearance and structural changes include, but are not necessarily limited to, whitening, stain bleaching, stain removal, remineralization to form fluorapatite, plaque removal, and tartar removal.

In addition, the second layer composition may comprise adhesive means in order to stably attach the delivery system to the tooth surface. In certain embodiments, the composition may provide the intended stickiness and adhesiveness by its own, for example by choosing a hydrophobic phase which already provides adhesive properties by adding adhesive material to the compositions, or both. In certain embodiments, if added, an adhesive may provide additional properties, such as thickening/rheology modifying properties.

A delivery system may be applied to the tooth surface of a plurality of adjacent teeth. Embedded in adjacent soft tissue is a plurality of adjacent teeth. Adjacent soft tissue herein defined as soft tissue surfaces surrounding the tooth structure including: papilla, marginal gingival, gingival sulcus, inter dental gingival, and gingival gum structure on lingual and buccal surfaces up to and including mucogingival junction on the pallet.

The delivery system may be a strip and second layer comprising the whitening composition, where the second layer is located on the side of strip of material facing teeth. Composition of second layer may be pre-applied to strip of material or may be applied to strip of material by the user prior to application to the teeth. Alternatively, the composition of second layer may be applied directly to teeth by the user and then covered by a strip. In any case, strip of material may have a thickness and flexural stiffness such that it can conform to the contoured surfaces of teeth and to adjacent soft tissue. Thus, the strip of material may have sufficient flexibility to form to the contours of the oral surface, the surface being a plurality of adjacent teeth. The strip may also readily conformable to tooth surfaces and to the interstitial tooth spaces without permanent deformation when the delivery system is applied. The delivery system can be applied without significant pressure.

The first layer of the delivery system may be comprised of a strip of material. Such first layer materials are described in more detail in U.S. Pat. Nos. 10,285,915; 6,136,297; 6,096,328; 6,045,811; 5,989,569; 5,894,017; 5,891,453; and 5,879,691. The strip serves as a protective barrier for the active agent in the second layer. It prevents leaching or erosion of the second layer by for example, the wearer's tongue, lips, and saliva. This allows the hydrophilic active agent particles in the second layer to act upon the tooth surfaces of the oral cavity for the intended period of time, for example from several minutes to several hours.

The following description of strip of material may apply to the delivery systems with the strip layer or any form of strips. The strip of material may comprise polymers, natural and synthetic woven materials, non-woven material, foil, paper, rubber and combinations thereof. The strip of material may be a single layer of material or a laminate of more than one layer. Regardless of the number of layers, the strip of material may be substantially water insoluble. The strip material may also be water impermeable. Suitable strip material may be any type of polymer or combination of polymers that meet the required flexural rigidity and are compatible with oral care substances. Suitable polymers include, but are not limited to, polyethylene, ethylvinylacetate, polyesters, ethylvinyl alcohol and combinations thereof. Examples of polyesters include Mylar® and fluoroplastics such as Teflon®, both manufactured by DuPont. In certain embodiments, the material used as strip of material is polyethylene. The strip of material may be less than about 1 mm (millimeter) thick, less than about 0.05 mm thick, or from about 0.001 to about 0.03 mm thick. A polyethylene strip of material may be less than about 0.1 mm thick or from about 0.005 to about 0.02 mm thick.

A delivery carrier may be a dissolvable film that can be adhered to the oral cavity thereby releasing an active, the dissolvable film comprising water-soluble polymers, one or more polyalcohols, and one or more actives. In addition to one or more actives, a dissolvable film may contain a combination of certain plasticizers or surfactants, colorants, sweetening agents, flavors, flavor enhancers, or other excipients commonly used to modify the taste of formulations intended for application to the oral cavity. The resulting dissolvable film is characterized by an instant wettability which causes the dissolvable film to soften soon after application to the mucosal tissue, thus preventing the user from experiencing any prolonged adverse feeling in the mouth, and a tensile strength suitable for normal coating, cutting, slitting, and packaging operations.

The dissolvable film may comprise a water-soluble polymer or a combination of water-soluble polymers, one or more plasticizers or surfactants, one or more polyalcohols, and an active.

The polymers used for the dissolvable film include polymers which are hydrophilic and/or water-dispersible. Examples of polymers that can be used include polymers that are water-soluble cellulose-derivatives, such as hydroxypropylmethyl cellulose, hydroxyethyl cellulose, or hydroxypropyl cellulose, either alone, or mixtures thereof. Other optional polymers, without limiting the invention, include polyvinyl pyrrolidone, carboxymethyl cellulose, polyvinyl alcohol, sodium alginate, polyethylene glycol, natural gums like xanthane gum, tragacantha, guar gum, acacia gum, arabic gum, water-dispersible polyacrylates like polyacrylic acid, methylmethacrylate copolymer, carboxyvinyl copolymers. The concentration of the water-soluble polymer in the final film can very between 20 and 75% (w/w), or between 50 and 75% (w/w).

The surfactants that may be used for the dissolvable film may be one or more nonionic surfactants. When a combination of surfactants is used, the first component may be a polyoxyethylene sorbitan fatty acid ester or an ALPHA-hydro-OMEGA-hydroxypoly (oxyethylene)poly(oxypropylene)poly(oxyethylene) block copolymer, while the second component may be a polyoxyethylene alkyl ether or a polyoxyethylene castor oil derivative. In certain embodiments, the HLB value of the polyoxyethylene sorbitan fatty acid ester should be between 10 and 20, whereby a range of 13 to 17 may also be used. The ALPHA-hydro-OMEGA-hydroxypoly(oxyethylene)poly(oxypropylene) poly(oxyethylene) block copolymer may contain at least about 35 oxypropylene-units, and in certain embodiments not less than about 50 oxypropylene-units.

The polyoxyethylene alkyl ether may an HLB value between 10 and 20, and in certain embodiments an HLB value of not less than 15 may be used. The polyoxyethylene castor oil derivative may have an HLB value of 14-16.

To achieve the desired instant wettability, the ratio between the first and second component of the binary surfactant mixture may be kept within 1:10 and 1:1, or between 1:5 and 1:3.

The total concentration of surfactants in the dissolvable film depends on the properties of the other ingredients, but usually may be between 0.1 and 5% (w/w).

The polyalcohol can be used to achieve a desired level of softness of the dissolvable film. Examples of polyalcohols include glycerol, polyethylene glycol, propylene glycol, glycerol monoesters with fatty acids or other pharmaceutically used polyalcohols. The concentration of the polyalcohol in the dry film usually ranges between 0.1 and 5% (w/w).

The shape of the strip of material may be any shape or size that covers the desired oral surface. For example, in certain embodiments the strip of material may have rounded corners to avoid irritation of the soft tissue of the oral cavity. "Rounded corners," as used herein means generally lacking sharp angles or points, for example one or more angles of 1350 or less. The length of the strip of material may be from about 2 cm (centimeter) to about 12 cm, or from about 4 cm to about 9 cm. The width of the strip of material may also depend on the oral surface area to be covered. The width of the strip of material may be from about 0.5 cm to about 4 cm or from about 1 cm to about 2 cm. The strip or material may be worn as a patch on one or several teeth to treat a localized condition.

The strip of material may contain shallow pockets. When the oral composition is coated on a strip of material, bleaching agents and/or oral care actives, fill shallow pockets to provide reservoirs of additional bleaching agents and/or oral care actives. Additionally, the shallow pockets help to provide texture to the delivery system. The strip of material may have an array of shallow pockets. Generally, the shallow pockets are approximately 0.4 mm across and about 0.1 mm deep. When shallow pockets are included in the strip of material and oral compositions herein are applied to it in various thicknesses, in certain embodiments the overall thickness of the delivery system is less than about 1 mm, in certain embodiments the overall thickness is less than about 0.5 mm.

Flexural stiffness is a material property that is a function of a combination of strip of material thickness, width, and material modulus of elasticity. The test described below is a method for measuring the rigidity of films, such as polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter wired to the strain gauge is calibrated in terms of deflection force. The rigidity of the sample is read directly from the microammeter and expressed as grams per centimeter of the sample strip width. In certain embodiments, a strip of material which is suitable to be used as delivery carrier of the compositions as disclosed herein may show a flexural stiffness of less than about 5 g/cm as measured on a Handle-O-Meter, model #211-300, available from Thawing-Albert Instrument Company of Philadelphia, PA as per test method ASTM D2923-95. The strip may have a flexural stiffness less than about 3 g/cm, less than about 2 g/cm or a flexural stiffness from about 0.1 to about 1 g/cm. Generally, the flexural stiffness of the strip of material may be substantially constant and does not change during normal use. For example, the strip of material does not need to be hydrated for the strip to achieve the low flexural stiffness in the above-specified ranges. This relatively low stiffness enables the strip of material to cover the contours of the oral surface with very little force being exerted. That is, conformity to the contours of the oral surface of the wearer's mouth is maintained because there is little residual force within the strip of material to cause it to return to its shape just prior to its application to the oral surface, i.e., substantially flat. For example, in certain embodiments a strip of material's flexibility enables it to contact soft tissue over an extended period of time without irritation; such that a strip of material does not require pressure for retention against the oral surface.

The delivery systems as used herein may comprise an adhesion means, such that they are capable of adhesion to oral surfaces, especially the teeth. This adhesion means may be provided by the present compositions herein or the adhesion means may be provided independently of the compositions herein (e.g., the adhesion means is a separate phase from the compositions herein where the compositions may also have an adhesive means). In certain embodiments, the strip of material may be held in place on the oral surface by adhesive attachment provided by the present composition. The viscosity and general tackiness of the oral composition to dry surfaces may cause the strip to be adhesively attached to the oral surface without substantial slippage from the frictional forces created by the lips, teeth, tongue, and other oral surfaces rubbing against the strip of material while talking drinking, etc. However, this adhesion to the oral surface may be low enough to allow the strip of material to be easily removed by the wearer by simply peeling off the strip of material using one's finger. The delivery system may be easily removable from the oral surfaces without the use of an instrument, a chemical solvent or agent or excess friction.

In addition, in certain embodiments the strip of material may be held in place on the oral surface by adhesive means and attachment provided by the delivery carrier itself. For example, the strip of material can extend, attach, and adhere to the oral soft tissue. In addition, in certain embodiments an adhesive can be applied to that portion of the strip of material that will attach the delivery systems to the oral soft tissue. The delivery carrier may also be attached to the oral cavity by physical interference or mechanical inter-locking between the delivery carrier and the oral surfaces including the teeth. In addition, the strip of material may be held in place by an adhesion means that is independent of the composition, as disclosed in International Patent Application No. WO 03/015656.

Suitable adhesion means are known to the skilled person. When the adhesive means, if present, is provided by an adhesive, the adhesive may be any adhesive which may be used to adhere materials to the tooth surface or to a surface of the oral cavity surfaces. Suitable adhesives include, but are not limited to, skin, gum and muco adhesives, and should be able to withstand the moisture, chemicals and enzymes of the oral environment for long enough for the oral care actives and/or bleach to take effect, but may be soluble and/or biodegradable thereafter. Suitable adhesives may for example comprise water soluble polymers, hydrophobic and/or non-water soluble polymers, pressure and moisture sensitive adhesives, e.g. dry adhesives which become tacky upon contact with the mouth environment, e.g. under the influence of moisture, chemicals or enzymes etc. in the mouth. Suitable adhesives include natural gums, synthetic resins, natural or synthetic rubbers, those gums and polymers listed above under "Thickening Agents", and various other tacky substances of the kind used in known adhesive tapes, those known from U.S. Pat. No. 2,835,628.

The delivery carrier, such as a strip, may be formed by several of the film making processes known in the art. For example, a strip of polyethylene is made by a blown process or a cast process. Other processes including extrusion or processes that do not affect the flexural rigidity of the strip of material are also feasible. In addition, the present compositions forming a second layer onto the strip may be incorporated onto the strip during the processing of the strip and/or the present composition may be a laminate layer on the strip. The second layer attached to the strip of such a delivery system as disclosed above comprises a safe and effective amount of the present composition described herein.

In addition, the delivery system may comprise an optional release liner. Such a release liner may be formed from any material which exhibits less affinity for the second layer composition than the second layer composition exhibits for itself and for the first layer strip of material. The release liner may comprise a rigid sheet of material such as polyethylene, paper, polyester, or other material, which is then coated with a nonstick-type material. The release liner may be cut to substantially the same size and shape as the strip of material or the release liner may be cut larger than the strip of material to provide a readily accessible means for separating the material from the strip. The release liner may be formed from a brittle material that cracks when the strip is flexed or from multiple pieces of material or a scored piece of material. Alternatively, the release liner may be in two overlapping pieces such as a typical adhesive bandage design.

In certain embodiments, the delivery carrier may be a permanently deformable strip of material having a yield point and thickness such that the strip of material substantially conforms to a shape of a tooth via permanent deformation under a pressure less than about 250,000 Pascals as it has been found that wearers will press a strip onto each tooth using one fingertip having about one square centimeter surface area. They typically apply force at each tooth for one second or less with a typical application pressure ranging from about 100,000 Pascals to about 250,000 Pascals.

In certain embodiments, a strip of material has visco-elastic properties which enable it to creep as well as bend in order to conform across several teeth and around the arch of the wearer's mouth. It is important that the necessary permanent deformation occurs under minimum normal force being applied by the wearer.

The oral composition may also be applied to the tooth surface and may be covered with the deformable strip before or after it has been shaped. Additionally or alternatively, the oral composition may be applied to the deformable strip as pre-coating and may be applied together with the strip to the tooth surface before or after the deformable strip has been shaped, where the strip is applied such that when the delivery system is placed on a surface of the tooth, the oral composition contacts the tooth surface providing an active onto the tooth surface. In addition or alternatively, the deformable strip of material may be applied to the teeth with a force sufficient to shape the delivery carrier such that it at least partially conforms to the shape of the teeth, then the shaped strip of material may be removed from the tooth surface, the oral care composition may be applied to the shaped strip of material, and the shaped strip of material may be reapplied to the tooth surface such that it at least partially conforms to a shape of the tooth and contacts the oral care composition against the tooth surface. If the deformable strip is applied together with the oral composition to the tooth surface the oral composition may also comprise adhesive agents to hold the delivery system in place for a sufficient time to allow the active of the oral composition to act upon the surface. The oral composition, if used together with a deformable strip, may have an extrusion resistance sufficient to withstand a normal force applied to shape the deformable strip of material so that the substance is not substantially extruded from between the deformable strip of material and the surface during manual shaping of the deformable strip of material. By "substantially extruded from" is meant that at least 50% or more of the oral composition is extruded from between the deformable strip of material and the tooth and adjoining soft tissue surfaces.

The deformable strip of material may be made of a permanently deformable material, such as wax, putty, tin or foil, as a single layer or a combination of layers or materials, such as a laminate. In certain embodiments, the deformable strip may be wax, such as #165 sheet wax formulated and manufactured by Freeman Mfg. & Supply Co. of Cleveland, Ohio. This particular wax readily conforms to the shape of a tooth under a pressure of about 133,000 Pascal which is the pressure generated when the wearer applies a normal force of about 3 pounds (1.36 kg) over an area of about one square centimeter. The deformable strip of material may have a nominal film thickness of about 0.8 mm, where the deformable strip may be substantially flat and rectangular in shape with rounded corners. The deformable strip of material may have a length sufficient to cover a plurality of adjacent teeth while conforming to the curvature of the wearer's mouth and gaps between the adjacent teeth. If the deformable strip of material includes the oral composition coated thereon, the oral composition may have an overall thickness less than about 1.5 mm. Deformable strips as disclosed herein may also be used as the material for the strip of material. Thus, general features of a strip of material may also apply to the deformable strip of material. In addition, a release liner and/or shallow pockets may also be combined with a deformable strip of material.

The whitening compositions may be used in combination with a delivery carrier including a dental tray and/or foam material. Dental trays are well known in the whitening art. The general process for preparing dental trays is known in the art. Dentists have traditionally utilized three types of dental appliances for bleaching teeth.

The first type is a rigid appliance which is fitted precisely to the patient's dental arches. For example, an alginate impression which registers all teeth surfaces plus gingival margin is made and a cast is promptly made of the impression. If reservoirs are desired, they are prepared by building a layer of rigid material on the cast on specific teeth surfaces to be treated. A dental tray is then vacuum formed from the modified cast using conventional techniques. Once formed, the tray is preferably trimmed barely shy of the gingival margin on both buccal and lingual surfaces. Enough tray material should be left to assure that all of the tooth will be covered to within about ¼ to about ⅓ mm of the gingival border upon finishing and beveling the tray periphery. One can scallop up and around interdental papilla so that the finished tray does not cover them. All tray edges are preferably smoothed so that the lip and tongue will not feel an edge prominence. The resulting tray provides a perfect fit of the patient's teeth optionally with reservoirs or spaces located where the rigid material was placed on the cast. Dental trays may comprise of soft transparent vinyl material having a preformed thickness from about 0.1 cm to about 0.15 cm. Soft material is more comfortable for the patient to wear. Harder material (or thicker plastic) may also be used to construct the tray.

A second type of rigid custom dental appliance is an "oversized" rigid custom dental appliance. The fabrication of rigid, custom dental appliances entails fabricating cast models of the patient's dental arch impressions, and heating and vacuum-forming a thermoplastic sheet to correspond to the cast models of a patient's dental arches. Thermoplastic films are sold in rigid or semi rigid sheets and are available in various sizes and thickness. The dental laboratory fabrication technique for the oversized rigid dental appliance involves augmenting the facial surfaces of the teeth on the cast models with materials such as die spacer or light cured acrylics. Next, thermoplastic sheeting is heated and subsequently vacuum formed around the augmented cast models of the dental arch. The net effect of this method results in an "oversized" rigid custom dental appliance.

A third type of rigid custom dental appliance, used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

A fourth type of dental tray replaces rigid custom dental appliances with disposable U-shaped soft foam trays, which may be individually packaged, and which may be saturated with a pre-measured quantity of the composition. The soft foam material is generally an open celled plastic material. Such a device is commercially available from Cadco Dental Products in Oxnard, Calif. under the tradename VitalWhite. These soft foam trays may comprise a backing material (e.g., a closed cell plastic backing material) to minimize the elution of the bleaching agent from the device, into the oral cavity to minimize ingestion by the patient and/or irritation of the oral cavity tissues. Alternatively, the soft foam tray is encased by a nonporous flexible polymer or the open cell foam is attached to the frontal inner wall of the dental appliance and/or the open cell foam is attached to the rear inner wall of the dental appliance. Those of ordinary skill in the art will readily recognize and appreciate, that the present compositions must be thick enough not to simply run out between the open cell structure of the foam and must be thin enough to slowly pass through the open cell foam over time. In other words, the open cell foam material has an internal structural spacing sized relative to the viscosity of the compositions to absorb and allow the composition to pass there through.

An example of a closed cell material is a closed-cell polyolefin foam sold by the Voltek division of Sekisui America Corporation of Lawrence, Mass. under the tradename Volora which is from 1/32" to ⅛" in thickness. A closed cell material may also comprise of a flexible polymeric material. An example of an opened cell material is an open celled polyethylene foam sold by the Sentinel Foam Products division of Packaging Industries Group, Inc. of Hyannis, Mass. under the tradename Opcell which is from 1/16" to ⅜" in thickness. Other open cell foam useful herein include hydrophilic open foam materials such as hydrogel polymers (e.g., Medicell foam available from Hydromer, Inc. Branchburg, J.J.). Open cell foam may also be hydrophilic open foam material imbibed with agents to impart high absorption of fluids, such as polyurethane or polyvinylpyrrolidone chemically imbibed with various agents.

Whitening Boost

It has been reported that "higher peroxide concentrations enhance bleaching efficacy but also increase the peroxide penetration through the tooth structure." Borges et al., *Influence of Bleachin gel Peroxide Concentration on Color and Penetration through the Tooth Structure*, The Journal of Contemporary Dental Practice (2021), DOI:10.5005/jp-journals-10024-3023. As a result, many marketed products use high concentrations of a bleaching agent, such as hydrogen peroxide, to maximize the whitening benefit. A trade-off of these approaches is lower product tolerability with teeth sensitivity and soft tissue irritation leading to reduced consumer compliance and lower overall realized benefit. A minimum threshold light intensity is required to increase the quantum state or energy level of a stain molecule to accelerate bleaching with a bleaching agent. U.S. Pat. No. 9,642,687, the entire disclosure of which is incorporated herein by reference, discloses that variations in light intensity above a required threshold may have minimal impact on whitening efficacy. While this may be true for whitening treatments with higher hydrogen peroxide concentrations (i.e., 10% or greater), it has been surprisingly found this is not accurate following treatment with lower hydrogen peroxide whitening treatments (i.e., 5% or less).

For example, high intensity light (i.e., about 150 $mW/cm^2$ or greater) activates more tooth stains to an elevated quantum energy level as compared to lower light intensities (e.g., 35 $mW/cm^2$ or 100 $mW/cm^2$) when used in conjunction with an oral care composition with 0.1% $H_2O_2$. As discussed further below in the Examples, a treatment with a composition having 0.1% hydrogen peroxide followed by exposure to a light source with an average light intensity of 35 $mW/cm^2$ afforded roughly only half the whitening benefit of the same treatment but with a light source with a higher average light intensity of 200 $mW/cm^2$. The results illustrate a strong dependence of the whitening benefit at low bleaching agent concentrations on the light source light intensity.

Combining high intensity light with a whitening composition having a relatively low bleaching agent concentration provides increased tolerability of the product over the prescribed usage regimen while providing a meaningful whitening benefit. The combination of a whitening composition having a relatively low bleaching agent concentration (e.g., about 5% or less) followed by applying light with an average light intensity of about 150 $mW/cm^2$ or greater yields a treatment with higher tolerability without compromising the whitening benefit.

The whitening boost provided by light having a high average light intensity may increase as the concentration of bleaching agent decreases. For example, an oral care composition that has about 0.1% $H_2O_2$ may demonstrate a surprisingly high whitening efficacy when used with electromagnetic radiation having a high average light intensity (e.g., about 200 $mW/cm^2$). As described further in the Examples, the whitening boost due to the electromagnetic radiation source surprisingly contributes an increased effect when paired with oral care compositions with low bleaching agent concentrations (e.g., about 5% or less) as compared to oral care compositions with higher bleaching agent concentrations (e.g., greater than about 7%). For example, the whitening boost may be greater than 100%, or greater than 200% at a low bleaching agent concentration (e.g., about 0.1% or about 3%) compared to less than 50% at a high bleaching agent concentration (e.g., about 25%). The whitening boost may be in a range of, for example, from about 100% to about 300%, from about 100% to about 275%, or from about 110% to about 275%, for a whitening composition having a low bleaching agent concentration (e.g., about 3% or less).

The effect of the increase in whitening efficacy as db* or whitening boost from electromagnetic radiation intensity can be illustrated by a ratio of whitening boost to the percent bleaching agent used. Surprisingly, high ratios are observed in oral care compositions with low bleaching agent concentrations due to the increased whitening boost from the electromagnetic radiation. For example, the ratio (db*/% bleaching agent) may be in a range of from about 5 to about 4,000, from about 30 to about 3,000, from about 5 to about 50, from about 2,500 to about 3,000, or from about 35 to about 2,750 or may be about 35, about 38, or about 2,750 for a low bleaching agent concentration. In contrast, the ratio may be about 1 at a high bleaching agent concentration (e.g., about 25% $H_2O_2$ concentration).

The tolerability of whitening oral care compositions is often a reflection of self-reported tooth sensitivity as assessed according to the Clinical Protocol. The tolerability of whitening treatments is important to ensure the consumer can complete the prescribed whitening treatments to ensure they realize the full promised benefit. The user may perform a series of treatments over a multiple days or weeks. A ratio of whitening benefit to tolerability, reflected as self-reported tooth sensitivity (db*/number of subjects reporting sensitive teeth), increases as the bleaching agent concentration decreases (i.e., as the whitening boost increases and tooth sensitivity decreases). A ratio of whitening benefit to tolerability may be in a range of from about 1 to about 100, from about 5 to about 100, from about 5 to about 80, from about 5 to about 75, from about 8 to about 72, from about 5 to about 10, from about 50 to about 100, or from about 65 to about 75 or may be about 5, about 8, about 10, or about 72 for a low bleaching agent concentration. In contrast, the ratio may be less than about 1, or about 0.3, for a high bleaching agent concentration. For example, when a bleaching agent concentration of the whitening composition is about 0.1%, a ratio of a whitening boost from the electromagnetic radiation to self-reported tooth sensitivity may be at least about 70:1 as measured following the final treatment in the series of treatments. When a bleaching agent concentration of the whitening composition is about 3%, a ratio of a whitening boost from the electromagnetic radiation to self-reported tooth sensitivity may be at least about 5:1 as measured following the final treatment in the series of treatments. In contrast, when a bleaching agent concentration of the whitening composition is about 25%, a ratio of a whitening boost from the electromagnetic radiation to self-reported tooth sensitivity may be less than about 0.5:1 as measured following the final treatment in the series of treatments.

A ratio of the percentage of clinical subjects who did not report tooth sensitivity over the full treatment regimen to the bleaching agent concentration (number of subjects not reporting sensitive teeth/% bleaching agent) may also inform the relative tolerability of a whitening treatment. The ratio may be in a range of from about 1 to about 1,500, from about 5 to about 1,500, from about 20 to about 1,200, from about 20 to about 1,000, from about 1 to about 50, from about 10 to about 40, from about 25 to about 35, from about 900 to about 1,000, from about 950 to about 970, or may be about 20, about 25, about 28, about 30, about 950, about 960, or about 970 for a low bleaching agent concentration. In contrast, the ratio may be less than 1, or about 0.4, for a high bleaching agent concentration. This relationship illustrates the strong effect of bleaching agent concentration on the overall incidence of tooth sensitivity probability. The tolerability of whitening treatments is often challenged with associated tooth sensitivity from the treatment. When tooth sensitivity tolerability is experienced during whitening treatments, the full prescribed treatment regimen is often not completed, and the promised benefit is not realized. A user may be more likely to complete a suggested treatment regimen with a higher ratio of the percentage of clinical subjects who did not report tooth sensitivity over the full treatment regimen to the bleaching agent concentration.

Device Fit

The ergonomic fit of a light device in the consumer or patient mouth is important for at least two reasons: (1) light device wear comfort over the recommended light time-period to ensure full compliance of the prescribed treatments to realize the full advertised benefit; and (2) light source placement in closest proximity to the targeted teeth to be whitened to deliver the greatest light intensity and whitening benefit. The anatomical variability of the mouth, within and across genders, makes it challenging to design a light device that fits almost all of a given population. Furthermore, the mouthpiece may be made from a material that is rigid and/or hard to protect the electrical integrity or mechanical integrity of the internal electronics (e.g., to protect against solder breakage). If a mouthpiece is rigid, this rigidity and/or hardness may make it even more challenging to design a device that fits almost all of a population (adults 18 or over). Rigidity can be experienced not only in terms whole mouthpiece flexibility but also local device flexibility based on the durometer or softness of user contact surfaces of the mouthpiece.

The mouthpiece arch of light devices that are currently marketed span a wide range of sizes, shapes, and rigidity. Each of these attributes in turn impacts the fit comfort and the resulting light intensity experienced by the targeted teeth. For example, light device mouthpiece arches could be designed to have a very large arch to ensure all consumers are able to fit the device easily against their front central incisors. However, this may present not only a comfort issue for users with small dental arches but could also place the light source more remote from the first and second premolars resulting in lower light intensity. Conversely, light device mouthpiece arches that are too small will prevent the full insertion of the device mouthpiece for users with large dental arches creating possible discomfort, noncompliant usage, and some first and second pre-molars not receiving any light intensity.

It has been surprisingly found, using a device mouthpiece fit probability assessment, that device fit comfort while emitting light with an intensity of about 150 mW/cm$^2$ or greater from each LED at the targeted teeth can be achieved for 98% or more of a given population. Surprisingly, this high fit range is very narrow and spans only about 3-4 millimeters of a device arch width at a given predetermined depth.

The device point of contact with the mouth is often defined by the shape of the mouthpiece arch, the user's mouth arch, the tooth canine/bicuspid tooth height, and the bite angle of the user during use of the device. The tooth height can determine whether the device will contact the teeth or gums on full insertion. The gums supporting the teeth are wider than the teeth they support, which could cause device interference and fit issues in users with shorter first and/or second bicuspid/premolars. When the mouthpiece is fully inserted into a user's mouth, the width of the user's arch that may contact the device between the distal ends of the mouthpiece may be considered the mouth arch width.

The mouth arch width, at both the buccal surface of teeth and gums, at the depth of the light device on full insertion when the device face contacts front central incisors and/or gums, is important to consider when designing a light device to fit nearly all the population. FIG. 10 shows an example mouth arch width 98. While this mouth arch width is an important dimension to define device full fit, it can vary widely across users and this point may define the true "fit" width. Additionally, the mouth arch width varies within an individual based on the height at which it is measured. For example, a user's mouth arch width measured at the gums is likely to be wider than their mouth arch width measured at the teeth.

Figure 19:
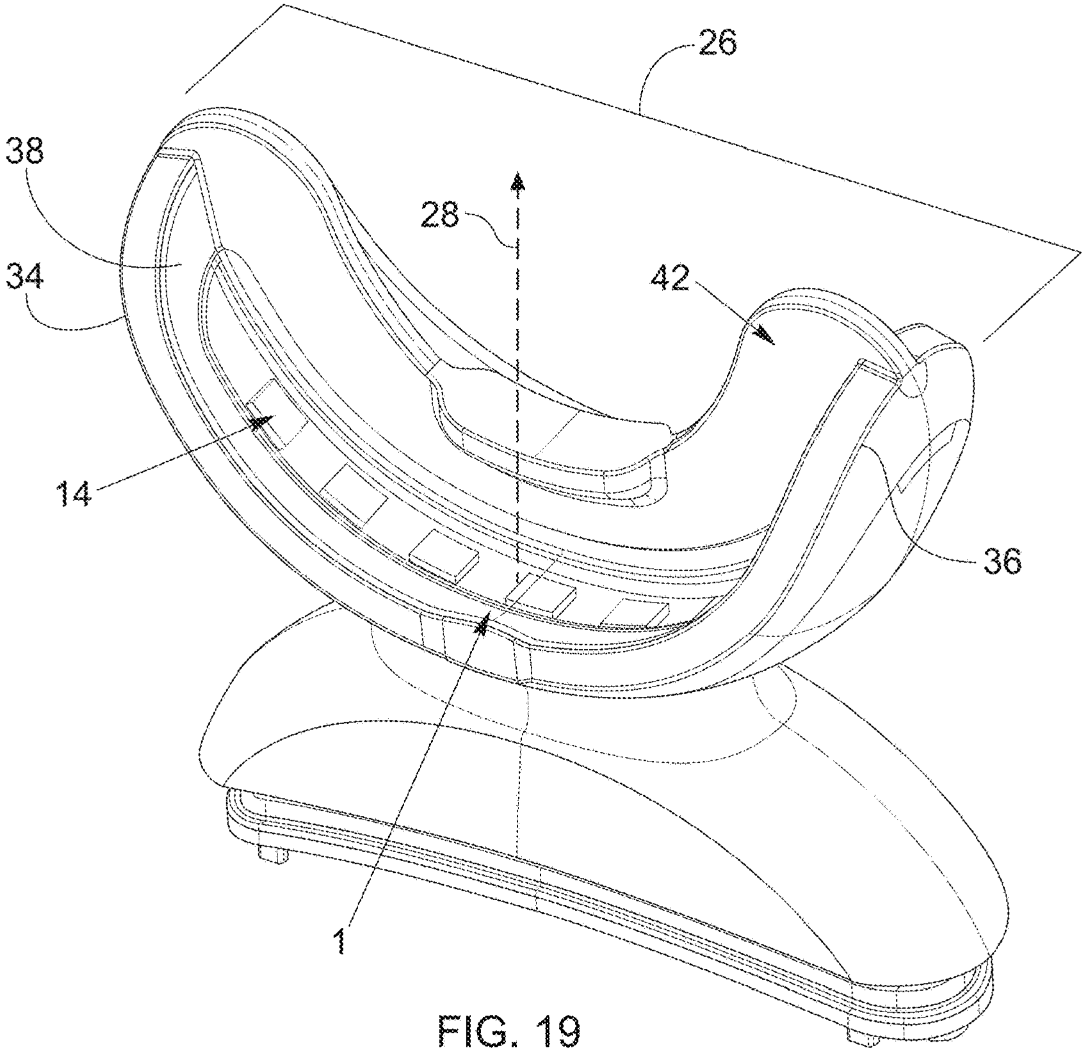
FIG. 19 shows a partial view of the light device of FIG. 1.
Figure 20:
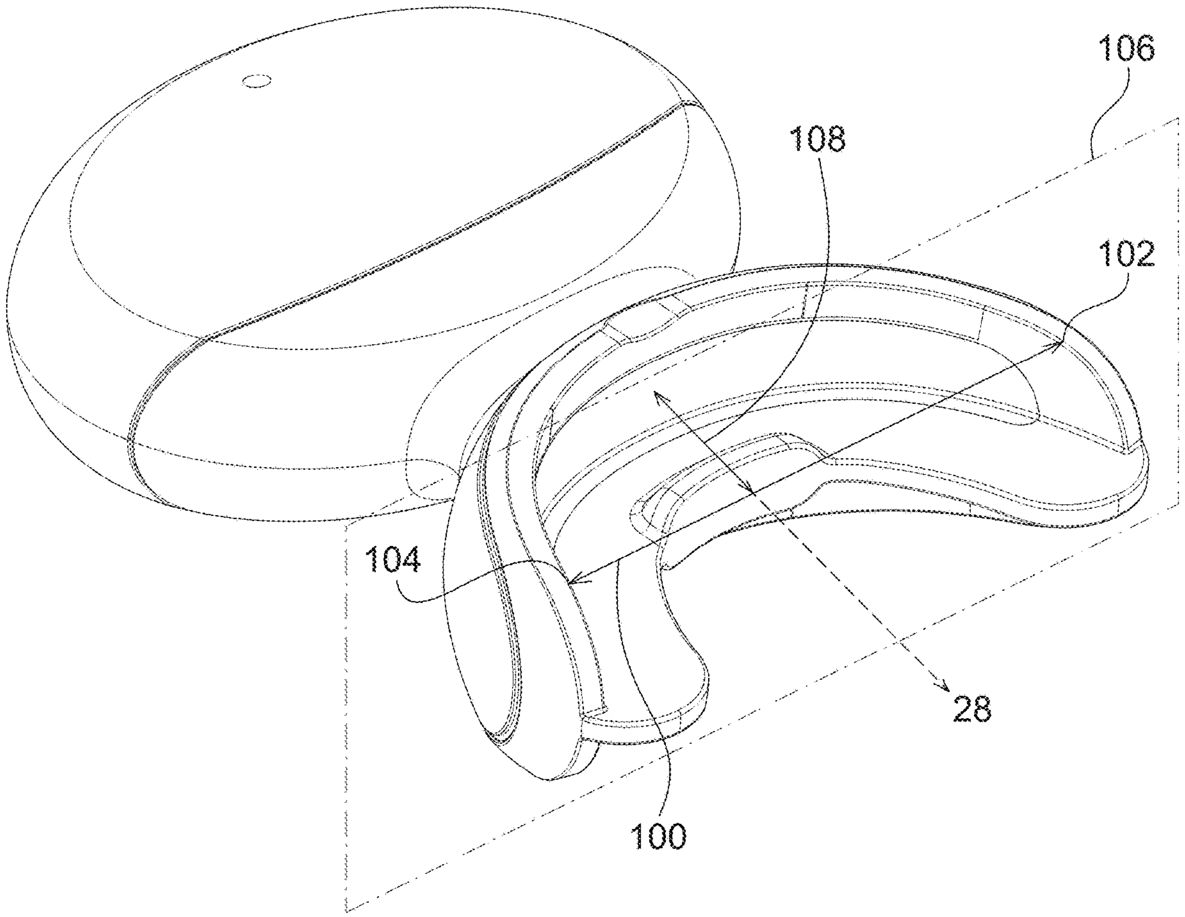
FIG. 20 shows a perspective view of the light device of FIG. 1 showing the device arch width.
Figure 21A:
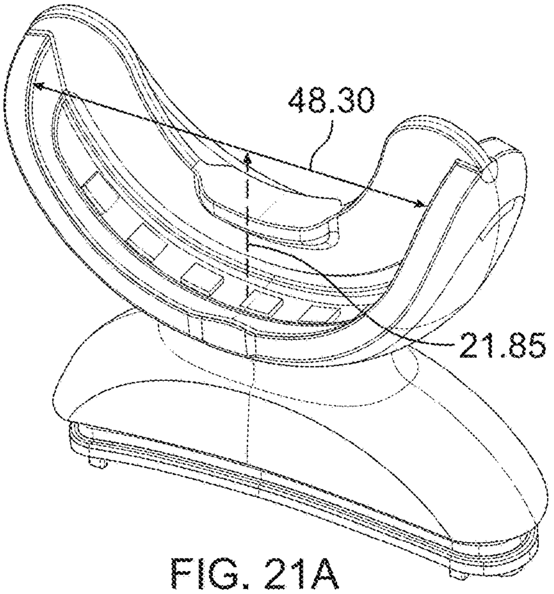
FIGS. 21A and 21B are partial views of a light device according to an embodiment showing a full fit depth and a partial fit depth, respectively, for an example device arch width.
Figure 21B:
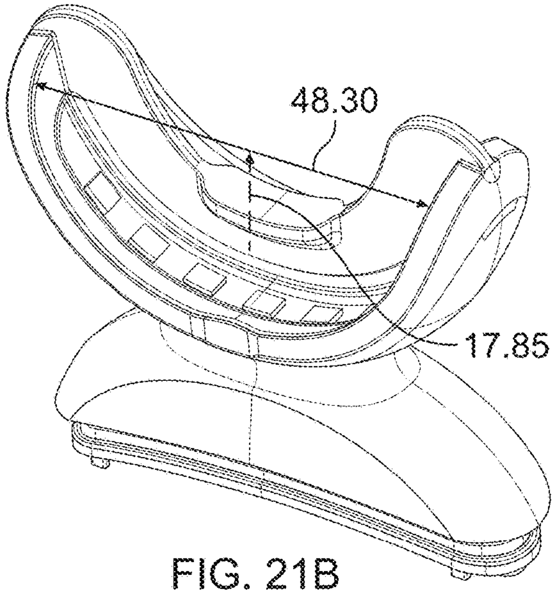
Figure 22A:
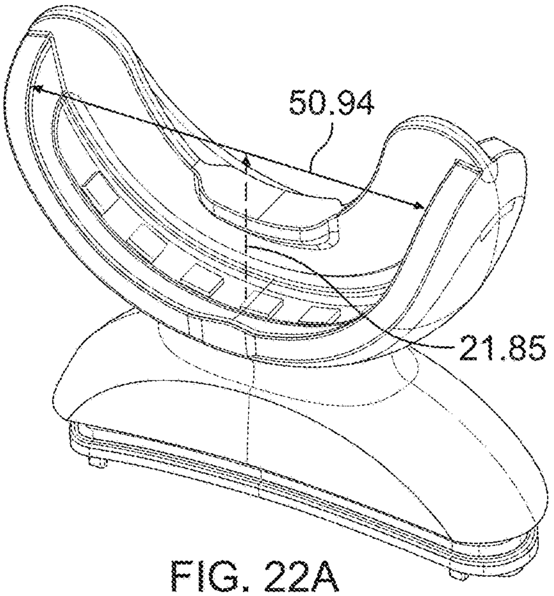
FIGS. 22A and 22B are partial views of a light device according to an embodiment showing a full fit depth and a partial fit depth, respectively, for another example device arch width.
Figure 22B:
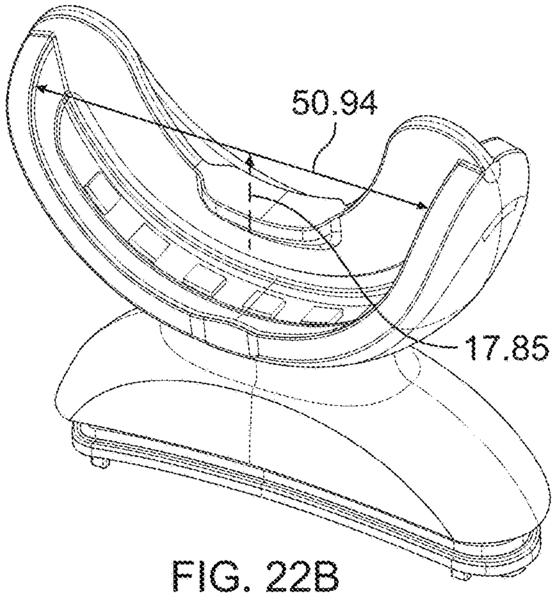

Another important dimension to consider when designing a light device to fit nearly all the population is the device arch width. Referring to FIGS. 19 and 20, the device arch width 100 of the mouthpiece 26 is measured between the highest point 102 of inner surface 38 of the outer wall 34 of the first arm 30 and the highest point 104 of the inner surface 40 of the outer wall 36 of the second arm 32, where the highest points 102, 104 are measured on a plane 106. The plane 106 is orthogonal to the central axis 28 and is spaced at a predetermined depth 108 from the outer surface 22 of the lens 24 along the central axis 28 of the mouthpiece 26.

Surprisingly, the device arch width is the dimension of the light device that most often defines whether the device will fit on full insertion since this is the point that most often contacts the user's teeth or gums. However, the device arch width can vary based on light device design elements. One might assume the interference point between the device and mouth arch will occur at the farthest ends of the mouthpiece arms where each arm end joins with the bite shelf since that extends the furthest into the mouth. However, that would not be the narrowest point in designs where the inner surfaces of the outer arms are tapered inward. Tapering the inner surfaces of the outer arms inward toward the teeth focuses the light emitted on the teeth potentially preventing light loss in designs where the inner surfaces of the outer arms are not tapered inward.

The device arch width can depend on two important dimensions—the predetermined depth and the height of the arms (e.g., from the bite shelf or from the bottom of the teeth). If the inner surfaces of the outer walls are inwardly tapered, a change in arm height may result in a different device arch width at a given predetermined depth. For example, if the arm height is reduced, the highest points on the inner surfaces of the outer walls of the two arms would be both lower and farther apart. Additionally, because the mouth arch width generally decreases from the gums towards the bottom of the teeth, this reduction in height may cause the device arch width to be adjacent a portion of the mouth with a smaller mouth arch width (e.g., the potential interference point may move below the wider gums).

The individual mouth arch, with its variability, and the fixed light dimensions define the area within the mouth where the light device fit is assessed. Full fit of the device ensures the targeted teeth that are most visible when smiling experience the maximum light intensity, which is known to decrease as distance increases from the light source, and maximum whitening benefit. A poor fit may cause users to perform undesired device adjustments to improve fit that may then potentially compromise device performance and the resulting whitening benefit.

In an embodiment where the predetermined depth is in a range of about 15 mm to about 22 mm from the outer surface 24 of the lens 22 along the central axis 28, the device arch width may be in a range from about 41 mm to about 53 mm. In an embodiment where the predetermined depth is in a range of 20 mm to 25 mm, the device arch width may be in a range from about 48 mm to about 53 mm. In an embodiment where the predetermined depth is in a range of about 21 mm to about 22 mm, the device arch width may be in a range from about 48 mm to about 53 mm, about 49 mm to about 52 mm, or about 50 mm to about 52 mm, or may be about 51 mm. In an embodiment where the predetermined depth is about 21.85 mm, the device arch width may be in a range from about 48 mm to about 53 mm, about 49 mm to about 52 mm, or about 50 mm to about 52 mm, or may be about 51 mm. In an embodiment where the predetermined depth is in a range of about 14 mm to about 16 mm, the device arch width may be in a range from about 41 mm to about 47 mm. In an embodiment where the predetermined depth is about 15 mm, the device arch width may be in a range from about 41 mm to about 47 mm, about 42 mm to about 46 mm, or about 43 mm to about 45 mm, or may be about 44 mm.

In various embodiments, the light device may be configured to have a device arch width that provides a full fit to at least 75%, at least 80%, or at least 85% of adults in a given population. In various embodiments, the light device may be configured to have a device arch width that provides a full fit or a partial fit to at least 92%, at least 95%, or at least 98% of adults in a given population.

Examples

The following non-limiting examples further describe preferred embodiments within the scope of the present invention. Many variations of these examples are possible without departing from the scope of the invention. All examples were performed at room temperature (RT) and atmospheric pressure unless stated otherwise.

Procedure to Measure Intensity of Electromagnetic Radiation

The intensity of the electromagnetic radiation can be measured using a spectrometer (USB 2000+ from Ocean Optics) connected to a UV-VIS 200 micron fiber-optic cable with a cosine corrector at the tip (OP 200-2-UV-VIS from Ocean Optics). The spectrometer is connected to a computer running the spectrometer software (Oceanview 1.3.4 from Ocean Optics). The spectrophotometer is calibrated using an Ocean Optics Halogen Light Source (HL-2000-CAL). A given light device is mounted within a vice holder while a light intensity probe is mounted in a jig that is capable of vertical and horizontal displacement from a defined starting point on the light source (0.00 mm). The tip of the fiber-optic cable is held pointing toward the light source at the location where the light intensity is to be measured. The photons collected at the detector surface are guided via the fiber-optic cable to the charge-coupled device in the spectrometer (CCD). The CCD counts photons arriving to the CCD during a pre-determined time period at each wavelength from 200 nm to 1100 nm and uses a software algorithm to convert these photon counts to spectral irradiance ($mW/cm^2/nm$). The spectral irradiance is integrated from 200 nm to 1100 nm by the software to yield the Absolute Irradiance ($mW/cm^2$), which is the intensity of electromagnetic radiation from 200 nm to 1100 nm. The spectral irradiance is integrated from 400 nm to 500 nm by the software to yield the Absolute Irradiance ($mW/cm^2$), which is the intensity of electromagnetic radiation from 400 nm to 500 nm.

For a light device with 30 or fewer LEDs, the overall light intensity for a device is reported as the average of the light intensity of all light source LEDs. For light devices with greater than 30 LED light sources, the light intensity can be measured and averaged across 4 quadrants northwest region 1, northeast region 2, southwest region 3 and southeast region 4.

Light intensities for single LED light sources where heat output was measured was conducted on the single LED as described. Due to LED-to-LED light source intensity variability, the average value reported for a device may differ from an individual LED where heat output was assessed.

Procedure to Measure Light Device Longest Dimension

The longest dimension of a given light device was measured using a "string" based method where string is used to define the longest dimension of a device. The resulting string length is then measured using calipers capable to 0.00 mm. The longest dimension was defined based on the longest measurement for a given device in any orientation of the device including the cord if applicable.

Procedure to Measure LED to LED Spacing

The spacing between LEDs in an array (upper or lower) was measured from the closest edges of each LED as positioned in the device arch of the finished product device. The spacing of the two closest edges was performed using a "string" based method where a string is used to define the shortest distance between two adjacent LED edges. The resulting string length is then measured using calipers capable to 0.00 mm.

Procedure to Measure Light Device Temperature

The device is mounted within a vice holder while a temperature probe (OMEGA HH81 with wire type K Thermocouple) is mounted in a jig that is capable of vertical and horizontal displacement from a defined starting point (0.00 mm).

The temperature probe tip is centered on the outer surface of the lens at the light source center as defined by the maximum intensity of electromagnetic radiation emitted as determined by the Procedure to Measure Intensity of Electromagnetic Radiation. This location is typically centered on the LED source.

The device is equilibrated in the OFF position at ambient temperature (about 22-24° C.) or physiological temperature (about 37° C. in a constant temperature chamber) until the temperature read by the temperature probe does not change by more than 0.2° C. over 2 minutes.

After the temperature has equilibrated, the device is switched ON and the temperature is recorded at each defined time point while the probe is held at the defined vertical and horizontal displacement from the LED center. For measurements recorded at 0 mm, the temperature of the probe in contact with the outer surface of the lens is recorded. For measurements greater than 0 mm, the temperature of the air above the outer surface of the lens at a defined distance is measured. Measurements are recorded as defined above.

Procedure to Measure Temperature of Mouth and Teeth Using Thermal Imaging Camera A thermal imaging camera (FLIR E6) was used to measure the temperature and temperature change of the teeth and mouth before and after exposure to a light device according to the following protocols. All readings were conducted as follows:

1. Subject was instructed not to eat or drink 30 minutes prior to the test.
2. Immediately prior to the temperature measurement, the subject's mouth was held closed for 10 seconds. The subject was instructed to open their mouth and refrain from breathing for 10 seconds.
3. The FLIR camera cross hair was pointed at the front face of the right central incisor and an image of the subject's mouth was captured. The image shows the temperature of the tooth and hottest temperature of the surrounding mouth. Both measurements were recorded.
4. The subject then activated a light device and inserted into their mouth for either 5 or 10 minutes of time.

Ten Minute Light Exposure Procedure:

1. Baseline temperature measurement was taken.
2. Subject immediately placed the Inventive Example I device in their mouth and activated it. It remained on for 10 minutes.
3. Subject removed the Inventive Example I device, and then a temperature measurement was taken.
4. Subject kept mouth closed for 5 minutes, and then a temperature measurement was taken.
5. Subject kept mouth closed for an additional 5 minutes (10 minutes total), and then a temperature measurement was taken.

Five Minute Light Exposure Procedure (3 Replicates):

1. Baseline temperature measurement was taken.
2. Subject immediately placed the Inventive Example I device in their mouth and activated it. It remained on for 5 minutes.

3. Subject removed the Inventive Example I device and a temperature measurement was taken.
4. Subject kept mouth closed for 5 minutes, and then a temperature measurement was taken.
5. Subject kept mouth closed for an additional 5 minutes (10 minutes total), and then a temperature measurement was taken.
6. The above procedure was repeated two additional times, and the 3 values were averaged.

Clinical Protocol

The bleaching efficacies of the oral compositions are measured using the following clinical protocol. Per treatment group, 16 to 25 participants are recruited to complete the clinical study when testing compositions with less than about 1% bleaching agent, and 8 to 25 participants when testing compositions with at least about 1% bleaching agent. Recruited participants must have four natural maxillary incisors with all measurable facial sites. The mean baseline L* of the group of participants must be from 71 to 76, and the mean baseline b* of the group of participants must be from 13 to 18. In addition, participants with malocclusion on maxillary anterior teeth, severe or atypical intrinsic staining, such as that caused by tetracycline, fluorosis or hypo-calcification, dental crowns or restorations on the facial surfaces of maxillary anterior teeth, self-reported medical history of melanoma, current smoking or tobacco use, light-sensitivity or a pigmentation skin disorder, self-reported tooth sensitivity, or previous tooth whitening using a professional treatment, over-the-counter kit, or investigational product, are excluded from the study. Participants are provided with take-home kits with Crest® Cavity Protection toothpaste and Oral-B® Indicator soft manual toothbrush (both from Procter & Gamble, Cincinnati, OH, USA) to be used twice a day in the customary manner.

For studies using Oral Care Composition I or II (defined below), participants use a toothbrush ("Anchor 41 tuft white toothbrush" from Team Technologies, Inc. Morristown, TN, USA) to brush their teeth with water for 30 seconds prior to being treated. The maxillary anterior teeth of each participant are treated with Oral Care Composition I or II for 30 or 60 minutes once daily by direct application of the product directly to the teeth with an applicator or using a strip of polyethylene as a delivery carrier. The polyethylene strips are 66 mm×15 mm in size and 0.0178 mm thick. From 0.6 g to 0.8 g of Oral Care Composition I or II is applied across each strip of polyethylene prior to applying to the maxillary anterior teeth. The polyethylene strip is then either left in place or removed immediately transferring the composition depending on the study definition herein.

If Oral Care Composition I or II is used with electromagnetic radiation:

1) After 50 minutes of treatment with Oral Care Composition I or II on the strip, the electromagnetic radiation is applied toward the facial surfaces of the maxillary anterior teeth for 10 minutes, or alternatively, for 30 minute treatment protocols where Oral Care Composition I or II is applied directly to the teeth, the electromagnetic radiation is applied toward the facial surfaces of the maxillary anterior teeth for the last 5 minutes or 10 minutes of the defined treatment protocol,
2) The electromagnetic radiation is directed toward the maxillary anterior teeth through the strip where applicable and through Oral Care Composition I or II,
3) Where applicable, the strip needs to allow at least about 90% of the electromagnetic radiation from 400 nm to 500 nm to pass through, and
4) The electromagnetic radiation is delivered via four fiber-optic cables (model number M71L01 from Thorlabs, Newton, NJ, USA) connected to four high power LEDs with a peak intensity wavelength of 455 nm (model number M455F1 from Thorlabs, Newton, NJ, USA). The four LEDs are run at 1000 mA each using an LED Driver and Hub (model numbers DC4104 and DC4100-HUB from Thorlabs, Newton, NJ, USA). The exit ends of the four fiber-optic cables are mounted behind a transparent mouthpiece to help position the electromagnetic radiation reproducibly against the outer surface of the strip. The exit ends of the four fiber-optic cables are about 7 mm away from the exit surface of the mouthpiece with the electromagnetic radiation passing through the transparent mouthpiece. The bite shelf of the mouthpiece is offset such that the transparent window through which the electromagnetic radiation passes toward the maxillary anterior teeth is 7.4 mm high. Also, the transparent window through which the electromagnetic radiation passes toward the maxillary anterior teeth is 40 mm long measured linearly from end to end (not including the curvature). The exit ends of the fiber-optic cables are positioned and angled such that the cones of electromagnetic radiation exiting from the fiber-optic cables are centered within the transparent window through which the electromagnetic radiation passes toward the maxillary anterior teeth. Also, the exit ends of the four fiber-optic cables are spaced such that the cones of electromagnetic radiation are spaced across the length of the transparent window through which the electromagnetic radiation passes toward the maxillary anterior teeth. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth needs to be from about 175 $mW/cm^2$ to about 225 $mW/cm^2$ as measured by the method disclosed herein.

The treatment time period, how the product is applied, if the product is occluded, the light intensity employed (if applicable), the light time period (if applicable) and the total number of treatments is defined within each clinical protocol and results section below.

For Oral Care Composition III (defined below), the manufacturer's instructions were followed using the supplied commercial product and a commercial light source as prescribed by the manufacturer. The patient preparation, patient peroxide composition treatment period, and light radiation treatment period along with the treatment time period and total treatments were followed per manufacturer guidance.

The change in tooth color due to the treatment is measured using the procedure described below the day after the final defined treatment with the exception of compositions with at least about 25% bleaching agent where it was measured on the final treatment day.

Tooth color is measured using a digital camera having a lens equipped with a polarizer filter (Camera model no. CANON EOS 70D from Canon Inc., Melville, NY with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle, such that the light paths intersect at the vertical plane of the chin rest about 36 cm in front of the focal plane of the camera. Each light has a polarizing filter (Lee 201 filter), and a cutoff filter (Rosco 7 mil Thermashield filter from Rosco, Stamford, CT, USA).

At the intersection of the light paths, a fixed chin rest is mounted for reproducible repositioning in the light field. The camera is placed between the two lights such that its focal plane is about 36 cm from the vertical plane of the chin rest. Prior to beginning the measurement of tooth color, color standards are imaged to establish calibration set-points. A Munsell N8 grey standard is imaged first. The white balance of the camera is adjusted, such that the RGB values of grey are 200. Color standards are imaged to get standard RGB values of the color chips. The color standards and grey standard are listed below (from Munsell Color, Division of X-rite, Grand Rapids, MI, USA). Each color standard is labeled with the Munsell nomenclature. To create a grid of color standards they can be arranged in the following manner. This enables multiple color standards to be contained in a single image captured of the grid of color standards.

Color standard grid 1

| | | | | | |
|---|---|---|---|---|---|
| 7.5R 6 8 | 2.5R 6 10 | 10YR 6.5 3 | POLARIZATION CHECK | 5R 7 8 | N 3.5 0 |
| 7.5RP 6 6 | 10R 5 8 | 5YR 7 3 | 2.5Y 8.5 2 | 2.2YR 6.47 4.1 | 7.5YR 7 4 |
| 5YR 8 2 | N 8 0 | 10R 7 4 | N 8 0 | 5YR 7.5 2.5 | 2.5Y 8 4 |
| 5YR 7 3.5 | 5YR 7 2.5 | 5YR 5 2 | 5YR 7.5 2 | N 6.5 0 | N 9.5 0 |

Color standard grid 2

| | | | | | |
|---|---|---|---|---|---|
| 5YR 7.5 3.5 | 2.5Y 6 4 | 10YR 7.5 3.5 | 2.5R 7 8 | 7.5R 7 8 | 10YR 7.5 2 |
| 10YR 7.5 2.5 | N 5 0 | 2.5R 6 8 | 10YR 7 2 | 5R 7 4 | 10YR 7 2.5 |
| N 6.5 0 | 7.5RP 6 8 | 7.5R 8 4 | 5Y 8 1 | 7.5YR 8 2 | 2.2YR 6.47 4.1 |
| N 5 0 | 2.5Y 8 4 | 10YR 7 3 | N 9.5 0 | 10RP 7 4 | 2.5Y 7 2 |

Color standard grid 3

| | | | | | |
|---|---|---|---|---|---|
| 5R 6 10 | N 8.5 0 | 10YR 6.5 3.5 | 10RP 6 10 | N 8 0 | 7.5YR 7 3 |
| 2.5Y 3.5 0 | 10YR 7 3.5 | 5Y 8.5 1 | 5YR 8 2.5 | 5YR 7.5 3 | 5R 5 6 |
| 10YR 7.5 3 | 5YR 6.5 3.5 | 2.5YR 5 4 | 2.5Y 8 2 | 10YR 8 2 | 2.5Y 7 2 |
| 2.5R 6 6 | 5R 7 6 | 10YR 8 2.5 | 10R 5 6 | N 6.5 0 | 7.5YR 8 3 |

For baseline tooth color, participants use a toothbrush ("Anchor 41 tuft white toothbrush" from Team Technologies, Inc. Morristown, TN, USA) to brush their teeth with water to remove debris from their teeth. Each participant then uses cheek retractors (from Washington Scientific Camera Company, Sumner, WA, USA; treated with at frosted matte finish at A&B Deburring Company, Cincinnati, OH, USA) to pull the cheeks back and allow the facial surfaces of their teeth to be illuminated. Each participant is instructed to bite their teeth together such that the incisal edges of the maxillary incisors contact the incisal edges of the mandibular incisors. The participants are then positioned on the chin rest at the intersection of the light paths in the center of the camera view and the tooth images are captured. After all participants are imaged, the images are processed using image analysis software (Optimas manufactured by Media Cybernetics, Inc. of Silver Spring, MD). The central four incisors are isolated and the average RGB values of the teeth are extracted.

After the participants have used a whitening product, but prior to capturing participant's tooth images, the system is set to the baseline configuration and calibrated as previously discussed. After calibration, each participant is imaged a second time using the same procedure as before making sure the participant is in the same physical position as the pre-treatment image including orientation of the teeth. The images are processed using the image analysis software to obtain the average RGB values of the central four maxillary incisors. The RGB values of all of the images are then mapped into CIE L*'a*b* color space using the RGB values and the L*a*b* values of the color chips on the color standard. The L*a*b* values of the color chips on the color standard are measured using a Photo Research SpectraScan PR650 from Photo Research Inc., LA using the same lighting conditions described for capturing digital images of the facial dentition. The PR650 is positioned the same distance from the color standards as the camera. Each chip is individually measured for L*a*b* after calibration according to the manufacturer's instructions. The RGB values are then transformed into L*a*b* values using regression equations such as:

$$L^* = 25.16 + 12.02*(R/100) + 11.75*(G/100) - 2.75*(B/100) + 1.95*(G/100)^3$$

$$a^* = -2.65 + 59.22*(R/100) - 50.52*(G/100) + 0.20*(B/100) - 29.87*(R/100)^2 + 20.73*(G/100)^2 + 8.14*(R/100)^3 - 9.17(G/100)^3 + 3.64*[(B/100)^2]*[R/100]$$

$$b^* = -0.70 + 37.04*(R/100) + 12.65*(G/100) - 53.81*(B/100) - 18.14*(R/100)^2 + 23.16*(G/100)*(B/100) + 4.70*(R/100)^3 - 6.45*(B/100)^3$$

The $R^2$ for L*, a*, and b* should be >0.95. Each study should have its own equations.

These equations are generally valid transformations in the area of tooth color (60<L*<95, 0<a*<14, 6<b*<25). The data from each participant's set of images is then used to calculate product whitening performance in terms of changes in L*, a* and b*–a standard method used for assessing whitening benefits. When evaluating compositions with less than about 1% bleaching agent: Changes in L* is defined as $\Delta L^*=L^*_{day\ after\ 7\ treatments}-L^*_{baseline}$ where a positive change indicates improvement in brightness; Changes in a* (red-green balance) is defined as $\Delta a^*=a^*_{day\ after\ 7\ treatments}-a^*_{baseline}$ where a negative change indicates teeth which are less red; Changes in b* (yellow-blue balance) is defined as $\Delta b^*=b^*_{day\ after\ 7\ treatments}-b^*_{baseline}$ where a negative change indicates teeth are becoming less yellow. When evaluating compositions with at least about 1% bleaching agent: Changes in L* is defined as $\Delta L^*=L^*_{after\ 3\ treatments}-L^*_{baseline}$ where a positive change indicates improvement in brightness; Changes in a* (red-green balance) is defined as $\Delta a^*=a^*_{after\ 3\ treatments}-a^*_{baseline}$ where a negative change indicates teeth which are less red; Changes in b* (yellow-blue balance) is defined as $\Delta b^*=b^*_{after\ 3\ treatments}-b^*_{baseline}$ where a negative change indicates teeth are becoming less yellow. $-\Delta b^*$ is used as the primary measure of bleaching efficacy. The overall color change is calculated by the equation $\Delta E\ (\Delta L^{*2}+\Delta a^{*2}+\Delta b^{*2})^{1/2}$.

After using the whitening products, color changes in CIE Lab color space can be calculated for each participant based on the equations given.

To validate this Clinical Protocol, the bleaching efficacy (calculated as $-\Delta b^*$) of the validation composition specified below (delivered on a strip and used with electromagnetic radiation as disclosed herein) needs to be measured the day after the 7th treatment and demonstrated to be >0.5.

TABLE 5

| Validation Composition for Clinical Protocol - Oral Care Composition I | |
|---|---|
| | Wt % |
| 35% aqueous solution $H_2O_2$[1] | 0.2857 |
| Petrolatum[2] | 99.7143 |
| Total | 100.00 |
| % $H_2O_2$ in total oral composition | 0.099995 |

[1]Ultra Cosmetic ® Grade from Solvay, Houston, Texas
[2]g-2191 Grade from Sonneborn, LLC, Parsippany, NJ Procedure to Make the Validation Composition for Clinical Protocol A 500 gram batch of the validation composition is made by weighing the aqueous solution of hydrogen peroxide ($H_2O_2$) and petrolatum into a Speedmixer container ("Max 300 Long Cup Translucent", item number 501 218t from Flacktek Inc., Landrum, SC), and mixing in a Speedmixer at 800 RPM for 5 seconds, 1200 RPM for 5 seconds, and 1950 RPM for 2 minutes. The walls of the container are then scraped down with a plastic spatula, and the contents are mixed a second time at 800 RPM for 5 seconds, 1200 RPM for 5 seconds, and 1950 RPM for 2 minutes. The walls of the container are then scraped down with a plastic spatula, and the contents are mixed a third time at 800 RPM for 5 seconds, 1200 RPM for 5 seconds, and 1950 RPM for 2 minutes.

Procedure to Calculate Whitening Boost from Light

The whitening boost derived from light use as compared to a control when light is not used is calculated by determining the db* difference between the light leg and non-light leg. That db* difference is then divided by the non-light leg benefit level and this value is multiplied by 100 to provide the percent whitening boost derived from light relative to a non-light control leg.

$$\text{Whitening Boost (\%)} = \frac{\begin{array}{c}(\text{Reduction in yellowness from Composition} + \text{Light} - \\ \text{Reduction in yellowness from Composition without Light})\end{array}}{(\text{Reduction in yellowness from Composition without Light})} \times 100$$

An example calculation of whitening boost is below:

db* non-Light Clinical Test Leg: –0.49 db* db* Light Clinical Test Leg at 200 mW/cm$^2$: –1.81 db* db* non-Light Clinical Test Leg–db* Light Clinical Test Leg=–1.84–(–0.49)=–1.32

(–1.32/–0.49)*100=275% Whitening Boost vs. no Light control

Evaluating Fit

A device fit assessment was performed using over 1,400 upper arch digital scans from human subjects to determine the fit probability across a large part of the population. The output of the fit assessment is a cross section of the dental arch at the device arch width overlaid into the design dimensions of a given device. Fit was assessed based on whether the cross section of the mouth arch outer diameter was greater than the device arch width based on different device insertion depths.

With reference to FIGS. 21A-22B, the fit of a device was assessed for two different device arch widths at a predetermined depth of 21.85 mm. The different device arch widths were assessed based on the depth that a user would be able to insert the device into their mouth as measured based on how far the teeth extend past the device arch width dimension. As illustrated in Tables 1 and 2 and FIGS. 21A-22B, the two depths illustrate a user who is able to fully insert the device with front incisor teeth/gums pressed against the center of the lens (21.85 mm) and a user who is unable to fully insert the device but their front incisor top teeth are able to rest within the bite shelf area (17.85 mm), herein termed partial fit. Table 1 shows the results of the fit assessment for the first device design with a device arch width of 48.3 mm.

TABLE 1

| Light Device Fit Assessment via Modeling of Upper Digital Arches for the First Device Design | | |
|---|---|---|
| Distance of Front Teeth/Gums from Lens Face | 0 mm (Full fit) | 4 mm (Partial Fit) |
| Device Arch Width | 48.30 mm | 48.30 mm |
| Depth the Device Arch Width is Inserted into the Mouth | 21.85 mm | 17.85 mm |
| % Arches Device Fit (1424 Arches in Model) | 58% Full Fit | 91% Full or Partial Fit |

Table 1 illustrates surprisingly how light device design can have an impact on device fit, associated comfort, and potential benefit realization. Surprisingly, for a light device design with a mouthpiece with a device arch width of 48.30 mm, only roughly half the population would be able to fully insert the light device against their front incisor teeth and gums and the device would not fit comfortably for roughly 10% of the given population.

Light mouthpiece design improvements were made to improve the light mouthpiece fit across a larger percent of the population. The mouthpiece design was changed in two important dimensions. First, to reduce interference between the first and second arms and the gums, especially for users with shorter canines and bicuspids, the height of the outer walls of the first and second arms was reduced. Because the inner surfaces of the outer walls were inwardly tapered, this reduction in arm height resulted in a wider device arch width at a given predetermined depth (i.e., the highest points on the inner surfaces of the outer walls of the two arms were both lower and farther apart). Additionally, because the mouth arch width generally decreases from the gums towards the bottom of the teeth, this reduction in height caused the device arch width to be adjacent a portion of the mouth with a smaller mouth arch width (e.g., the potential interference point moved below the wider gums). This height reduction ranged from 0.5 mm to 2 mm depending on the location along the mouthpiece arm. Second, in addition to the inherent increase in device arch width due to the arm height reduction, the design was changed to further increase the device arch width. Overall, the device arch width was increased nearly 3 mm greater to about 50 to 51 mm.

The new device dimensions were fit assessed under the same fit scenario conditions as described previously, and the results are shown in Table 2. Surprisingly, the fit probability increased significantly with the design changes with 86% of users being able to fully fit the light device as compared to 58% with the previous design. More importantly, nearly all users (i.e., 98%) should be able to fit the light device with only minor adjustment with their front incisor teeth not fully contacting the outer surface of the lens (i.e., within 4 mm).

TABLE 2

Light Device Fit Assessment via Modeling of Upper Digital Arches for the Second Device Design

| | | |
|---|---|---|
| Distance of Front Teeth/Gums from Lens Face | 0 mm (Full fit) | 4 mm (Partial Fit) |
| Device Arch Width | 50.94 mm | 50.94 mm |
| Depth the Device Arch Width is Inserted into the Mouth | 21.85 mm | 17.85 mm |
| % Arches Device Fit (1424 Arches in Model) | 86% | 98% |
| Increase from First Device Fit to Second Device Fit | 58% to 86% | 91% to 98% |

The fit improvement based on the light device design changes of increased arch width and reduced mouth arch face height is illustrated for the digital dental arch of one subject in Table 3 for both the original and new light device designs. The mouth arch width shown in Table 3 is measured at the various points of contact with the device arch width, which changes based on the size of the device arch width and the depth of insertion. For example, when the arm height is taller in the First Light Design compared to the arm height in the Second Light Design, the mouth arch width is measured at a wider cross-section of the mouth arch (e.g., at the gums).

TABLE 3

Effect of Light Dimensions on Fit

| | First Light Design | | Second Light Design | |
|---|---|---|---|---|
| Distance of Front Teeth/Gums from Lens Face | 0 mm | 4 mm | 0 mm | 4 mm |
| Device Arch Width | 48.30 mm | 48.30 mm | 50.94 mm | 50.94 mm |
| Mouth Arch Width | 51.49 mm | 48.40 mm | 50.89 mm | 48.39 mm |
| Device Fit? | No | No | Yes | Yes |

The device arch width measured at a predetermined depth of 21.85 mm of the Inventive Example I and several commercial examples are illustrated in Table 4 along with the average light intensity for each device. While the device arch widths span a relatively narrow range across light devices (i.e., about 5 mm) the average light intensities span an even larger range (i.e., 10 to 99 $mW/cm^2$ for the commercial examples). The average light intensity is measured at the light source, and one can see how large device arch widths will reduce the light intensity at the first and second premolars with the light sources further from the tooth surface.

TABLE 4

Example Device Arch Widths and Light Intensity Properties

| Device | Device Arch Width (mm) | Average Light Intensity ($mW/cm^2$) |
|---|---|---|
| Inventive Example I | 50.94 | 207 |
| Comparative Example I: GLO Brilliant ® Advanced White Smile | 47.30 | <10 |
| Comparative Example II: Smile Direct Club ® Wireless Whitening Light | 54.50 | 99 |
| Comparative Example III: Colgate ® Optic White ® PRO SERIES LED | 49.50 | 10 |
| Comparative Example IV: SNOW ® Advanced Wireless Teeth Whitening Kit | 51.85 | 51 |
| Comparative Example V: INDIGLOW ® IntelliWHiTE ® Teeth Whitening Light System | 49.80 | 51 |

Evaluating Light Intensity and Heat

A wide range of whitening lights exist that range in portability, power supply, light intensity, and LED number as illustrated in Table 6. While there are a some commercially available lights (Comparative Examples VI & VII) that emit electromagnetic radiation intensity of about 150 $mW/cm^2$ or greater, these lights required a plug-based power source, are not rechargeable and/or are not portable. Other examples that are portable and rechargeable do not provide light at a light intensity of about 150 $mW/cm^2$ or greater.

TABLE 6

| Light Devices Comparison | | | | | | | |
|---|---|---|---|---|---|---|---|
| Device | Portable | Self-Contained | Rechargeable | Weight (g) | Longest Dimension (cm) | No. of LEDs | Avg. Device Intensity (mW/cm$^2$) |
| Inventive Example I | Yes | Yes | Yes | 48.11 | 8.5 | 14 | 207 |
| Comparative Example I: GLO Brilliant ® Advanced White Smile | Yes | No | Yes | 99.01 | >60 | 16 | <10 |
| Comparative Example II: Smile Direct Club ® Wireless Whitening Light | Yes | Yes | Yes | 22.31 | 7.7 | 20 | 99 |
| Comparative Example III: Colgate ® Optic White ® PRO SERIES LED | Yes | Yes | Yes | 31.67 | 8.3 | >700 | 10 |
| Comparative Example IV: SNOW ® Advanced Wireless Teeth Whitening Kit | Yes | Yes | Yes | 36.39 | 8.4 | 20 | 51 |
| Comparative Example V: INDIGLOW ® IntelliWHiTE ® Teeth Whitening Light System | Yes | Yes | Yes | 37.20 | 7.9 | 20 | 51 |
| Comparative Example VI: Clinical Fiber Optic[1] | No | No | No | 2159 | >100 | 1 | 200 |
| Comparative Example VII: Zoom! Whitespeed (Version C2.3 L2.5) | No | No | No | >10000 | >175 | 1 | 200 |

[1]As described in U.S. Pat. No. 11,253,442 beginning at col. 37, line 10.

Heat is a major byproduct when electrical current is applied to a substance due to excitation and vibrations at the atomic level. While light emitting diode (LED) technology has made advancements in both light emission, via electro-luminescence, and heat management, the latter must be managed in applications of high light intensity especially for use in oral care applications.

Table 7 illustrates the heat generation of a single LED from Inventive Example I with light intensity greater than 200 mW/cm$^2$ at physiological temperature (about 37° C.) as measured on the outer surface of the lens of a light device at the center of the LED according to the device temperature measurement method described herein. The data over a 5 minute usage period illustrates a temperature increase of 13.2° C. which continues to increase up to 14.7° C. over 15 minutes.

TABLE 7

| Heat Generation from Inventive Example I over Time at LED Center at 37° C. | | |
|---|---|---|
| Time (Minutes) | Light Intensity (mW/cm$^2$) | Temperature of Outer Surface of Lens at LED Center (° C.) |
| 0 | 215 | 31.7 |
| 1 | 215 | 40.0 |
| 2 | 216 | 42.0 |
| 3 | 210 | 43.3 |
| 4 | 210 | 44.2 |
| 5 | 215 | 44.9 |
| 10 | 208 | 46.2 |
| 15 | 210 | 46.4 |

Excessive exposure to heat from excessive light time periods may be undesirable especially when we surprisingly found the contribution of light intensity on the whitening benefit is most pronounced and steepest during the initial light exposure period (e.g., within the first 5 minutes) and it has been shown that the benefit of light post 5 minutes is not beneficial.

Bleaching Efficacy of Oral Care Composition I with Electromagnetic Radiation Over Different Time Periods The bleaching efficacy of Oral Care Composition I was measured per the Clinical Protocol disclosed herein at different light intensity exposure periods for a 100 mW/cm$^2$ light source as measured according to the Electromagnetic Radiation Intensity protocol. Specifically, this was conducted over one randomized, single-center, two-treatment, parallel group, clinical study conducted on 40 adults who had never had a professional, over-the-counter, or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example 1 with 10 minutes electromagnetic radiation (Oral Care Composition I, Electromagnetic Radiation 100 mW/cm$^2$, 18 participants, mean L* of 74.0 and mean b* of 15.8); or Example 2 with 5 minutes electromagnetic radiation (Oral Care Composition I, Electromagnetic Radiation 100 mW/cm$^2$, 22 participants, mean L* of 74.3 and mean b* of 15.8)

The maxillary anterior teeth of the participants were treated with the Oral Care Composition I for 60 minutes once daily using a strip of polyethylene as a delivery carrier. The polyethylene strips were 66 mm×15 mm in size and 0.0178 mm thick. 0.6 g to 0.8 g of Oral Care Composition I was applied across each strip of polyethylene prior to applying to the maxillary anterior teeth.

Distribution of the assigned maxillary strips and all applications were supervised by a clinical site staff. For each treatment, participants wore a strip with Oral Care Composition I for a total of 60 minutes. For treatment group Example 1, after 50 minutes of each strip wear, a trained hygienist applied electromagnetic radiation toward the facial surfaces of the maxillary anterior teeth for 10 minutes if applicable. For treatment group Example 2, after 55 minutes of each strip wear, a trained hygienist applied electromagnetic radiation toward the facial surfaces of the maxillary anterior teeth for 5 minutes. The electromagnetic radiation was directed toward the teeth through the strip and through the multi-phase oral composition. The electromagnetic radiation was delivered using the source of electromagnetic radiation described herein in the Clinical Protocol. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 85 $mW/cm^2$ to about 115 $mW/cm^2$ as measured by the Procedure to Measure Intensity of Electromagnetic Radiation.

Digital images were collected at baseline and the day after the $7^{th}$ treatment (Day 8).

Both groups using Oral Care Composition I with 5 minutes or 10 minutes of electromagnetic radiation demonstrated a statistically significant ($p<0.0001$), incremental reduction in yellowness ($-\Delta b^*$) at all tested time-points relative to baseline; in addition, increase in lightness ($\Delta L^*$) was observed in this group the day after seven ($p<0.001$).

The group using Oral Care Composition I followed by 100 $mW/cm^2$ electromagnetic intensity for 10 minutes (Example 1) was found to be statistically equivalent ($p<0.639$) in reduction of yellowness ($-\Delta b^*$) at all tested time-points as Example 2 using the same Oral Care Composition I but with 5 minutes of 100 $mW/cm^2$ of electromagnetic radiation.

TABLE 8

Mean Change in Yellowness from Baseline ($\Delta b^*$) after 7 Treatments (Day 8) of Oral Care Composition I (0.1% $H_2O_2$) with Electromagnetic Radiation

| Radiation Period | 5 minutes (Example 2) | 10 minutes (Example 1) |
|---|---|---|
| $\Delta b^*$ | −1.50 | −1.56 |

Light Intensity and Temperature

The light intensity and temperature of a LED is greatest at the LED center and decreases as the measurement source is displaced from the LED center either vertically or horizontally. This is illustrated for Inventive Example I in Table 9 below on the LED center and 1 mm above the lens surface at the center of the LED as measured according to the device temperature measurement method. Assessing the effect of light device heat at 1 mm above the lens surface is a good proxy to reflect the temperature experienced for LEDs positioned between teeth interproximally such as Inventive Example I where an air gap exists, and less heat transfer will occur to the tooth.

TABLE 9

Light Intensity and Temperature as a Function of Vertical Displacement from the LED Center for Inventive Example I

| 0 mm from Lens Face | | 1.0 mm from Lens Face | |
|---|---|---|---|
| Temp (° C.) Change (over 5 minutes) | LED Light Intensity ($mW/cm^2$) | Temp (° C.) Change (over 5 minutes) | LED Light Intensity ($mW/cm^2$) |
| 8.1 | 209 | 6.7 | 121 |

The data in Table 9 illustrate that the highest light intensity and temperature is on the LED center. This is where the highest heat transfer will occur from the LED to any substrate that contacts it directly. Nearly all the rechargeable and portable whitening device comparative examples herein dedicate at least one LED to each tooth intended to be whitened by centering the LED on the tooth for maximum light transmission. A potentially negative consequence of centering LEDs on the nearly flat surface of smile tooth is higher efficiency of heat transfer from the light device LED to the tooth. The LED configuration of Inventive Example I generally positions LEDs between teeth where an air gap exists that more effectively dissipates any heat generated from the LED. The LED temperature difference imparted from this configuration is illustrated in recorded temperature on the lens surface and 1 mm above the surface where a temperature difference of 1.4° C. was measured.

The light intensity and temperature of Inventive Example I was compared to commercially available whitening devices using the same approach as described above at the LED center directly on the lens surface and 1 mm above the surface according to the light intensity and temperature measurement methods. Table 10 illustrates the corresponding light intensity of a given LED and the associated temperature increase over 5 minutes of activation both on the outer surface of the lens and 1 mm above the outer surface.

TABLE 10

Light Intensity and Temperature as a Function of Vertical Displacement from the LED Center for Comparative Examples I-V

| | 0 mm from Lens Face | | 1.0 mm from Lens Face | |
|---|---|---|---|---|
| Comparative Example | Temp (° C.) Change (over 5 minutes) | LED Light Intensity ($mW/cm^2$) | Temp (° C.) Change (over 5 minutes) | LED Light Intensity ($mW/cm^2$) |
| I GLO Brilliant ® Advanced White Smile (heated mouthpiece) | 29.4 | 1.9 | 23.3 | 1.6 |
| II Smile Direct Club ® Wireless Whitening Light | 6.6 | 92 | 5.4 | 59 |
| III Colgate ® Optic White ® PRO SERIES LED | 12.8 | 7.4 | 10.1 | 7.0 |
| IV SNOW ® Advanced Wireless Teeth Whitening Kit | 7.0 | 47.5 | 5.8 | 36.6 |

TABLE 10-continued

Light Intensity and Temperature as a Function of Vertical Displacement from the LED Center for Comparative Examples I-V

| | 0 mm from Lens Face | | 1.0 mm from Lens Face | |
|---|---|---|---|---|
| Comparative Example | Temp (° C.) Change (over 5 minutes) | LED Light Intensity ($mW/cm^2$) | Temp (° C.) Change (over 5 minutes) | LED Light Intensity ($mW/cm^2$) |
| V INDIGLOW ® IntelliWHITE ® Teeth Whitening Light System | 10.0 | 59.4 | 7.7 | 42.9 |

The data in Table 10 illustrate a temperature increase for all tested devices that is greater on the outer surface of the lens as compared to the air that is 1 mm above the outer surface. The extent of temperature increase is not directly correlated to the corresponding light intensity as some lower intensity lights, such as Colgate® Optic White® PRO SERIES LED, emit higher heat even though the associated light intensity is low (i.e., about 10 $mW/cm^2$). In addition, some light devices employ resistors to generate additional heat, such as the GLO Brilliant® Advanced White Smile that increased in temperature on the lens surface nearly 30° C.

The efficiency of a light device LED can be represented in terms of a ratio of the emitted light intensity divided by the temperature increase over a 5 minute on period. This ratio reflects the emitted light intensity required to increase the device temperature 1° C. for a given device LED. This reflects the LED efficiency properties, both light emission and heat management, and device properties. Table 11 shows the ratio of LED light intensity to temperature increase over 5 minutes for various portable, rechargeable devices.

TABLE 11

Ratio of LED Light Intensity to Temperature Increase over 5 Minutes

| Example | 0 mm from Lens Face | 1.0 mm from Lens Face |
|---|---|---|
| | Ratio of LED Light Intensity to Temperature Increase over 5 Minutes | |
| Inventive Example I | 25.8 | 18.1 |
| Comparative Example I: GLO Brilliant ® Advanced White Smile (heated mouthpiece) | 0.1 | 0.1 |
| Comparative Example II: Smile Direct Club ® Wireless Whitening Light | 14.0 | 10.8 |
| Comparative Example III: Colgate ® Optic White ® PRO SERIES LED | 0.6 | 0.7 |
| Comparative Example IV SNOW ® Advanced Wireless Teeth Whitening Kit | 6.8 | 6.3 |
| Comparative Example V INDIGLOW ® IntelliWHITE ® Teeth Whitening Light System | 5.9 | 5.6 |

The efficiency of the LED from Inventive Example I is significantly greater than the efficiency for Comparative Examples I-V both on the outer surface of the lens and at 1 mm above the outer surface.

The effect of Inventive Example I at imparting heat to the teeth and mouth during wear time was assessed over both 5 minute and 10 minute wear time duration according to the Procedure to Measure Temperature of Mouth and Teeth Using Thermal Imaging Camera. Table 12 below illustrates the minimal to low heat transfer of the light device over a 5 minute or 10 minute wear time to both the teeth and the mouth of five subjects. This temperature change was noted to be less than drinking a common hot beverage over 30 seconds.

TABLE 12

Effect of Heat from Inventive Example I on Teeth and Mouth

| Subject | Light Wear Time (mins) | Mouth Temperature Change after Light Exposure (° C., hottest point) | Teeth Temperature Change after Light Exposure (° C., hottest point) | Replicates |
|---|---|---|---|---|
| A | 5 | +0.1 | −0.3 | 3 |
| B | 5 | +0.8 | +2.1 | 3 |
| C | 5 | +1.4 | +3.6 | 3 |
| D | 10 | −1.7 | −0.3 | 1 |
| E | 10 | +2.3 | +5.5 | 1 |

Evaluating Whitening Boost

Oral Care Compositions I and II were multi-phase oral care compositions made using the Procedure to Make the Validation Composition for Clinical Protocol described above and formulated with a 35% aqueous solution of hydrogen peroxide (Table 13). Oral Care Compositions I and II can be made using any suitable procedure such as those disclosed in U.S. Pat. No. 11,147,753, the entire disclosure of which is incorporated herein by reference.

TABLE 13

Oral Care Compositions I and II

| | I | II |
|---|---|---|
| 35% aqueous solution $H_2O_2$[14] (wt %) | 0.2857 | 8.571 |
| Petrolatum[15] (wt %) | 99.7143 | 91.429 |
| total (wt %) | 100.00 | 100.00 |
| wt % $H_2O_2$ in total oral composition | 0.09995 | 2.99985 |

[14]Ultra Cosmetic ® Grade from Solvay, Houston, Texas
[15]g-2191 Grade from Sonneborn, LLC., Parsippany, NJ Oral Care Composition III was a commercial product of Philips Zoom! In Office Professional Teeth Whitening 25% $H_2O_2$ Whitening gel applied after an occlusive barrier has been created and paired with a Zoom! Whitening Light (from Philips, Cambridge, MA, USA).

Bleaching Efficacy of Oral Care Composition I at Different Electromagnetic Radiation Intensities The bleaching efficacy of Oral Care Composition I was measured per the Clinical Protocol disclosed herein at different light intensities as measured according to the Electromagnetic Radiation Intensity protocol. Specifically, this was conducted over three randomized, single-center, two-treatment, parallel group, clinical studies conducted on 74 adults who had never had a professional, over-the-counter, or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example 3 with high electromagnetic radiation (Oral Care Composition I, Electromagnetic Radiation 200 mW/cm$^2$, 19 participants, mean L* of 74.3 and mean b* of 15.6); or Comparative Example 3A-3C with no or low electromagnetic radiation (Oral Care Composition I):

Comparative Example 3A: Electromagnetic Radiation 0 mW/cm$^2$, 21 participants, mean L* of 72.6, and mean b* of 15.9;

Comparative Example 3B: Electromagnetic Radiation 35 mW/cm$^2$, 16 participants, mean L* of 73.6 and mean b* of 16.0; or Comparative Example 3C: Electromagnetic Radiation 100 mW/cm$^2$, 18 participants, mean L* of 74.0 and mean b* of 15.8.

The maxillary anterior teeth of the participants were treated with Oral Care Composition I for 60 minutes once daily using a strip of polyethylene as a delivery carrier. The polyethylene strips were 66 mm×15 mm in size and 0.0178 mm thick. 0.6 g to 0.8 g of the multi-phase oral compositions were applied across each strip of polyethylene prior to applying to the maxillary anterior teeth.

Distribution of the assigned maxillary strips and all applications were supervised by a clinical site staff. For each treatment, participants wore a strip with Oral Care Composition I for a total of 60 minutes. After 50 minutes of each strip wear, a trained hygienist applied electromagnetic radiation toward the facial surfaces of the maxillary anterior teeth for 10 minutes if applicable. Subjects in Comparative Example 3A did not receive light treatment and sat without eating or drinking for the full 60 minutes. The electromagnetic radiation was directed toward the teeth through the strip and through the multi-phase oral composition. The electromagnetic radiation was delivered using the source of electromagnetic radiation described herein in the Clinical Protocol. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be: from about 175 mW/cm$^2$ to about 225 mW/cm$^2$ for Example 3 at 200 mW/cm$^2$; from about 25 to about 45 mW/cm$^2$ for Comparative Example 3B at 35 mW/cm$^2$; and from about 85 to about 115 mW/cm$^2$ for Comparative Example 3C at 100 mW/cm$^2$ as measured by the Procedure to Measure Intensity of Electromagnetic Radiation.

Digital images were collected at baseline and the day after the 7$^{th}$ treatment (Day 8).

The groups using Oral Care Composition I demonstrated a statistically significant ($p<0.0001$), incremental reduction in yellowness (−Δb*) at all tested time-points relative to baseline; in addition, increase in lightness (ΔL*) was observed in this group the day after seven ($p<0.001$).

The group using Oral Care Composition Example I with 200 mW/cm$^2$ electromagnetic intensity (Example 3) demonstrated a statistically significant ($p<0.001$) larger incremental reduction in yellowness (−Δb*) at all tested time-points relative to Comparative Example 3A without light, Comparative Example 3B with light at 35 mW/cm$^2$, and Comparative Example 3C with light at 100 mW/cm$^2$.

TABLE 14

Mean Change in Yellowness from Baseline (Δb*) after 7 Treatments (Day 8) of Oral Care Composition I (0.1% $H_2O_2$) with Increasing Electromagnetic Radiation Intensity

| Intensity | 0 mW/cm$^2$ | 35 mW/cm$^2$ | 100 mW/cm$^2$ | 200 mW/cm$^2$ |
|---|---|---|---|---|
| Δb* | −0.49 | −1.21 | −1.56 | −1.84 |
| % Bleaching Increase (Δb*) from 0 mW/cm$^2$ | NA | +147% | +218% | +275% |

These results demonstrate the surprisingly high whitening efficacy (−1.84) of Oral Care Composition I delivered on a strip and used with electromagnetic radiation of 200 mW/cm$^2$ even though it has less than 0.1% $H_2O_2$.

The percent boost in bleaching efficacy of Oral Care Composition I relative to Comparative Example 3A (without electromagnetic radiation), as measured per the Clinical Protocol as disclosed herein, and calculated as −Δb* increase relative to Comparative Example 3A (without electromagnetic radiation) was: +147% in Comparative Example 3B (35 mW/cm$^2$); +218% in Comparative Example 3C (100 mW/cm$^2$); and +275% in Example 3 (200 mW/cm$^2$).

These results demonstrate the surprisingly high boost in bleaching efficacy derived from increasing electromagnetic radiation intensity with Oral Care Composition I (0.1% $H_2O_2$ concentration) relative to Comparative Example 3A (without electromagnetic radiation). These results are contrary to previously reported results in U.S. Pat. No. 9,642,687 where, for an oral care composition with a higher peroxide concentration of 10%, the whitening benefit boost from electromagnetic radiation source of 134.7 mW/cm$^2$ was reported to only be marginally greater than an electromagnetic radiation source of 41.5 mW/cm$^2$ and hence there was no appreciable benefit of higher intensity light. These results in Table 14 suggest that high intensity light (i.e., about 150 mW/cm$^2$ or greater) activates more tooth stains to an elevated quantum energy level as compared to lower light intensities (e.g., 35 mW/cm$^2$ or 100 mW/cm$^2$) when used in conjunction with an oral care composition with 0.1% $H_2O_2$.

Bleaching Efficacy of Oral Care Composition II with and without Electromagnetic Radiation The bleaching efficacy of Oral Care Composition Example II was measured per the Clinical Protocol disclosed herein at different light intensities as measured according to the Electromagnetic Radiation Intensity protocol. Specifically, this was conducted over one randomized, single-center, two-treatment, parallel group, clinical study conducted on 28 adults who had never had a professional, over-the-counter, or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example 4 with high electromagnetic radiation (Oral Care Composition II, Electromagnetic Radiation 200 mW/cm$^2$, 13 participants, mean L* of 73.7 and mean b* of 16.1); or Comparative Example 4 with no electromagnetic radiation (Oral Care Composition II, Electromagnetic Radiation 0 mW/cm$^2$, 15 participants, mean L* of 73.2 and mean b* of 16.0).

The maxillary anterior teeth of the participants were treated with Oral Care Composition II for 60 minutes once daily. 0.6 g to 0.8 g of the multi-phase oral compositions were applied across the maxillary anterior teeth.

For each treatment, participants did not eat or drink with Oral Care Composition II on and they were assigned for a total of 60 minutes. After 50 minutes of wear, a trained hygienist applied electromagnetic radiation toward the facial surfaces of the maxillary anterior teeth for 10 minutes if applicable. Subjects in the no light (0 mW/cm$^2$) treatment group did not receive light treatment and sat without eating or drinking for a full 60 minutes. The electromagnetic radiation was directed toward the teeth and through the multi-phase oral composition. The electromagnetic radiation was delivered using the source of electromagnetic radiation described herein in the Clinical Protocol. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 175 mW/cm$^2$ to about 225 mW/cm$^2$ as measured by the Procedure to Measure Intensity of Electromagnetic Radiation.

Digital images were collected at baseline and the day after the 7$^{th}$ treatment (Day 8).

All groups using Oral Care Composition II composition demonstrated a statistically significant ($p<0.0001$), incremental reduction in yellowness ($-\Delta b^*$) at all tested time-points relative to baseline; in addition, increase in lightness ($\Delta L^*$) was observed in this group the day after seven ($p<0.001$).

The group using Oral Care Composition II with 200 mW/cm$^2$ electromagnetic intensity (Example 4) demonstrated a statistically significant ($p<0.001$) larger incremental reduction in yellowness ($-\Delta b^*$) at all tested time-points relative to the group using Oral Care Composition II without light (Comparative Example 4).

TABLE 15

Mean Change in Yellowness from Baseline ($\Delta b^*$) after 7 Treatments (Day 8) of Oral Care Composition II (2.99% $H_2O_2$) with and without Electromagnetic Radiation Intensity

| Intensity | 0 mW/cm$^2$ | 200 mW/cm$^2$ |
|---|---|---|
| $\Delta b^*$ | −1.23 | −2.63 |
| % Bleaching Increase ($\Delta b^*$) from 0 mW/cm$^2$ | NA | +113% |

Bleaching Efficacy of Oral Care Composition III with and without Electromagnetic Radiation The bleaching efficacy of Oral Care Composition III was measured per the Clinical Protocol disclosed herein at different light intensities as measured according to the Electromagnetic Radiation Intensity protocol. Specifically, this was conducted over one randomized, single-center, two-treatment, parallel group, clinical study conducted on 31 adults who had never had a professional, over-the-counter, or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example 5 with high electromagnetic radiation (Oral Care Composition III, Electromagnetic Radiation 200 mW/cm$^2$, 20 participants, mean L* of 74.7 and mean b* of 17.8); or Comparative Example 5 with no electromagnetic radiation (Oral Care Composition III, Electromagnetic Radiation 0 mW/cm$^2$, 11 participants, mean L* of 74.7 and mean b* of 18.8).

The maxillary anterior teeth of the participants were treated according to the Philips Zoom! usage instruction by first occluding the soft tissue with a cured barrier. Oral Care Composition III was then applied to the maxillary anterior teeth and the Zoom! Light source applied at 200 mW/cm$^2$ for 15 minutes. The no light treatment group did not receive any light source during each 15 minute exposure. The electromagnetic radiation was directed toward the teeth through Oral Care Composition III over the 15 minute period. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 175 mW/cm$^2$ to about 225 mW/cm$^2$ as measured by the Procedure to Measure Intensity of Electromagnetic Radiation. The process was repeated 2 additional times for a total of 3 treatments of 15 minutes each.

Digital images were collected at baseline and the day following the 3$^{rd}$ treatment (Day 1).

All groups using Oral Care Composition III demonstrated a statistically significant ($p<0.0001$), incremental reduction in yellowness ($-\Delta b^*$) at all tested time-points relative to baseline.

The group using Oral Care Composition III with 200 mW/cm$^2$ electromagnetic intensity (Example 5) demonstrated a statistically significant ($p<0.001$) larger incremental reduction in yellowness ($-\Delta b^*$) at all tested time-points relative to the group using Oral Care Composition III without light (Comparative Example 5).

TABLE 16

Mean Change in Yellowness from Baseline ($\Delta b^*$) after 3 Treatments (Day 1) of Oral Care Composition III (25% $H_2O_2$)

| Intensity | 0 mW/cm$^2$ | 200 mW/cm$^2$ |
|---|---|---|
| $\Delta b^*$ | −2.17 | −2.87 |
| % Bleaching Increase ($\Delta b^*$) from 0 mW/cm$^2$ | NA | +30% |

The whitening boost, mean change in yellowness from baseline ($\Delta b^*$), was clinically measured for Oral Care Compositions with increasing $H_2O_2$ concentrations when used with electromagnetic radiation intensity source of 200 mW/cm$^2$ relative to a control without electromagnetic radiation. The whitening boost of a 200 mW/cm$^2$ electromagnetic radiation source as a function of the peroxide concentration of a whitening composition is illustrated in Table 17 below.

TABLE 17

Whitening Boost, Mean Change in Yellowness from Baseline ($\Delta b^*$), of Oral Care Compositions I-III with Electromagnetic Radiation Intensity of 200 mW/cm$^2$ Relative to a Control without Electromagnetic Radiation

| Oral Care Composition | Peroxide Concentration | Whitening Boost of 200 mW/cm$^2$ vs a Control without EMR | Ratio of Whitening Boost (%) to Peroxide Concentration (%) |
|---|---|---|---|
| I | 0.1% | 275% | 2750 |
| II | 3% | 113% | 38 |
| III | 25% | 30% | 1 |

These results illustrate the decreasing whitening boost from a 200 mW/cm$^2$ electromagnetic radiation source when used with oral care compositions with increasing $H_2O_2$ concentration. The whitening boost decreases from +275% with 0.1% $H_2O_2$ to +113% with 3% $H_2O_2$ down to +30% with 25% $H_2O_2$. It was previously reported in U.S. Pat. No. 9,642,687 that the whitening boost from light of oral care compositions of 10% $H_2O_2$ was only marginally different between electromagnetic radiation intensities of 41.5 mW/cm$^2$ and 134.7 mW/cm$^2$, which suggests lower intensity light (41.5 mW/cm$^2$) is sufficient for stain activation and higher intensity doesn't provide additional benefit. These results illustrate electromagnetic radiation source is contributing an increased effect on whitening with oral care compositions with low peroxide concentrations (e.g., 3% or less) as compared to oral care compositions with higher peroxide concentrations (e.g., greater than 7%).

The effect of the increase in whitening efficacy as db* or whitening boost from electromagnetic radiation intensity is illustrated by its ratio with the percent peroxide used in the treatment period during the Clinical Protocol. Surprisingly, high ratios are observed in oral care compositions with low peroxide concentrations due to an increased whitening boost from electromagnetic radiation. The ratio in an oral care composition containing 0.1% $H_2O_2$ is surprisingly 2750 and the ratio decreases as the hydrogen peroxide concentration in the oral care composition increases with the ratio at 3% $H_2O_2$ equal to 38 and the ratio nearly 1:1 at 25% $H_2O_2$ concentration.

The tolerability of whitening treatments is important to ensure the consumer can complete the prescribed whitening treatments to ensure they realize the full promised benefit. The tolerability of whitening oral care compositions is often a reflection of self-reported tooth sensitivity as assessed according to the Clinical Protocol. The self-reported clinical tooth sensitivity on the final day of the prescribed total treatments for Oral Care Compositions I-III in combination with electromagnetic radiation intensity at 200 mW/cm$^2$, as defined in the Procedure to Measure Intensity of Electromagnetic Radiation, is reported in Table 18 below.

TABLE 18

Self-Reported Tooth Sensitivity of Oral Care Compositions I-III in Combination with Electromagnetic Radiation

| Oral Care Composition | % Self-Reported Tooth Sensitivity on the last day of the defined Treatment Period | % Reported No Tooth Sensitivity on the last day of the defined Treatment Period |
|---|---|---|
| I (0.1% $H_2O_2$) | 4% | 96% |
| II (3% $H_2O_2$) | 15% | 85% |
| III (25% $H_2O_2$) | 90% | 10% |

Not surprisingly, the associated self-reported tooth sensitivity of Oral Care Compositions I-III increases with increasing treatment peroxide concentration independent of electromagnetic radiation treatment. Only about 4% self-reported tooth sensitivity was reported when using Oral Care Composition I (0.1% $H_2O_2$) according to the Clinical Protocol. Self-reported tooth sensitivity significantly increases from 15% to 90% with increasing peroxide concentration in Oral Care Compositions II and III according to the Clinical Protocol.

The whitening and tolerability, reflected as self-reported tooth sensitivity, of Oral Care Compositions I-III used in conjunction with electromagnetic radiation can be reflected in ratios as illustrated in Table 19 below.

TABLE 19

Efficacy and Self-Reported Sensitivity Tolerability for Oral Care Compositions I-III in Combination with Electromagnetic Radiation

| Oral Care Composition | Ratio of Whitening Boost from Oral Care Composition with 200 mW/cm$^2$ Electromagnetic Radiation (vs no Electromagnetic Radiation) to Self-Reported Tooth Sensitivity | Ratio of % No. Reported Tooth Sensitivity Following Oral Care Composition and Electromagnetic Radiation Treatment to % Peroxide in Oral Care Composition |
|---|---|---|
| I (0.1% $H_2O_2$) | 72:1 | 960:1 |
| II (3% $H_2O_2$) | 8:1 | 28:1 |
| III (25% $H_2O_2$) | 0.3:1 | 0.4:1 |

The ratio of the whitening boost of oral care compositions when used with an electromagnetic radiation source (as compared to a no light control) to the percent of clinical subjects who reported tooth sensitivity is illustrated. Surprisingly this ratio is the greatest as the peroxide concentration of the oral care composition decreases as the whitening boost increases and tooth sensitivity decreases. The ratio difference between Oral Care Composition I (0.1% $H_2O_2$) and Oral Care Composition III (25% $H_2O_2$) is greater than 200.

The ratio can also be reported as the percentage of clinical subjects who did not report tooth sensitivity over the full treatment regimen divided by the percent peroxide of the oral care composition. The ratio difference between Oral Care Composition I (0.1% $H_2O_2$) and Oral Care Composition III (25% $H_2O_2$) is 2400. This strongly illustrates the effect of percent peroxide of the oral care composition on the overall incidence of tooth sensitivity probability. The tolerability of whitening treatments is often challenged with associated tooth sensitivity from the treatment. When tooth sensitivity tolerability is experienced during whitening treatments the full prescribed treatment regimen is not completed and the promised benefit is not realized. The tooth sensitivity-based tolerability of Oral Care Compositions I and II along with the associated whitening boost from electromagnetic radiation surprisingly illustrates that oral care compositions with a lower $H_2O_2$ concentration have higher ratios of whitening boost to overall tolerability as tooth sensitivity.

As previously reported in commonly assigned U.S. Pat. No. 9,622,840, the whitening boost derived from the use of electromagnetic radiation is highly dependent on when the electromagnetic radiation is applied. This is described as a peroxide-based chemistry first usage period followed by a second period of electromagnetic radiation where the first usage period is greater than 50% of the total first and second usage periods. This is exemplified in Table 20 below, which investigated the whitening benefit of a 3% peroxide composition as a function of when an electromagnetic radiation source was applied during the first peroxide chemistry treatment period.

Bleaching Efficacy of Oral Care Composition II as a Function of Electromagnetic Radiation Timing The bleaching efficacy of Oral Care Composition II as a function of when an electromagnetic radiation was applied during the first chemistry usage period was measured per the Clinical Protocol disclosed herein. Specifically, this was conducted over one randomized, single-center, four-treatment, parallel group, clinical study conducted on 75 adults who had never had a professional, over-the-counter, or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example 6 with electromagnetic radiation after 25 minutes: (Oral Care Composition II, Electromagnetic Radiation 35 mW/cm$^2$, 18 participants, mean L* of 72.2 and mean b* of 15.8) or Comparative Examples 6A-6C (Oral Care Composition II):

Comparative Example 6A without electromagnetic radiation (Electromagnetic Radiation 0 mW/cm$^2$, 20 participants, mean L* of 72.6 and mean b* of 15.9);

Comparative Example 6B with electromagnetic radiation after 5 minutes (Electromagnetic Radiation 35 mW/cm$^2$, 17 participants, mean L* of 72.6 and mean b* of 15.9); or Comparative Example 6C with electromagnetic radiation after 15 minutes (Electromagnetic Radiation 35 mW/cm$^2$, 20 participants, mean L* of 72.6 and mean b* of 15.9).

The maxillary anterior teeth of the participants were treated for 5, 15, 25, or 30 minutes once daily using Oral Care Composition II applied to the maxillary anterior teeth prior to electromagnetic radiation treatment except for the group that had no electromagnetic radiation.

Distribution of the assigned product and all applications were supervised by a clinical site staff. For each treatment, participants did not eat or drink with Oral Care Composition on and they were assigned for a total of 5, 15, 25, or 30 minutes. After the defined minutes of peroxide composition wear, a trained hygienist applied electromagnetic radiation toward the facial surfaces of the maxillary anterior teeth for 5 minutes if applicable. Subjects in Comparative Example 6A treatment group did not receive light treatment and sat without eating or drinking for a full 30 minutes. The electromagnetic radiation was directed toward the teeth through the multi-phase oral composition. The electromagnetic radiation was delivered using the electromagnetic radiation source available from the commercial product Crest® Whitestrips® Plus Light. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 25 mW/cm$^2$ to about 45 mW/cm$^2$ as measured by the Procedure to Measure Intensity of Electromagnetic Radiation.

Digital images were collected at baseline and the day after the 14$^{th}$ treatment (Day 15).

All groups using Oral Care Composition II demonstrated a statistically significant ($p<0.0001$), incremental reduction in yellowness (−Δb*) at all tested time-points relative to baseline.

The group using Oral Care Composition II with 35 mW/cm$^2$ electromagnetic intensity applied after 25 minutes of the first peroxide composition usage period (Example 6) demonstrated a statistically significant ($p<0.001$) larger incremental reduction in yellowness (−Δb*) at all tested time-points relative to the group using Oral Care Composition II without light (Comparative Example 6A) and when light was applied at 5 minutes and 15 minutes after the first peroxide composition usage period (Comparative Examples 6B and 6C, respectively).

TABLE 20

Whitening Benefit of Oral Care Composition II (3% Peroxide) as a Function of Electromagnetic Radiation Timing

| | First Peroxide Usage Period (mins) | Second Light Usage Period (mins) | % First Usage Period of Total Usage Time | Mean Change in Yellowness from Baseline (Δb*) after 14 Treatments (Day 15) |
|---|---|---|---|---|
| No Light | 30 | 0 | 100 | −1.09 |
| Light after 5 mins | 5 | 5 | 50 | −1.04 |
| Light after 15 mins | 15 | 5 | 75 | −0.99 |
| Light after 25 mins | 25 | 5 | 83 | −1.62 |

The data in Table 20 illustrates the importance of a minimum first peroxide chemistry only usage period to allow for time for hydrogen peroxide to diffuse into the tooth and be in proximity to the stain when electromagnetic radiation is applied to photoactivate the stain bleaching process. When electromagnetic radiation was applied after 5 or 15 minutes of the first period chemistry usage period the whitening benefit was the same as when electromagnetic radiation was not used. When light was applied after 25 minutes of a peroxide composition usage period the benefit was 50% greater.

While particular embodiments have been illustrated and described herein, various other changes and modifications may be made without departing from the spirit and scope of the invention. Moreover, although various aspects of the invention have been described herein, such aspects need not be utilized in combination. It is therefore intended to cover in the appended claims all such changes and modifications that are within the scope of the invention.

The terms "substantially," "essentially," "about," "approximately," and the like, as may be used herein, represent the inherent degree of uncertainty that may be attributed to any quantitative comparison, value, measurement, or other representation. These terms also represent the degree by which a quantitative representation may vary from a stated reference without resulting in a change in the basic function of the subject matter at issue. Further, the dimensions and values disclosed herein are not to be understood as being strictly limited to the exact numerical values recited. Instead, unless otherwise specified, each such dimension is intended to mean both the recited value and a functionally equivalent range surrounding that value. For example, values disclosed as "3 cm" or "50 degrees" are intended to mean, respectively, "about 3 cm" or "about 50 degrees."

The disclosure of every document cited herein, including any cross-referenced or related patent or application, and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein—or that it alone, or in any combination with any other reference or references, teaches, suggests, or discloses any such invention. Further, to the extent that any meaning or definition of a term in this document conflicts with any meaning or definition of the same or similar term in a document incorporated by reference, the meaning or definition assigned to or contextually implied by that term in this document shall govern.

What is claimed is:

1. An oral care light device comprising:

a housing comprising a lens having an outer surface;

a light source positioned in the housing, the light source being capable of emitting electromagnetic radiation with a wavelength of 440 nm to about 490 nm and an average light intensity of about 150 $mW/cm^2$ or greater, wherein the light source comprises a first array of LEDs configured to align a center of each of the LEDs of the first array with a corresponding interproximal space between teeth, wherein the first array of LEDs comprises a central LED positioned interproximally of two top front teeth, and the first array of LEDs has an edge-to-edge LED spacing in a range of about 5 mm to about 6.5 mm and a plurality of remaining LEDs; and a battery positioned in the housing, the battery being rechargeable or replaceable, wherein the device is portable.

2. The device of claim 1, wherein the battery is a rechargeable battery configured to supply at least seven 5-minute uses based on a single full charge independent of battery age.

3. The device of claim 1, wherein the first array of LEDs is an upper array.

4. The device of claim 3, wherein the device further comprises a second array of LEDs that is a lower array such that a central LED of the second array is positioned interproximally of two lower front teeth, and the second array of LEDs has an edge-to-edge LED spacing in a range of about 2 mm to about 4 mm.

5. The device of claim 1, wherein the light source is configured to emit a higher light intensity towards an interproximal space between two teeth than towards a facial surface of either of the two teeth.

6. The device of claim 1, further comprising a timer configured to activate the light source after a delay period of time and is configured to prevent reactivation of the light source for a sleep period of time.

7. The device of claim 1, wherein a temperature increase of the outer surface of the lens as measured at a center of an LED is less than 10° C. during 5 minutes of use as measured according to the light device temperature method.

8. The device of claim 1, wherein a temperature increase of air at 1 mm from the outer surface of the lens as measured at a center of an LED is less than 8° C. during 5 minutes of use as measured according to the light device temperature method.

9. The device of claim 1, wherein a ratio of an average light intensity output to a temperature increase of the outer surface of the lens as measured at the LED center is greater than 25 $mW/cm^2/°$ C. as measured according to the light device temperature method.

10. The device of claim 1, wherein the device has a total weight of 500 grams or less.

11. The device of claim 1, wherein the device is water resistant and has an International Electrotechnical Commission (IEC) standard IEC 60529 rating of IPX3, IPX4, IPX5, IPX6, IPX7, IPX8, or IPX9.

12. The device of claim 1, wherein the device is self-contained.

13. The device of claim 1, wherein the housing comprises a mouthpiece, and the mouthpiece comprises a first arm having a first inner surface, a second arm having a second inner surface, and a bite shelf extending along the first inner surface and the second inner surface.

14. The device of claim 13, wherein the first arm and the second arm extend above and below the bite shelf.

15. The device of claim 14, wherein the bite shelf extends past the first arm and the second arm.

16. The device of claim 1, wherein the light source comprises an upper array of LEDs having an upper array focal point and a lower array of LEDs having a lower array focal point, wherein the upper array focal point is closer to the device than the lower array focal point.

17. The device of claim 1, wherein the device is water resistant and has an International Electrotechnical Commission (IEC) standard IEC 60529 rating of in a range of IPX3 through IPX9.

18. A kit comprising the oral care light device of claim 1 and a whitening composition.

19. A method of whitening teeth using the oral care light device of claim 1, the method comprising:

applying a whitening composition including a peroxide active to the teeth;

maintaining the whitening composition on the teeth for a first time period of greater than 0 seconds to about 120 minutes without activating the light source; and after the first time period, activating the light source to direct the electromagnetic radiation toward the teeth for a second time period of greater than 0 seconds to 120 minutes, wherein each LED is aligned interproximally.

* * * * *